(12) United States Patent
Kim et al.

(10) Patent No.: US 7,598,398 B2
(45) Date of Patent: Oct. 6, 2009

(54) ACYL INDOLES, COMPOSITIONS CONTAINING SUCH COMPOUNDS AND METHODS OF USE

(75) Inventors: Ronald M. Kim, Summit, NJ (US); Amy R. Bittner, Scotch Plains, NJ (US); Christopher Joseph Sinz, Cranford, NJ (US); Emma R. Parmee, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 11/580,714

(22) Filed: Oct. 13, 2006

(65) Prior Publication Data

US 2007/0088071 A1   Apr. 19, 2007

(51) Int. Cl.
  *C07D 209/12*  (2006.01)
  *A61K 31/33*  (2006.01)
(52) U.S. Cl. ........................... 548/493; 514/183
(58) Field of Classification Search ............ 548/493
  See application file for complete search history.

(56) References Cited

U.S. PATENT DOCUMENTS 5,776,954 A   7/1998   de Laszlo et al.

FOREIGN PATENT DOCUMENTS

| WO | WO 97/16442 | 5/1997 |
|----|----|----|
| WO | WO 98/04528 | 2/1998 |
| WO | WO 98/21957 | 5/1998 |
| WO | WO 98/22108 | 5/1998 |
| WO | WO 98/22109 | 5/1998 |
| WO | WO 99/01423 | 1/1999 |
| WO | WO 99/32448 | 7/1999 |
| WO | WO 00/39088 | 7/2000 |
| WO | WO 00/69810 | 11/2000 |
| WO | WO 02/00612 | 1/2002 |
| WO | WO 02/40444 | 5/2002 |
| WO | WO 03/048109 | 6/2003 |
| WO | WO 03/051357 | 6/2003 |
| WO | WO 03 053938 | 7/2003 |
| WO | WO 03/064404 | 8/2003 |
| WO | WO 03/097619 | 11/2003 |
| WO | WO 2004/002480 | 1/2004 |
| WO | WO 2004/050039 | 6/2004 |
| WO | WO 2004/056763 | 7/2004 |
| WO | WO 2004/062663 | 7/2004 |
| WO | WO 2004/069158 | 8/2004 |
| WO | WO 2006/007542 A1 * | 1/2006 |

OTHER PUBLICATIONS

Vippagunta, et al. Advanced Drug Delivery Reviews 48 (2001) 3-26.*
R. Kurukulasuriya et al., "Biaryl amide glucagon receptor antagonists", Bioorganic & Medicinal Chemistry Letters, vol. 14, pp. 2047-2050 (2004).
R. Kurukulasuriya et al., "Towards a Potent Small Molecule Glucagon Receptor Antagonist", 228th ACS National Meeting, Abstract 35, Aug. 2004.
A. L. Handlon et al., "Glucagon Receptor Antagonists for the Treatment of Type 2 Diabetes", 226th ACS National Meeting, Abstract 164, Sep. 2003.
H. S. Jae et al., "Antagonists of Glucagon Receptor for Type 2 Diabetes Treatment", 228th ACS National Meeting, Abstract 36, Aug. 2004.

* cited by examiner

*Primary Examiner*—Rebecca L Anderson
*Assistant Examiner*—Shawquia Young
(74) *Attorney, Agent, or Firm*—Richard C. Billups; Catherine D. Fitch

(57) ABSTRACT

The present invention relates to substituted indoles, compositions containing such compounds and methods of treatment The compounds are glucagon receptor antagonists and thus are useful for treating, preventing or delaying the onset of type 2 diabetes mellitus and related conditions.

17 Claims, No Drawings

ACYL INDOLES, COMPOSITIONS CONTAINING SUCH COMPOUNDS AND METHODS OF USE

BACKGROUND OF THE INVENTION

The present invention relates to substituted acyl indole derivatives, compositions containing such compounds and methods of treating type 2 diabetes mellitus and related conditions.

Diabetes refers to a disease process derived from multiple causative factors and is characterized by elevated levels of plasma glucose (hyperglycemia) in the fasting state or following glucose administration during an oral glucose tolerance test. Frank diabetes mellitus (e.g., a blood glucose level ≧126 mg/dL in a fasting state) is associated with increased and premature cardiovascular morbidity and mortality, and is related directly and indirectly to various metabolic conditions, including alterations of lipid, lipoprotein and apolipoprotein metabolism.

Patients with non-insulin dependent diabetes mellitus (type 2 diabetes mellitus), approximately 95% of patients with diabetes mellitus, frequently display elevated levels of serum lipids, such as cholesterol and triglycerides, and have poor blood-lipid profiles, with high levels of LDL-cholesterol and low levels of HDL-cholesterol. Those suffering from Type 2 diabetes mellitus are thus at an increased risk of developing macrovascular and microvascular complications, including coronary heart disease, stroke, peripheral vascular disease, hypertension (for example, blood pressure ≧130/80 mmHg in a resting state), nephropathy, neuropathy and retinopathy.

Patients having type 2 diabetes mellitus characteristically exhibit elevated plasma insulin levels compared with nondiabetic patients; these patients have developed a resistance to insulin stimulation of glucose and lipid metabolism in the main insulin-sensitive tissues (muscle, liver and adipose tissues). Thus, Type 2 diabetes, at least early in the natural progression of the disease is characterized primarily by insulin resistance rather than by a decrease in insulin production, resulting in insufficient uptake, oxidation and storage of glucose in muscle, inadequate repression of lipolysis in adipose tissue, and excess glucose production and secretion by the liver. The net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

Glucagon serves as the major regulatory hormone attenuating the effect of insulin in its inhibition of liver gluconeogenesis and is normally secreted by pancreatic islet cells in response to falling blood glucose levels. The hormone binds to specific receptors in liver cells that triggers glycogenolysis and an increase in gluconeogenesis through cAMP-mediated events. These responses generate glucose (e.g. hepatic glucose production) to help maintain euglycemia by preventing blood glucose levels from falling significantly.

In addition to elevated levels of circulating insulin, type II diabetics have elevated levels of plasma glucagon and increased rates of hepatic glucose production. Antagonists of glucagon are useful in improving insulin responsiveness in the liver, decreasing the rate of gluconeogenesis and lowering the rate of hepatic glucose output resulting in a decrease in the levels of plasma glucose.

SUMMARY OF THE INVENTION

The present invention is directed to a compound represented by formula I:

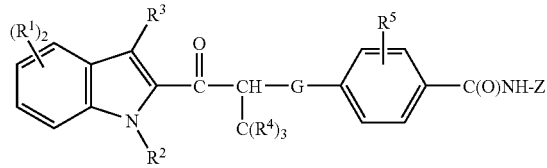

or a pharmaceutically acceptable salt or solvate thereof, wherein:

each $R^1$ represents H or is independently selected from the group consisting of:

a) OH, halo, $CO_2R^a$, $C(O)NR^bR^c$, $NR^bR^c$, CN or $S(O)_pR^d$; and b) $C_{1-10}$alkyl, $C_{2-10}$alkenyl, $OC_{1-10}$alkyl and $OC_{3-10}$alkenyl, said groups being optionally substituted with: (1) 1-5 halo groups up to a perhaloalkyl group; (2) 1 oxo group; (3) 1-2 OH groups; (4) 1 phenyl ring, which is optionally substituted as follows: 1-5 halo groups up to perhalo, 1-3 $C_{1-10}$alkyl or alkoxy groups, each being further optionally substituted with 1-5 halo up to perhalo;

$R^2$ represents hydrogen or is selected from the group consisting of:

a) $C_{1-14}$alkyl or $C_{2-10}$alkenyl, said alkyl and alkenyl group being optionally substituted with 1-5 halo atoms up to perhalo; 1-2 OH, $S(O)_pR^d$, $C_{1-6}$alkoxy or halo$C_{1-6}$alkoxy groups; and 1-2 Aryl, HAR or Hetcy groups, each optionally substituted with 1-3 halo atoms, 1-4 $C_{1-6}$alkyl groups and 1-2 groups selected from CN, $NO_2$, $S(O)_pR^d$, halo$C_{1-6}$alkyl, $C_{1-6}$alkoxy and halo$C_{1-6}$alkoxy groups; and b) Aryl, HAR or Hetcy, each optionally substituted with 1-3 halo groups and 1-2 groups selected from CN, $NO_2$, $S(O)_pR^d$, $C_{1-6}$alkyl, $C_{1-6}$alkoxy, $C_{2-6}$alkenyl and aryl, said alkyl, alkoxy and alkenyl being optionally substituted with 1-3 halo atoms, and said aryl being optionally substituted with 1-3 halo, $C_{1-6}$alkyl, $C_{1-6}$alkoxy, halo$C_{1-6}$alkyl and halo$C_{1-6}$alkoxy groups;

$R^3$ represents H, $C_{1-6}$alkyl;

3 $R^4$ groups are present, 0-3 of which are $C_{1-8}$alkyl, $C_{2-8}$alkenyl, $C_{2-6}$alkynyl or $C_{1-8}$alkoxy groups, said groups being optionally substituted with: (1) 1-5 halo atoms up to perhaloalkyl; (2) 1 oxo group; (3) 1-2 OH groups; (4) 1-2 $C_{1-10}$alkoxy groups, each optionally substituted with up to five halo atoms or a perhaloalkoxy, 1 OH or $CO_2R^a$ group; (5) 1-2 Aryl, Hetcy or HAR groups, each optionally substituted as follows: (i) 1-5 halo atoms, (ii) 1 OH, $CO_2R^a$, CN, $S(O)_p R^d$, $NO_2$ or $C(O)NR^bR^c$ group, (iii) 1-2 $C_{1-10}$alkyl or alkoxy groups, each optionally substituted with: 1-5 halo atoms, up to perhaloalkyl;

and 0-1 of which is Aryl optionally substituted as follows: (1) 1-3 halo atoms; (2) 1-2 OH, $CO_2R^a$, CN or $S(O)_pR^d$ groups; (3) 1-3 $C_{1-8}$alkyl groups optionally substituted with 1-5 halo groups, and (4) 1-3 $C_{1-10}$alkoxy groups, the alkyl portion of which is optionally substituted with 1-5 halo groups, and the remainder are hydrogen atoms;

$R^5$ represents H, halo, $C_{1-6}$ alkyl, $C_{1-6}$alkoxy, halo$C_{1-6}$ alkyl or halo$C_{1-6}$ alkoxy;

G represents —CHR$^x$— wherein R$^x$ represents H or $C_{1-8}$alkyl;

$R^a$ is H or $C_{1-10}$alkyl, optionally substituted with phenyl, OH, O$C_{1-6}$alkyl, $CO_2$H, $CO_2C_{1-6}$alkyl and 1-3 halo groups;

$R^b$ is H or $C_{1-10}$alkyl;

$R^c$ is H or is independently selected from: (a) $C_{1-10}$alkyl, (b) Aryl or Ar—$C_{1-6}$alkyl, each optionally substituted with 1-5 halos and 1-3 members selected from the group consisting of: CN, OH, $C_{1-10}$alkyl and O$C_{1-10}$ alkyl, said alkyl and alkoxy being further optionally substituted with 1-5 halo groups up to perhalo;

$R^d$ is $C_{1-10}$alkyl, Aryl or Ar—$C_{1-10}$alkyl;

p is an integer selected from 0, 1 and 2, and and Z is selected from $CH_2CH_2CO_2R^a$, $CH_2CH(OH)CO_2R^a$ and 5-tetrazolyl.

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, means carbon chains which may be linear, branched or cyclic, or combinations thereof, containing the indicated number of carbon atoms. If no number is specified, 1-10 carbon atoms are intended for linear or branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-10 carbon atoms are intended, forming 1-3 carbocyclic rings that are fused. Examples of cycloalkyl include cyclopropyl, cyclobutyl, cyclopentyl, cyclohexyl, cycloheptyl, decahydronaphthyl and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Aryl" (Ar) means mono- and bicyclic aromatic rings containing 6-12 carbon atoms. Examples of aryl include phenyl, naphthyl, indenyl and the like. Aryl also includes partially aromatic moieties such as tetrahydronaphthyl, indanyl and the like.

"Heteroaryl" (HAR) means a mono- or bicyclic aromatic ring or ring system containing at least one heteroatom selected from O, S and N, with each ring containing 5 to 6 atoms. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl and the like. Heteroaryl also includes aromatic heterocyclic groups fused to heterocycles that are non-aromatic or partially aromatic, and aromatic heterocyclic groups fused to cycloalkyl rings. Heteroaryl also includes such groups in charged form, e.g., pyridinium.

"Heterocyclyl" (Hetcy) means mono- and bicyclic saturated rings and ring systems containing at least one heteroatom selected from N, S and O, each of said ring having from 3 to 10 atoms in which the point of attachment may be carbon or nitrogen. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils). Heterocyclyl moreover includes such moieties in charged form, e.g., piperidinium.

"Halogen" (Halo) includes fluorine, chlorine, bromine and iodine, preferably F and Cl, more preferably F. Haloalkyl and haloalkoxy refer to alkyl and alkoxy groups that are substituted with from 1-5 halo atoms, up to perhalo.

One aspect of the invention is directed to a compound represented by formula I:

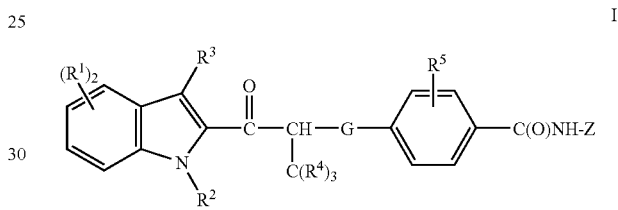

I or a pharmaceutically acceptable salt or solvate thereof, wherein:

each $R^1$ represents H or is independently selected from the group consisting of:

a) OH, halo, $CO_2R^a$, $C(O)NR^bR^c$, $NR^bR^c$, CN or $S(O)_pR^d$; and b) $C_{1-10}$alkyl, $C_{2-10}$alkenyl, O$C_{1-10}$alkyl and O$C_{3-10}$alkenyl, said groups being optionally substituted with: (1) 1-5 halo groups up to a perhaloalkyl group; (2) 1 oxo group; (3) 1-2 OH groups; (4) 1 phenyl ring, which is optionally substituted as follows: 1-5 halo groups up to perhalo, 1-3 $C_{1-10}$alkyl or alkoxy groups, each being further optionally substituted with 1-5 halo up to perhalo;

$R^2$ represents hydrogen or is selected from the group consisting of:

a) $C_{1-14}$alkyl or $C_{2-10}$alkenyl, said alkyl and alkenyl group being optionally substituted with 1-5 halo atoms up to perhalo; 1-2 OH, $S(O)_pR^d$, $C_{1-6}$alkoxy or halo$C_{1-6}$alkoxy groups; and 1-2 Aryl, HAR or Hetcy groups, each optionally substituted with 1-3 halo atoms, 1-4 $C_{1-6}$alkyl groups and 1-2 groups selected from CN, $NO_2$, $S(O)_pR^d$, halo$C_{1-6}$alkyl, $C_{1-6}$alkoxy and halo$C_{1-6}$alkoxy groups; and b) Aryl, HAR or Hetcy, each optionally substituted with 1-3 halo groups and 1-2 groups selected from CN, $NO_2$, $S(O)_pR^d$, $C_{1-6}$alkyl, $C_{1-6}$alkoxy, $C_{2-6}$alkenyl and aryl, said alkyl, alkoxy and alkenyl being optionally substituted with 1-3 halo atoms, and said aryl being optionally substituted with 1-3 halo, $C_{1-6}$alkyl, $C_{1-6}$alkoxy, halo$C_{1-6}$alkyl and halo$C_{1-6}$alkoxy groups;

$R^3$ represents H, $C_{1-6}$alkyl;

3 $R^4$ groups are present, 0-3 of which are $C_{1-8}$alkyl, $C_{2-6}$alkenyl, $C_{2-6}$alkynyl or $C_{1-8}$alkoxy groups, said groups being optionally substituted with: (1) 1-5 halo atoms up to perhaloalkyl; (2) 1 oxo group; (3) 1-2 OH groups; (4) 1-2 $C_{1-10}$alkoxy groups, each optionally substituted with up to five halo atoms or a perhaloalkoxy, 1 OH or $CO_2R^a$ group; (5) 1-2 Aryl, Hetcy or HAR groups, each optionally substituted as follows: (i) 1-5 halo atoms, (ii) 1 OH, $CO_2R^a$, CN, $S(O)_p R^d$, $NO_2$ or $C(O)NR^bR^c$ group, (iii) 1-2 $C_{1-10}$alkyl or alkoxy groups, each optionally substituted with: 1-5 halo atoms, up to perhaloalkyl;

and 0-1 of which is Aryl optionally substituted as follows: (1) 1-3 halo atoms; (2) 1-2 OH, $CO_2R^a$, CN or $S(O)_p R^d$ groups; (3) 1-3 $C_{1-8}$alkyl groups optionally substituted with 1-5 halo groups, and (4) 1-3 $C_{1-10}$alkoxy groups, the alkyl portion of which is optionally substituted with 1-5 halo groups, and the remainder are hydrogen atoms;

$R^5$ represents H, halo, $C_{1-6}$alkyl, $C_{1-6}$alkoxy, halo$C_{1-6}$alkyl or halo$C_{1-6}$alkoxy;

G represents —$CHR^x$— wherein $R^x$ represents H or $C_{1-8}$alkyl;

$R^a$ is H or $C_{1-10}$alkyl, optionally substituted with phenyl, OH, $OC_{1-6}$alkyl, $CO_2H$, $CO_2C_{1-6}$alkyl and 1-3 halo groups;

$R^b$ is H or $C_{1-10}$alkyl;

$R^c$ is H or is independently selected from: (a) $C_{1-10}$alkyl, (b) Aryl or Ar—$C_{1-6}$allyl, each optionally substituted with 1-5 halos and 1-3 members selected from the group consisting of: CN, OH, $C_{1-10}$alkyl and $OC_{1-10}$ alkyl, said alkyl and alkoxy being further optionally substituted with 1-5 halo groups up to perhalo;

$R^d$ is $C_{1-10}$alkyl, Aryl or Ar—$C_{1-10}$alkyl;

p is an integer selected from 0, 1 and 2, and and Z is selected from $CH_2CH_2CO_2R^a$, $CH_2CH(OH)CO_2R^a$ and 5-tetrazolyl.

An aspect of the invention that is of interest relates to a compound of formula I or a pharmaceutically acceptable salt or solvate thereof wherein each $R^1$ is hydrogen or is selected from the group consisting of: halo, $NR^bR^c$, CN, $C_{1-6}$alkyl optionally substituted with 1-3 halo groups, 1 phenyl group or 1 halo substituted phenyl group, and $OC_{1-6}$alkyl, optionally substituted with 1-3 halo groups. Within this subset of the invention, all other variables are as originally defined with respect to formula I.

More particularly, an aspect of the invention that is of interest relates to a compound of formula I or a pharmaceutically acceptable salt or solvate thereof wherein each $R^1$ represents hydrogen or is selected from the group consisting of: halo, $C_{1-6}$alkoxy optionally substituted with 1-3 halo groups, and $C_{1-6}$alkyl optionally substituted with 1-3 halo groups or 1 phenyl ring. Within this subset of the invention, all other variables are as originally defined with respect to formula I.

Even more particularly, an aspect of the invention that is of interest relates to a compound of formula I or a pharmaceutically acceptable salt or solvate thereof wherein each $R^1$ represents hydrogen or is selected from the group consisting of: halo selected from chloro and fluoro, $CF_3$, $OCF_3$, $OCH_3$ and $CH_3$. Within this subset of the invention, all other variables are as originally defined with respect to formula I.

Another aspect of the invention that is of interest relates to a compound of formula I or a pharmaceutically acceptable salt or solvate thereof wherein $R^2$ is hydrogen or is selected from the group consisting of:

a) $C_{1-6}$alkyl or $C_{2-6}$alkenyl, said alkyl and alkenyl being optionally substituted with 1-3 halo atoms; 1-2 $C_{1-6}$alkoxy or halo$C_{1-6}$alkoxy groups; and 1 Aryl or HAR group, each optionally substituted with 1-3 halo atoms, and 1-2 $C_{1-6}$alkyl, CN, $S(O)_p R^d$, halo$C_{1-6}$alkyl, $C_{1-6}$alkoxy and halo$C_{1-6}$ alkoxy groups; and b) Aryl, HAR or Hetcy, each optionally substituted with 1-3 halo atoms and 1-2 groups selected from CN, $S(O)_p R^d$, $C_{1-6}$alkyl, $C_{1-6}$alkoxy, $C_{2-4}$alkenyl and Aryl, said $C_{1-6}$alkyl, $C_{1-6}$alkoxy and $C_{2-4}$alkenyl being optionally substituted with 1-3 halo atoms, and said Aryl being optionally substituted with 1-3 halo atoms and 1-2 $C_{1-6}$alkyl, $C_{1-6}$alkoxy, halo$C_{1-6}$alkyl and halo$C_{1-6}$alkoxy groups. Within this subset of the invention, all other variables are as originally defined with respect to formula I.

More particularly, an aspect of the invention that is of interest relates to a compound of formula I or a pharmaceutically acceptable salt or solvate thereof wherein:

$R^2$ is hydrogen or is selected from the group consisting of:

a) $C_{1-6}$alkyl or $C_{2-3}$alkenyl, said alkyl and alkenyl being optionally substituted with 1-3 halo atoms; 1-2 $C_{1-6}$alkoxy or halo$C_{1-6}$alkoxy groups; and 1 Aryl or HAR group, each optionally substituted with 1-3 halo atoms, and 1-2 $C_{1-6}$alkyl, $C_{1-6}$alkoxy, halo$C_{1-6}$alkyl and halo$C_{1-6}$alkoxy groups; and b) Aryl or HAR, each optionally substituted with 1-3 halo atoms and 1-2 groups selected from CN, $S(O)_p R^d$, $C_{1-6}$alkyl, $C_{1-6}$alkoxy, $C_{2-4}$alkenyl and Aryl, said $C_{1-6}$alkyl, $C_{1-6}$alkoxy and $C_{2-4}$alkenyl being optionally substituted with 1-3 halo atoms, and said Aryl being optionally substituted with 1-3 halo atoms, and 1-2 $C_{1-6}$alkyl, $C_{1-6}$alkoxy, halo$C_{1-6}$alkyl and halo$C_{1-6}$alkoxy groups. Within this subset of the invention, all other variables are as originally defined with respect to formula I.

Even more particularly, an aspect of the invention that is of interest relates to a compound of formula I or a pharmaceutically acceptable salt or solvate thereof wherein: $R^2$ is hydrogen or is selected from the group consisting of:

a) $C_{1-6}$alkyl optionally substituted with 1-3 halo atoms and 1 Aryl or HAR group, each optionally substituted with 1-3 halo atoms selected from Cl and F, and 1-2 $C_{1-6}$alkyl, fluoro-, difluoro- and trifluoro-$C_{1-6}$alkyl, $C_{1-6}$alkoxy, and fluoro-, difluoro- and trifluoro-$C_{1-6}$alkoxy groups; and b) Aryl or pyridyl, each optionally substituted with 1-3 halo groups and 1-2 groups selected from CN, $S(O)_p R^d$, $C_{1-6}$alkyl, $C_{1-6}$alkoxy, $C_{2-4}$alkenyl and Aryl, said $C_{1-6}$alkyl, $C_{1-6}$alkoxy and $C_{2-4}$alkenyl being optionally substituted with 1-3 halo groups, and said Aryl being optionally substituted with 1-3 halo, and 1-2 $C_{1-6}$alkyl, $C_{1-6}$alkoxy, halo$C_{1-6}$alkyl and halo$C_{1-6}$alkoxy groups. Within this subset of the invention, all other variables are as originally defined with respect to formula I.

Another aspect of the invention that is of interest relates to a compound of formula I or a pharmaceutically acceptable salt or solvate thereof wherein $R^3$ represents H or methyl. Within this subset of the invention, all other variables are as originally defined with respect to formula I.

Another aspect of the invention that is of interest relates to a compound of formula I or a pharmaceutically acceptable salt or solvate thereof wherein:

three $R^4$ groups are present, defined as follows: (A) 0-3 $R^4$ groups are $C_{1-6}$alkyl, optionally substituted with: (1) 1-3 halo atoms; (2) 1 OH group; (3) 1 $C_{1-4}$alkoxy group, optionally substituted with up to three halo atoms; (4) 1 Aryl or HAR group, optionally substituted with: (i) 1-3 halo atoms, (ii) 1 OH, $CO_2R^a$, CN, $S(O)_p R^d$ or $C(O)NR^bR^c$ group, and (iii) 1-2 $C_{1-4}$alkyl or alkoxy groups, each optionally substituted with: 1-3 halo atoms;

and (B) 0-1 $R^4$ groups are Aryl optionally substituted as follows: (1) 1-3 halo atoms; (2) 1-2 $C_{1-6}$alkyl groups optionally substituted with 1-3 halo atoms, (3) 1 $C_{1-6}$alkoxy group, the alkyl portion of which is optionally substituted with 1-3 halo atoms, and (4) CN, and the remainder are hydrogen atoms. Within this subset of the invention, all other variables are as originally defined with respect to formula I.

More particularly, another aspect of the invention that is of interest relates to a compound of formula I or a pharmaceutically acceptable salt or solvate thereof wherein:

two $R^4$ groups represent hydrogen, and one $R^4$ is selected from the group consisting of:

(A) $C_{1-6}$alkyl, optionally substituted with: (1) 1-3 halo atoms; (2) 1 OH group; (3) 1 $C_{1-4}$alkoxy group, optionally substituted with up to three halo atoms; (4) 1 Aryl or HAR group, optionally substituted with: (i) 1-3 halo atoms, (ii) 1 OH, $CO_2R^a$, CN, $S(O)_pR^d$ or $C(O)NR^bR^c$ group, and (iii) 1-2 $C_{1-4}$alkyl or alkoxy groups, each optionally substituted with: 1-3 halo atoms; and (B) Aryl optionally substituted with: (1) 1-3 halo atoms; (2) 1 $C_{1-6}$alkyl group optionally substituted with 1-3 halo atoms, (3) 1 $C_{1-6}$alkoxy group, the alkyl portion of which is optionally substituted with 1-3 halo atoms and (4) CN. Within this subset of the invention, all other variables are as originally defined with respect to formula I.

Even more particularly, another aspect of the intention that is of interest relates to a compound of formula I or a pharmaceutically acceptable salt or solvate thereof wherein:

two $R^4$ groups represent hydrogen and one $R^4$ is selected from the group consisting of:

(A) $C_{1-6}$alkyl and (B) Aryl optionally substituted with: (1) 1-3 halo atoms; (2) 1 $C_{1-6}$alkyl group optionally substituted with 1-3 halo atoms (3) 1 $C_{1-6}$alkoxy group, the alkyl portion of which is optionally substituted with 1-3 halo atoms and (4) CN. Within this subset of the invention, all other variables are as originally defined with respect to formula I.

Another aspect of the invention that is of interest relates to a compound of formula I or a pharmaceutically acceptable salt or solvate thereof wherein G represents —$CH_2$— or —$CH(CH_3)$—. Within this subset of the invention, all other variables are as originally defined with respect to formula I.

Another aspect of the invention that is of interest relates to a compound of formula I or a pharmaceutically acceptable salt or solvate thereof wherein $R^5$ represents H, halo, $C_{1-4}$alkyl, halo$C_{1-4}$alkyl, $C_{1-4}$alkoxy or halo$C_{1-4}$alkoxy. Within this subset of the invention, all other variables are as originally defined with respect to formula I.

More particularly, another aspect of the invention that is of interest relates to a compound of formula I or a pharmaceutically acceptable salt or solvate thereof wherein $R^5$ represents H, fluoro, methyl or methoxy. Within this subset of the invention, all other variables are as originally defined with respect to formula I.

Another aspect of the invention that is of interest relates to a compound of formula I or a pharmaceutically acceptable salt or solvate thereof wherein Z is selected from $CH_2CH_2CO_2R^a$ and 5-tetrazolyl. Within this subset of the invention, all other variables are as originally defined with respect to formula I.

More particularly, another aspect of the invention that is of interest relates to a compound of formula I or a pharmaceutically acceptable salt or solvate thereof wherein Z is $CH_2CH_2CO_2R^a$. Within this subset of the invention, all other variables are as originally defined with respect to formula I.

Another aspect of the invention that is of particular interest relates to a compound represented by formula I or a pharmaceutically acceptable salt or solvate thereof, wherein:

$R^1$ is hydrogen or is selected from the group consisting of: halo; $NR^bR^c$; CN; $C_{1-6}$alkyl optionally substituted with 1-3 halo groups; 1 phenyl or halo substituted phenyl group; and $OC_{1-6}$alkyl optionally substituted with 1-3 halo atoms;

$R^2$ is hydrogen or is selected from the group consisting of:

a) $C_{1-6}$alkyl or $C_{2-6}$alkenyl, said alkyl and alkenyl being optionally substituted with 1-3 halo atoms; 1-2 $C_{1-6}$alkoxy or halo$C_{1-6}$alkoxy groups; and 1 Aryl or HAR group, each optionally substituted with 1-3 halo atoms, and 1-2 $C_{1-6}$alkyl, CN, $S(O)_pR^d$, halo$C_{1-6}$alkyl, $C_{1-6}$alkoxy and halo$C_{1-6}$ alkoxy groups; and b) Aryl, HAR or Hetcy, each optionally substituted with 1-3 halo atoms and 1-2 groups selected from CN, $S(O)_pR^d$, $C_{1-6}$alkyl, $C_{1-6}$alkoxy, $C_{2-4}$alkenyl and Aryl, said $C_{1-6}$alkyl, $C_{1-6}$alkoxy and $C_{2-4}$alkenyl being optionally substituted with 1-3 halo atoms, and said Aryl being optionally substituted with 1-3 halo atoms and 1-2 $C_{1-6}$alkyl, $C_{1-6}$alkoxy, halo$C_{1-6}$alkyl and halo$C_{1-6}$alkoxy groups;

$R^3$ represents H or methyl;

three $R^4$ groups are present, defined as follows: (A) 0-3 $R^4$ groups are $C_{1-6}$alkyl, optionally substituted with: (1) 1-3 halo atoms; (2) 1 OH group; (3) 1 $C_{1-4}$alkoxy group, optionally substituted with up to three halo atoms; (4) 1 Aryl or HAR group, optionally substituted with: (i) 1-3 halo atoms, (ii) 1 OH, $CO_2R^a$, CN, $S(O)_pR^d$ or $C(O)NR^bR^c$ group, and (iii) 1-2 $C_{1-4}$alkyl or alkoxy groups, each optionally substituted with: 1-3 halo atoms;

and (B) 0-1 $R^4$ groups are Aryl optionally substituted as follows: (1) 1-3 halo atoms; (2) 1-2 $C_{1-6}$alkyl groups optionally substituted with 1-3 halo atoms, (3) 1 $C_{1-6}$alkoxy group, the alkyl portion of which is optionally substituted with 1-3 halo atoms, and the remainder are hydrogen atoms;

$R^5$ represents H, halo, $C_{1-4}$alkyl, halo$C_{1-4}$alkyl, $C_{1-4}$alkoxy or halo$C_{1-4}$alkoxy;

G represents —$CH_2$— or —$CH(CH_3)$—;

$R^a$ is H or $C_{1-10}$alkyl, optionally substituted with phenyl, OH, $OC_{1-6}$alkyl, $CO_2H$, $CO_2C_{1-6}$alkyl and 1-3 halo groups;

$R^b$ is H or $C_{1-10}$alkyl;

$R^c$ is H or is independently selected from: (a) $C_{1-10}$alkyl, (b) Aryl or Ar—$C_{1-6}$alkyl, each optionally substituted with 1-5 halos and 1-3 members selected from the group consisting of: CN, OH, $C_{1-10}$alkyl and $OC_{1-10}$ alkyl, said alkyl and alkoxy being further optionally substituted with 1-5 halo groups up to perhalo;

$R^d$ is $C_{1-10}$alkyl, Aryl or Ar—$C_{1-10}$alkyl;

p is an integer selected from 0, 1 and 2, and

Z is selected from $CH_2CH_2CO_2R^a$ and 5-tetrazolyl.

More particularly, another aspect of the invention that is of interest relates to a compound represented by formula I, or a pharmaceutically acceptable salt or solvate thereof, wherein:

each $R^1$ represents hydrogen or is selected from the group consisting of: halo, $C_{1-6}$alkoxy optionally substituted with 1-3 halo groups, and $C_{1-6}$alkyl optionally substituted with 1-3 halo groups or 1 phenyl ring;

$R^2$ is hydrogen or is selected from the group consisting of:

a) $C_{1-6}$alkyl or $C_{2-3}$alkenyl, said alkyl and alkenyl being optionally substituted with 1-3 halo atoms; 1-2 $C_{1-6}$alkoxy or halo$C_{1-6}$alkoxy groups; and 1 Aryl or HAR group, each optionally substituted with 1-3 halo atoms, and 1-2 $C_{1-6}$alkyl, $C_{1-6}$alkoxy, halo$C_{1-6}$alkyl and halo$C_{1-6}$alkoxy groups; and b) Aryl or HAR, each optionally substituted with 1-3 halo atoms and 1-2 groups selected from CN, $S(O)_pR^d$, $C_{1-6}$alkyl, $C_{1-6}$alkoxy, $C_{2-4}$alkenyl and Aryl, said $C_{1-6}$alkyl, $C_{1-6}$alkoxy and $C_{2-4}$alkenyl being optionally substituted with 1-3 halo atoms, and said Aryl being optionally substituted with 1-3 halo atoms, and 1-2 $C_{1-6}$alkyl, $C_{1-6}$alkoxy, halo$C_{1-6}$alkyl and halo$C_{1-6}$alkoxy groups;

$R^3$ represents H or methyl;

two $R^4$ groups represent hydrogen, and one $R^4$ is selected from the group consisting of: (A) $C_{1-6}$alkyl, optionally substituted with: (1) 1-3 halo atoms; (2) 1 OH group; (3) 1 $C_{1-4}$alkoxy group, optionally substituted with up to three halo atoms; (4) 1 Aryl or HAR group, optionally substituted with: (i) 1-3 halo atoms, (ii) 1 OH, $CO_2R^a$, CN, $S(O)_pR^d$ or $C(O)NR^bR^c$ group, and (iii) 1-2 $C_{1-4}$alkyl or alkoxy groups, each optionally substituted with: 1-3 halo atoms; and (B) Aryl optionally substituted with: (1) 1-3 halo atoms; (2) 1 $C_{1-6}$alkyl group optionally substituted with 1-3 halo atoms, and (3) 1 $C_{1-6}$alkoxy group, the alkyl portion of which is optionally substituted with 1-3 halo atoms;

$R^5$ represents H, fluoro, methyl or methoxy, and Z is $CH_2CH_2CO_2R^a$. Within this subset of the invention, all other variables are as originally defined with respect to formula I.

Examples of specific compounds that of are particular interest are disclosed throughout the specification.

The invention further includes a pharmaceutical composition which is comprised of a compound of formula I in combination with a pharmaceutically acceptable carrier.

Also included is a method of treating type 2 diabetes mellitus in a mammalian patient in need of such treatment, comprising administering to said patient a compound of formula I in an amount that is effective to treat type 2 diabetes mellitus.

Also included is a method of preventing or delaying the onset of type 2 diabetes mellitus in a mammalian patient in need thereof, comprising administering to said patient a compound of formula I in an amount that is effective to prevent or delay the onset of type 2 diabetes mellitus.

Also included is a method of treating hyperglycemia, diabetes or insulin resistance in a mammalian patient in need of such treatment which comprises administering to said patient an effective amount of a compound of formula I.

Also included is a method of treating, preventing or delaying the onset of diseases or conditions that are associated with type 2 diabetes mellitus. Examples include diseases and conditions selected from the group consisting of: dyslipidemias, (e.g., hyperlipidemia), such as elevated levels of cholesterol (hypercholesterolemia), triglycerides (hypertriglyceridemia) or low density lipoproteins (LDL) (high LDL levels), low levels of high density lipoprotein (HDL), microvascular or macrovascular changes and the sequellae of such conditions, such as coronary heart disease, stroke, peripheral vascular disease, hypertension, renal hypertension, nephropathy, neuropathy and retinopathy. The method entails administering to a type 2 diabetic patient, e.g., a human patient, an amount of a compound of formula I that is effective for treating, preventing or delaying the onset of such diseases or conditions.

Also included is a method of treating atherosclerosis in a mammalian patient in need of such treatment, comprising administering to said patient a compound of formula I in an amount effective to treat atherosclerosis.

Also included is a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient a compound in accordance with formula I in an amount that is effective to treat said condition.

Also included is a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need thereof, comprising administering to the patient a compound of formula I in an amount that is effective to delay the onset of said condition.

Also included is a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound of formula I in an amount that is effective to reduce the risk of developing said condition.

Optical Isomers—Diastereomers—Geometric Isomers—Tautomers

Many of the compounds of formula I contain one or more asymmetric centers and thus occur as racemates and racemic mixtures, single enantiomers, diastereomeric mixtures and individual diastereomers. The present invention includes all such isomeric forms of the compounds, in pure form as well as in mixtures.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Salts and Solvates

The term "pharmaceutically acceptable salts" refers to salts prepared from pharmaceutically acceptable substantially non-toxic bases or acids including inorganic or organic bases and inorganic or organic acids, as well as salts that can be converted into pharmaceutically acceptable salts. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfueric, and tartaric acids.

Solvates as used herein refers to the compound of formula I or a salt thereof, in association with a solvent, such as water. Representative examples include hydrates, hemihydrates, trihydrates and the like.

References to the compounds of Formula I include the pharmaceutically acceptable salts and solvates.

This invention relates to method of antagonizing or inhibiting the production or activity of glucagon, thereby reducing the rate of gluconeogenesis and glycogenolysis, and the concentration of glucose in plasma.

The compounds of formula I can be used in the manufacture of a medicament for the prophylactic or therapeutic treatment of disease states in mammals caused by elevated levels of glucose, comprised of combining the compound of formula I with the carrier materials to provide the medicament.

Dose Ranges

The prophylactic or therapeutic dose of the compound of formula I will, of course, vary with the nature of the condition to be treated, the particular compound selected and its route of administration. It will also vary according to the age, weight and response of the individual patient. In general, the daily dose range lie within the range of from about 0.001 mg to about 100 mg per kg body weight, preferably about 0.01 mg to about 50 mg per kg, and more preferably 0.1 to 10 mg per kg, in single or divided doses. It may be necessary to use dosages outside of these limits in some cases. The terms "effective amount" "anti-diabetic effective amount" and the other terms appearing throughout the application addressing the amount of the compound to be used refer to the dosage ranges provided, taking into account any necessary variation outside of these ranges, as determined by the skilled physician.

Representative dosages for adults range from about 0.1 mg to about 1.0 g per day, preferably about 1 mg to about 200 mg, in single or divided doses.

When intravenous or oral administration is employed, a representative dosage range is from about 0.001 mg to about 100 mg (preferably from 0.01 mg to about 10 mg) of a compound of Formula I per kg of body weight per day, and more preferably, about 0.1 mg to about 10 mg of a compound of Formula I per kg of body weight per day.

Pharmaceutical Compositions

As mentioned above, the pharmaceutical composition comprises a compound of Formula I or a pharmaceutically acceptable salt or solvate thereof and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients. Preferably the composition is comprised of a compound of formula I in an amount that is effective to treat, prevent or delay the onset of type 2 diabetes mellitus, in combination with the pharmaceutically acceptable carrier.

Any suitable route of administration may be employed for providing a mammal, especially a human with an effective dosage of a compound of the present invention. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred. Thus, one aspect of the invention that is of interest is the use of a compound of formula I for preparing a pharmaceutical composition which is comprised of combining the compound of formula I with the carrier.

In preparing oral compositions, any of the usual pharmaceutical media may be employed, such as, for example, water, glycols, oils, alcohols, flavoring agents, preservatives, coloring agents and the like in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets, with the solid oral preparations being preferred. Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 1 g of the active ingredient and each cachet or capsule contains from about 1 to about 500 mg of the active ingredient.

The following are examples of pharmaceutical dosage forms for the compounds of Formula I:

| Injectable Suspension (I.M.) | mg/ mL | Tablet | mg/ tablet |
|---|---|---|---|
| Compound of Formula I | 10.0 | Compound of Formula I | 25 |
| Methylcellulose | 5.0 | Microcrystalline | 415 |
| Tween 80 | 0.5 | Cellulose | |
| Benzyl alcohol | 9.0 | Povidone | 14.0 |
| Benzalkonium chloride | 1.0 | Pregelatinized Starch | 43.5 |
| Water for injection | 1.0 mL | Magnesium Stearate | 2.5 mg |
| to make | | Total | 500 mg |

| Capsule | mg/ capsule | Aerosol | Per canister |
|---|---|---|---|
| Compound of Formula I | 25.0 | Compound of Formula I | 24 mg |
| Lactose Powder | 573.5 | Lecithin, NF Liq. Conc. | 1.2 mg |
| Magnesium Stearate | 1.5 | Trichlorofluoro- | 4.025 g |
| Total | 600 mg | methane, NF | |
| | | Dichlorodifluoro -methane, NF | 12.15 g |

Combination Therapy

Compounds of Formula I may be used in combination with other drugs that are used in the treatment/prevention/delaying the onset of type 2 diabetes mellitus, as well as the diseases and conditions associated with type 2 diabetes mellitus, for which compounds of Formula I are useful. Other drugs may be administered, by a route and in an amount commonly used therefor, contemporaneously or sequentially with a compound of Formula I. When a compound of Formula I is used with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (a) bis-guanides (e.g., buformin, metformin, phenformin), (b) PPAR agonists (e.g., troglitazone, pioglitazone, rosiglitazone), (c) insulin, (d) somatostatin, (e) alpha-glucosidase inhibitors (e.g., voglibose, miglitol, acarbose), (f) DP-IV inhibitors, (g) LXR modulators and (h) insulin secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide).

The weight ratio of the compound of the Formula I to the second active ingredient may be varied within wide limits and depends upon the effective dose of each ingredient. Generally, an effective dose of each will be used. Thus, for example, when a compound of the Formula I is combined with a PPAR agonist the weight ratio of the compound of the Formula I to the PPAR agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

For combination products, the compound of formula I may be combined with any other active ingredients and then added to the carrier ingredients; alternatively the order of mixing may be varied.

Examples of pharmaceutical combination compositions include: 1) a compound according to formula I, 2) a compound selected from the group consisting of: a) DP-IV inhibitors; b) insulin sensitizers selected from the group consisting of (i) PPAR agonists and (ii) biguanides; c) insulin and insulin mimetics; d) sulfonylureas and other insulin secretagogues; e) alpha glucosidase inhibitors; f) glucagon receptor antagonists; g) GLP-1, GLP-1 mimetics, and GLP-1 receptor agonists; h) GIP, GIP mimetics, and GIP receptor agonists; i) PACAP, PACAP mimetics, and PACAP receptor 3 agonists; j) cholesterol lowering agents selected from the group consisting of (i) HMG-CoA reductase inhibitors, (ii) sequestrants, (iii) nicotinyl alcohol, nicotinic acid or a salt thereof, (iv) PPAR alpha agonists, (v) PPAR alpha/gamma dual agonists, (vi) inhibitors of cholesterol absorption, (vii) acyl CoA:cholesterol acyltransferase inhibitors, (viii) anti-oxidants and (ix) LXR modulators; (k) PPAR delta agonists; (I) antiobesity compounds; (m) an ileal bile acid transporter inhibitor; (n) anti-inflammatory agents other than glucocorticoids; and (o) protein tyrosine phosphatase-1B (PTP-1B) inhibitors; and 3) a pharmaceutically acceptable carrier.

A method that is of particular interest relates to a method of treating, preventing or delaying the onset of diabetes, and in particular, type 2 diabetes, in a mammalian patient in need thereof, comprising administering to the patient 1) a compound according to formula I, and 2) a compound selected from the group consisting of: a) DP-IV inhibitors; b) insulin sensitizers selected from the group consisting of (i) PPAR agonists and (ii) biguanides; c) insulin and insulin mimetics; d) sulfonylureas and other insulin secretagogues; e) alpha glucosidase inhibitors; f) glucagon receptor antagonists; g) GLP-1, GLP-1 mimetics, and GLP-1 receptor agonists; h) GIP, GIP mimetics, and GIP receptor agonists; i) PACAP, PACAP mimetics, and PACAP receptor 3 agonists; j) cholesterol lowering agents selected from the group consisting of (i) HMG-CoA reductase inhibitors, (ii) sequestrants, (iii) nicotinyl alcohol, nicotinic acid or a salt thereof, (iv) PPAR alpha agonists, (v) PPAR alpha/gamma dual agonists, (vi) inhibitors of cholesterol absorption, (vii) acyl CoA:cholesterol acyltransferase inhibitors, (viii) anti-oxidants and (ix) LXR modulators; (k) PPAR delta agonists; (1) antiobesity compounds; (m) an ileal bile acid transporter inhibitor; (n) anti-inflammatory agents other than glucocorticoids; and (o) protein tyrosine phosphatase-1B (PTP-1B) inhibitors; said compounds being administered in an amount that is effective to treat, prevent or delay the onset of type 2 diabetes.

In accordance with the methods described herein one method that is of interest relates to a method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient an effective amount of a compound of formula I and a compound selected from the group consisting of: (a) DP-IV inhibitors; (b) insulin sensitizers selected from the group consisting of (i) PPAR agonists and (ii) biguanides; (c) insulin and insulin mimetics; (d) sulfonylureas and other insulin secretagogues; (e) alpha glucosidase inhibitors; (f) glucagon receptor antagonists; (g) GLP-1, GLP-1 mimetics, and GLP-1 receptor agonists; (h) GIP, GIP mimetics, and GIP receptor agonists; (i) PACAP, PACAP mimetics, and PACAP receptor 3 agonists; (j) cholesterol lowering agents selected from the group consisting of: (i) HMG-CoA reductase inhibitors, (ii) sequestrants, (iii) nicotinyl alcohol, nicotinic acid and salts thereof, (iv) PPAR alpha agonists, (v) PPARalpha/gamma dual agonists, (vi) inhibitors of cholesterol absorption, (vii) acyl CoA:cholesterol acyltransferase inhibitors, (viii) anti-oxidants and (ix) LXR modulators; (k) PPAR delta agonists; (l) antiobesity compounds; (m) an ileal bile acid transporter inhibitor; (n) anti-inflammatory agents excluding glucocorticoids; and (o) protein tyrosine phosphatase-1B (PTP-1B) inhibitors, said compounds being administered to the patient in an amount that is effective to treat said condition.

More particularly, a method that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalina patient in need of such treatment, comprising administering to the patient a therapeutically effective amount of a compound of formula I and an HMG-CoA reductase inhibitor.

Even more particularly, the method that is of interest comprises administering to the patient a therapeutically effective amount of a compound of formula I and an HMG-CoA reductase inhibitor wherein the HMG-CoA reductase inhibitor is a statin, and even more particularly, the statin is selected from the group consisting of lovastatin, simvastatin, pravastatin, fluvastatin, atorvastatin, itavastatin, ZD-4522 and rivastatin.

A different aspect of the invention relates to a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment a therapeutically effective amount of a compound of formula I and an HMG-CoA reductase inhibitor.

Another aspect of the invention relates to a method for delaying the onset or reducing the risk of developing atherosclerosis in a human patient in need of such treatment comprising administering to said patient an effective amount of a compound of formula I and an HMG-CoA reductase inhibitor. More particularly, the method comprises administering an effective amount of a compound of formula I and an HMG-CoA reductase inhibitor wherein the HMG-CoA reductase inhibitor is a statin. Even more particularly, the method comprises administering a compound of formula I and a statin selected from the group consisting of: lovastatin, simvastatin, pravastatin, fluvastatin, atorvastatin, itavastatin, ZD-4522 and rivastatin. Still more particularly, the method comprises administering a compound of formula I and the statin known as simvastatin.

Another aspect of the invention relates to a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment a therapeutically effective amount of a compound of formula I and a cholesterol absorption inhibitor. In particular, the method comprises administering an effective amount of a compound of formula I and the cholesterol absorption inhibitor known as ezetimibe.

More particularly, a method for delaying the onset or reducing the risk of developing atherosclerosis in a human patient in need of such treatment is described which comprises administering to said patient an effective amount of a compound of formula I and a cholesterol absorption inhibitor. More particularly, the method comprises administering a compound of formula I and the cholesterol absorption inhibitor known as ezetimibe.

Throughout the specification, the following abbreviations are used with the following meanings unless otherwise indicated:

| | |
|---|---|
| Bu = butyl, t-Bu = t-butyl | Bn and Bnzl = benzyl |
| BOC, Boc = t-butyloxycarbonyl | CBZ, Cbz = Benzyloxycarbonyl |
| DABCO = | iPrOH = isopropanol |
| 1,4-diazabicyclo[2.2.2]octane | DCM = dichloromethane |
| DCC = Dicyclohexylcarbodiimide | DMF = N,N-dimethylformamide |
| DIEA = diisopropylethylamine | EDC = 1-ethyl-3-(3-dimethyl- |
| DMSO = dimethylsulfoxide | aminopropyl)-carbodiimide |
| DIAD = diisopropylazodicarboxylate | Et = ethyl |
| DMAP = 4-Dimethylaminopyridine | EtOH = ethanol |
| EtOAc = ethyl acetate | FAB-mass spectrum = Fast atom |
| eq. = equivalent(s) | bombardment-mass spectroscopy |
| HOAc = acetic acid | HPLC = High pressure liquid |
| LCMS = high pressure liquid | chromatography |
| chromatography mass spectrometry | LAH = Lithium aluminum hydride |
| HOBT, HOBt = Hydroxybenztriazole | Pt/C = platinum on activated |
| LHMDS = lithium | carbon |
| bis(trimethylsilyl)amide | PBS = phosphate buffered saline |
| Me = methyl | KHMDS = potassium |
| Ph = phenyl | bis(trimethylsilyl)amide |
| THF = Tetrahydrofuran | TFA = Trifluoroacetic acid |
| $C_6H_{11}$ = cyclohexyl | TMS = Trimethylsilane |
| iPr, $^i$Pr = isopropyl | $NMe_2$ = dimethylamino |
| 2,4-diClPh = 2,4-dichlorophenyl | 2ClPh = 2-chlorophenyl |
| | Py, Pyr = pyridyl |
| | PyBOP = Benzotriazol-1-yloxytripyrrolidinophosphonium hexafluorophosphate |

Compounds of the present invention may be prepared according to the methodology outlined in the following general synthetic schemes, where $R^1$—$R^5$, G and Z are defined as above, and P=methyl, ethyl or tert-butyl.

In one embodiment of the present invention, the compounds I may be prepared from 2-carboxyindoles 1. 2-Carboxyindoles are commercially available, known in the literature or may be conveniently prepared by a variety of methods by those skilled in the art. For example, as shown in Scheme 1, reaction of the appropriate 2-iodoaniline 19 with pyruvic acid in the presence of a metal catalyst such as palladium acetate, a base such as 1,4-diazabicyclo[2.2.2]octane (DABCO) and dehydrating agent such as magnesium sulfate in a solvent such as N,N-dimethylformamide (DMF) at elevated temperatures for 2 to 48 h provides the desired 2-carboxyindole as described in *J. Org. Chem.*, 1997, 62, 2676. In another example shown in Scheme 1,2-carboxyindoles may be prepared by treatment of the 2-H indole 20 with a base such as n-butyllithium in an aprotic solvent such as THF or mixed solvent such as THF and hexanes at −78° C., followed by introduction of $CO_2$ and reaction for 10 min to 1 h. Concentration in vacuo, resuspension in an aprotic solvent such as THF and cooling of the resultant solution to −78° C., followed by addition of a base such as t-butyllithium, introduction of $CO_2$ and reaction at −78° C. for 1 to 8 h provides the 2-carboxyindole, as described in *Tetrahedron Lett.*, 1985, 26, 5935.

Scheme 1

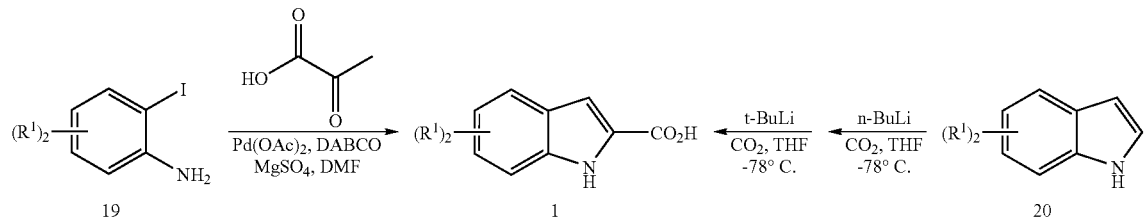

Compounds I may be prepared starting from carboxylic acid 1 as depicted in Scheme 2. Carboxylic acid 1 may be converted to the amide 2 by reaction with N,O-dimethylhydroxylamine in presence of a coupling reagent such as 1-ethyl-3-(3-dimethylaminopropyl)-carbodiimide (EDC) and 1-hydroxybenzotriazole (HOBt) and a base, generally diisopropylethylamine (DIEA), in a solvent such as DMF or methylene chloride for 1 to 24 h at ambient or slightly elevated temperatures. Such Weinreb amides are known to undergo reaction with alkyllithium compounds in aprotic solvents such as THF or a mixture of solvents such as THF and hexanes to form the corresponding ketones, as described in *J.* *Org. Chem.,* 1991, 56, 3750. Thus, dropwise addition of a solution of alkyllithium compound $(R^4)_3CCH_2Li$ in an aprotic solvent such as hexanes to a solution of the Weinreb amide 2 in an aprotic solvent such as THF cooled to −78° C., followed by reaction for 1-8 h affords ketone 3.

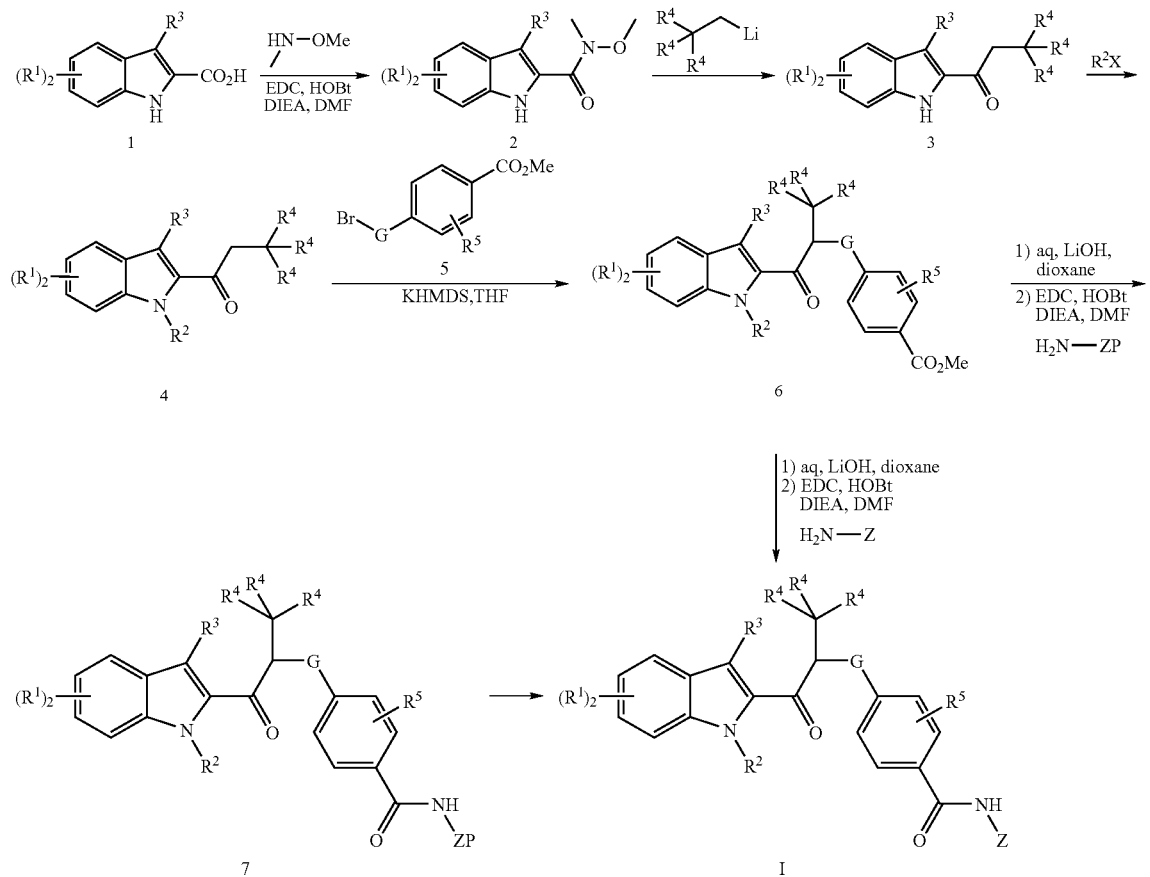

The indole nitrogen may then be elaborated by reaction with $R^2X$ (X=I, Br and OH) using various conditions known by those skilled in the art to provide intermediate 4. For example, when $R^2$=alkyl or benzyl, reaction of ketoindole 3 with $R^2X$ (X=I or Br) in presence of a base such as NaH in a polar aprotic solvent such as DMF or THF at ambient or elevated temperatures for 1-24 h provides the N-derivatized compound 4. Additionally, when $R^2$=alkyl or benzyl, N-substitution of 3 to provide 4 may also be undertaken by reaction with R²OH in presence of a phosphine such as Ph₃P and an azodicarboxylate such as diisopropyl azodicarboxylate in an aprotic solvent such as dichloromethane or toluene at ambient or elevated temperatures for 1-24 h. When R²=aryl or heteroaryl, N-arylation of indole 3 may be performed by reaction with R²X (X=I or Br) in presence of a metal catalyst such as CuI, a ligand such as 1,2-trans-N,N'-dimethylcyclohexanediamine and a base such as potassium phosphate in a solvent such as toluene at elevated temperatures to afford 4, as described in *J. Am. Chem. Soc.*, 2002, 124, 11684.

Reaction of the N-substituted indole 4 in an aprotic solvent such as toluene or THF or a mixture of such solvents cooled to −78° C. with a base such as potassium bis-(trimethylsilyl) amide (KHMDS), followed by addition of benzyl bromide 5 and reaction at reduced or ambient temperatures affords the benzylated product 6. If so desired, the enantiomers of 6, subsequent intermediates, or final compound I may be separated by chromatography using a homochiral stationary phase by methods known to those skilled in the art.

Saponification of the ester 6 may be achieved using a base such as aqueous lithium or sodium hydroxide in a polar solvent such as tetrahydrofuran, dioxane, methanol, ethanol or a mixture of similar solvents. The acid may then be elaborated with the appropriate amine using a coupling reagent such as 1-ethyl-3-(3-dimethylaminopropyl)-carbodiimide (EDC) and 1-hydroxybenzotriazole (HOBt), or benzotriazol-1-yloxytrispyrrolidinophosphonium hexafluorophosphate (PyBOP) and a base, generally diisopropylethylamine, in a solvent such as N,N-dimethylformamide (DMF) or methylene chloride for 1 to 48 h at ambient temperature. Coupling of 1H-tetraazol-5-amine monohydrate provides compound I directly, whereas coupling of an amino ester gives protected amide 7. Removal of the ester to provide compound I when P=Me, Et or tert-butyl is readily accomplished by treatment with a base such as aqueous lithium or sodium hydroxide in a polar solvent such as tetrahydrofuran, dioxane, methanol, ethanol or a mixture of similar solvents at ambient or elevated temperatures. Additionally, when P is a tert-butyl group it is conveniently removed by treatment with an acid such as trifluoroacetic acid, commonly as a 1:1 mixture with methylene chloride, for 0.5-8 h at ambient temperature. As will be known to those skilled in the art, in all schemes, the product I and all synthetic intermediates may be purified from unwanted side products by recrystallization, trituration, preparative thin layer chromatography, flash chromatography on silica gel as described by W. C. Still et al, *J. Org. Chem.*, 1978, 43, 2923, or reverse-phase HPLC. Compounds purified by HPLC may be isolated as the corresponding salt.

In some cases, the product I, the penultimate ester 7 or the benzoate ester 6 from the reactions described in the scheme will be further modified. These manipulations may include, but are not limited to substitution, reduction, oxidation, alkylation, acylation, and hydrolysis reactions, which are commonly known to those skilled in the art. For example, as shown in Scheme 3, when R²=ArBr (compound 6b), the aryl ring may be further elaborated with various groups including, but not limited to, alkyl, alkenyl, aryl or heteroaryl by reaction with the corresponding boronic acid R—B(OH)₂ in the presence of a catalyst such as palladium acetate and ligand such as tri-o-tolylphosphine and a base such as cesium carbonate in a solvent such as toluene at elevated temperatures to provide intermediate 6c.

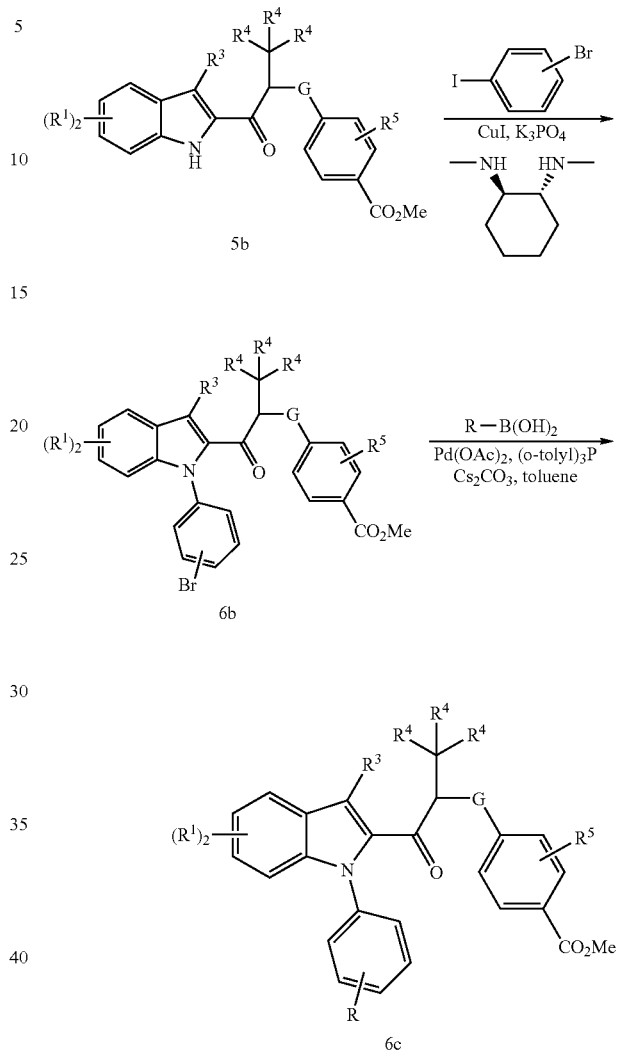

When R²=benzyl, another route to compound I may be used, involving deprotection of the indole nitrogen to provide a late-stage intermediate which may be elaborated with a variety of R² groups, as shown in Scheme 4. Thus, starting from N-benzyl intermediate 6d, the N-benzyl group may be removed using a Lewis acid such as AlCl₃ in a solvent such as benzene or a mixture of solvents such as benzene and anisole to provide compound 8, as described in *Synthesis*, 1984, 9, 738 and *J. Chem Soc., Perkin Trans* 1, 1988, 3005. If so desired, the enantiomers of 8, subsequent intermediates, or final compound I may be resolved by chromatography using a homochiral stationary phase. The indole nitrogen of intermediate 8 may then be elaborated with a variety of R² groups by reaction with R²X (X=I, Br or OH) to provide intermediate 6, as described in Scheme 2 (vide supra). Hydrolysis of the methyl ester and attachment of 1H-tetraazol-5-amine monohydrate to provide compound I, or attachment of an aminoester H₂N-ZP to give intermediate 7, followed by deprotection to provide compound I, can be carried out as described in Scheme 2 (vide supra).

Scheme 4

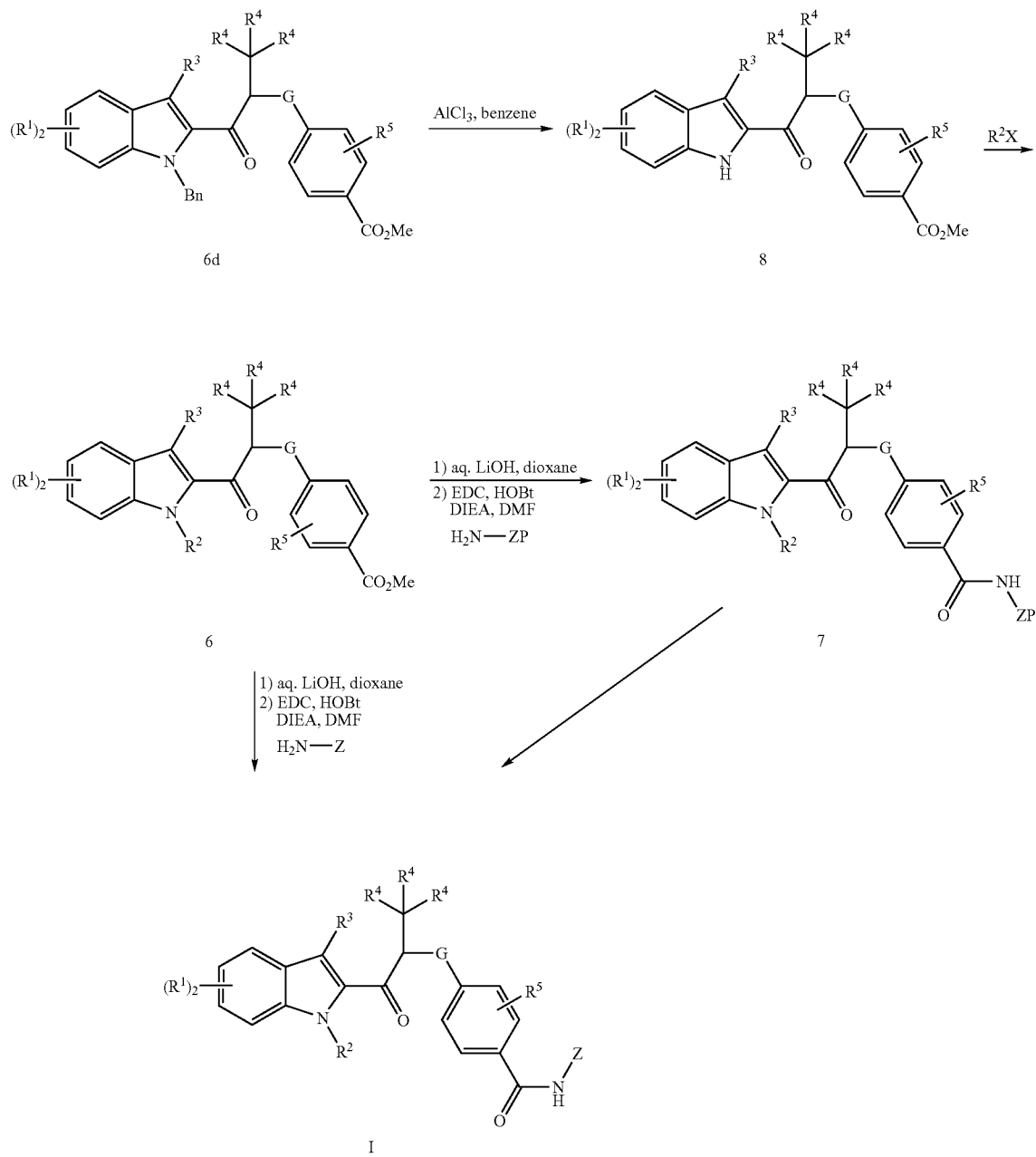

Products I may also be prepared from amide intermediate 9 as shown in Scheme 5. Compound 9 may be readily obtained by saponification of ester 8 using a base such as aqueous lithium or sodium hydroxide in a polar solvent such as tetrahydrofuran, dioxane, methanol, ethanol or a mixture of similar solvents, followed by coupling of the amine $H_2N$-ZP using a coupling reagent such as 1-ethyl-3-(3-dimethylaminopropyl)-carbodiimide (EDC) and 1-hydroxybenzotriazole (HOBt), or benzotriazole-1-yloxytrispyrrolidinophosphonium hexafluorophosphate (PyBOP) and a base, generally diisopropylethylamine, in a solvent such as N,N-dimethylformamide (DMF) or methylene chloride for 0.5 to 24 h at ambient temperature. If so desired, the enantiomers of 9, subsequent intermediates, or final compound I can be resolved by chromatography using a homochiral stationary phase.

The indole nitrogen of 9 may then be elaborated using $R^2X$ (X=I, Br or OH) to provide 7, as described in Scheme 2 (vide supra). When P=Me, Et or tert-butyl, removal of the ester to provide compound I is readily accomplished using a base such as aqueous lithium or sodium hydroxide in a polar solvent such as tetrahydrofuran, dioxane, methanol, ethanol or a mixture of similar solvents. Additionally, when P is a tert-butyl group it is conveniently removed by treatment with an acid such as trifluoroacetic acid, often as a 1:1 mixture with methylene chloride, for 0.5-8 h at ambient temperature.

Scheme 5

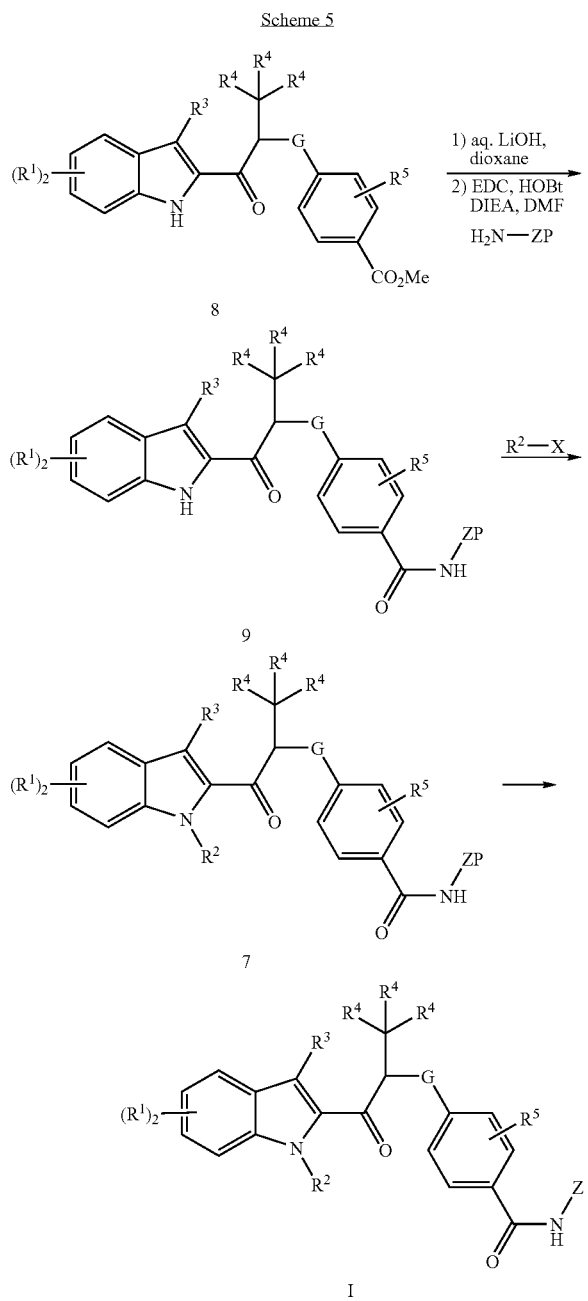

The compounds I may also be accessed according to Scheme 6. Indole-2-carboxylic esters 10 are commercially available, known in the literature or may be conveniently prepared from the corresponding 2-carboxylic acid by those skilled in the art. Modification of the indole nitrogen with $R^2X$ (X=I, Br or OH) to yield intermediate 11 may then be undertaken as described in Scheme 2 (vide supra).

The ester 11 may be converted to the β-keto ester 12 by reaction with tert-butylacetate in the presence of base such as lithium bis-(trimethylsilyl)amide (LHMDS) in an aprotic solvent such as THF at −78° C. The ketoester 12 may then be converted to the ketone 4 by alkylation with $(R^4)_3CX$ (X=I or Br) in the presence of a base such as NaH in a polar aprotic solvent such as DMF or THF at ambient or elevated temperatures for 1-24 h, followed by decarboxylation of the β-ketoester by removal of the tert-butyl group by treatment with an acid such as TFA, commonly as a 1:1 mixture with dichloromethane for 0.5-16 h, then heating of the resultant β-ketoacid in a solvent such as benzene. Reaction of the N-substituted indole 4 in an aprotic solvent such as toluene or THF or a mixture of such solvents cooled to −78° C. with a base such as potassium bis-(trimethylsilyl)amide (KHMDS), followed by addition of benzyl bromide 5 and reaction at reduced or ambient temperatures affords the benzylated product 6. Hydrolysis of the methyl ester of 6 and attachment of 1H-tetraazol-5-amine monohydrate to provide compound I, or attachment of an aminoester $H_2N$-ZP to give intermediate 7, followed by cleavage of the ester to provide compound I, can be carried out as described in Scheme 2 (vide supra).

Scheme 6

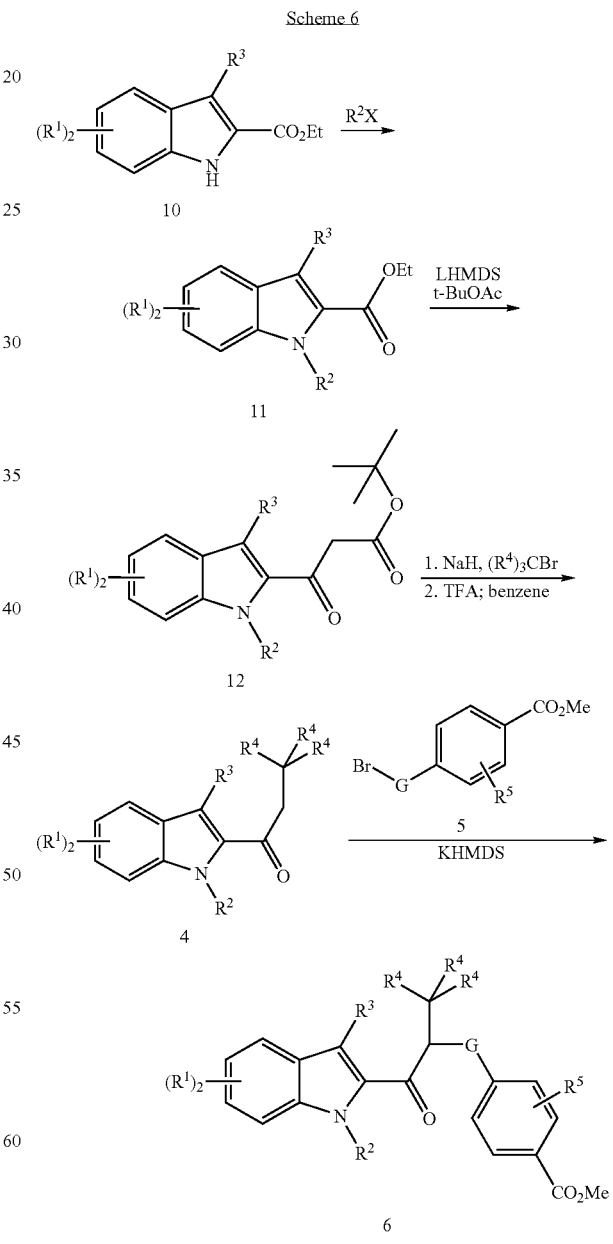

The compounds I may also be constructed from the β-ketoester 12 in a different order, as depicted in Scheme 7. Thus, ketoester 12 may be benzylated with bromide 5 in the presence of NaH in a solvent such as DMF at ambient temperature for 1 to 16 h. Decarboxylation of the β-ketoester may be accomplished by removal of the tert-butyl group by treatment with an acid such as TFA, commonly as a 1:1 mixture with dichloromethane, for 0.5 to 8 h, then heating of the resultant β-ketoacid in a solvent such as benzene to afford ketone 13. Reaction of 13 with $(R^4)_3CX$ (X=I or Br) in the presence of a base such as KHMDS in an aprotic solvent such as THF affords ester intermediate 6. Further elaboration of ester 6 to provide compound I may be performed as described in Scheme 2 (vide supra).

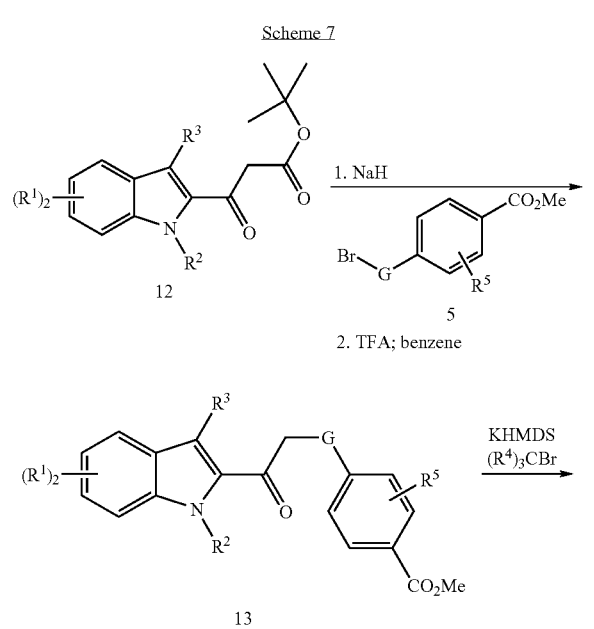

Compounds I may also be prepared from β-ketoester intermediate 12 by the route shown in Scheme 8. Alkylation of 12 with the desired $(R^4)_3CX$ (X=I or Br) using a base such as NaH in a polar solvent such as DMF at elevated temperatures for 1 to 24 h, followed by reaction with benzyl bromide 5 in the presence of a base such as NaH in a solvent such as DMF at ambient or elevated temperatures for 1 to 24 h provides β-ketoester 14. Decarboxylation of 14 to afford 6 may be accomplished by removal of the tert-butyl group by treatment with an acid such as TFA, commonly as a 1:1 mixture with dichloromethane, for 0.5-8 h, followed by heating of the resultant β-ketoacid in a solvent such as benzene. Further elaboration of ester 6 to provide compound I may be undertaken as described in Scheme 2 (vide supra).

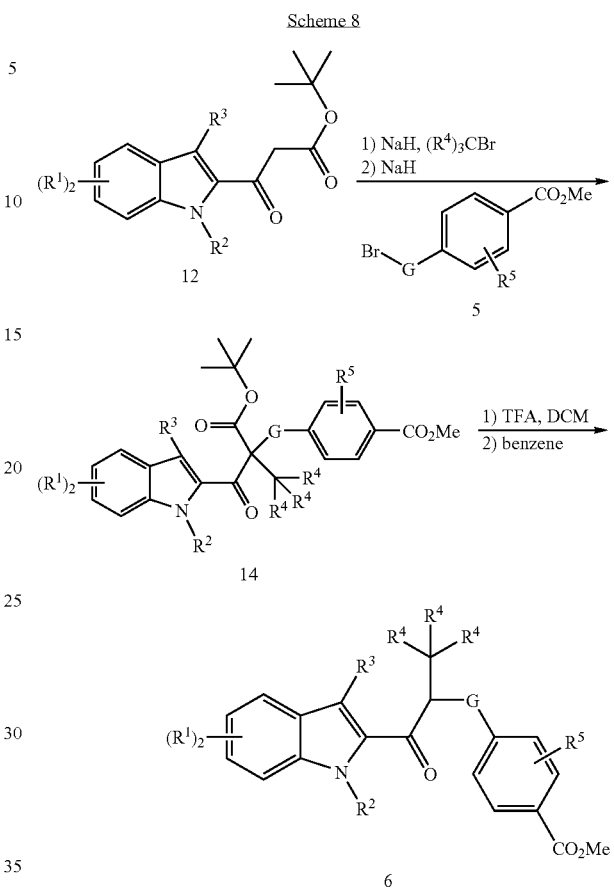

An additional procedure for preparing compounds I is outlined in Scheme 9. Treatment of $(R^4)_3CCH_2CO_2Me$ with a base such as LHMDS in an aprotic solvent such as THF at −78° C., followed by addition of indole ester 11 and warming to 0° C., provides β-ketoester intermediate 15. Decarboxylation of the β-ketoester may be accomplished by heating in the presence of LiCl in a mixture of DMSO and $H_2O$ at 140° C. for 2 to 24 h as described in *J. Org. Chem.*, 1998, 63, 7213. Treatment of resultant indole 4 with a base such as KHMDS in an aprotic solvent such as THF at −78° C., followed by addition of benzyl bromide 5 and reaction at −78° C. to ambient temperature for 2 to 24 h affords the benzylated intermediate 6. Further elaboration of ester 6 to provide compound I may be undertaken as described in Scheme 2 (vide supra).

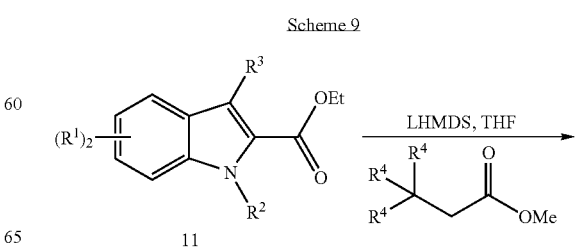

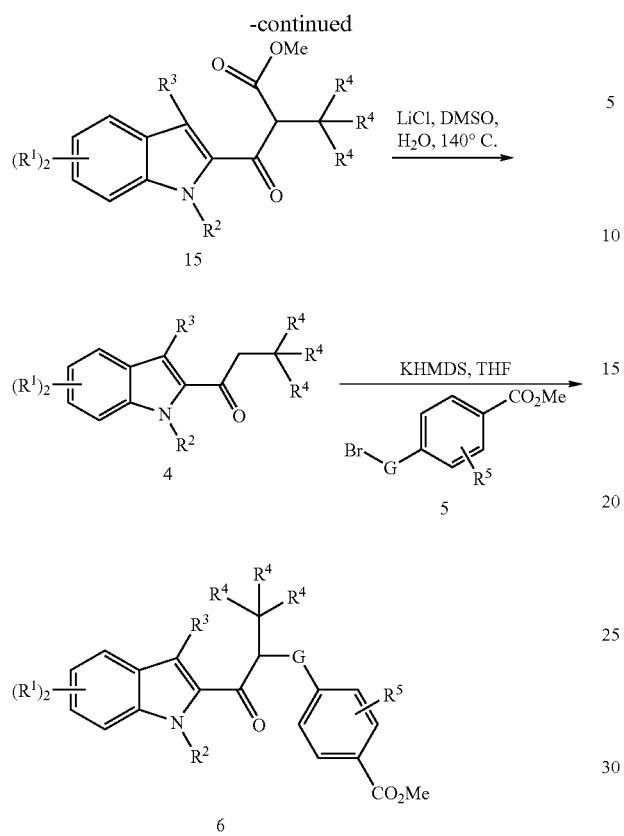

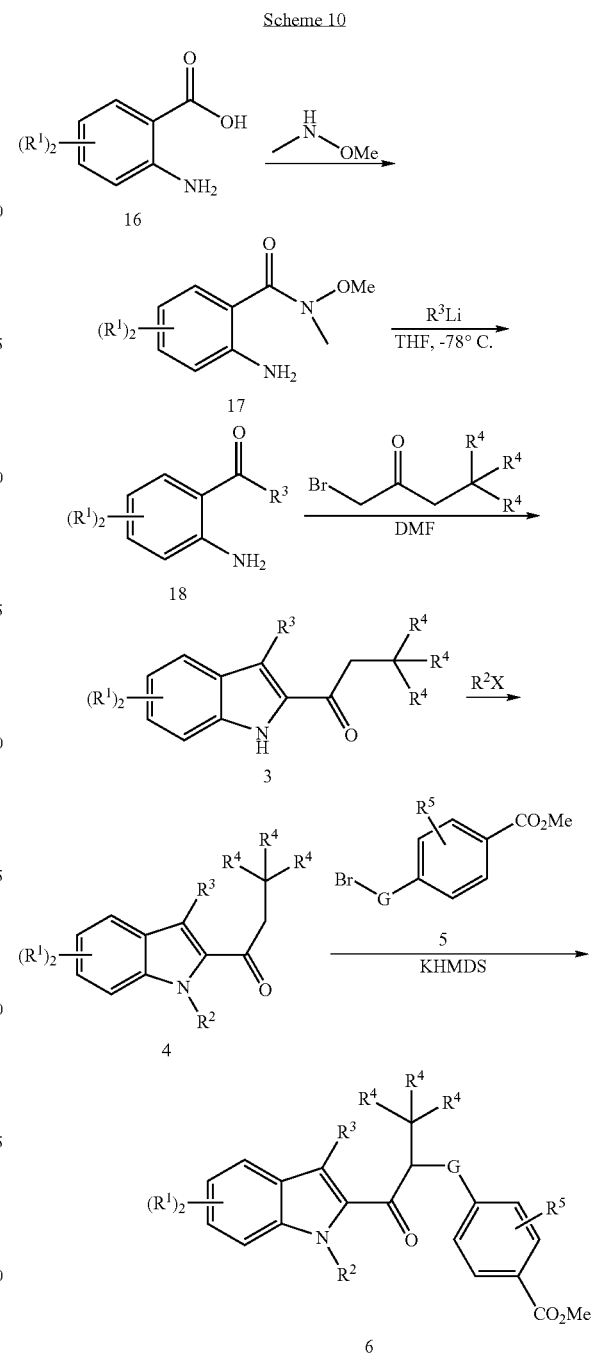

Compounds I may also be prepared according to Scheme 10. 2-Aminobenzoic acids 16 are commercially available, known in the literature or may be conveniently prepared by a variety of methods by those skilled in the art. The carboxylic acid may be converted to the Weinreb amide 17 by reaction with N,O-dimethylhydroxylamine in presence of a coupling reagent such as 1-ethyl-3-(3-dimethylaminopropyl)-carbodiimide (EDC) and 1-hydroxybenzotriazole (HOBt) and a base such as diisopropylethylamine (DIEA), in a solvent such as N,N-dimethylformamide (DMF) or methylene chloride for 1 to 24 h at ambient or slightly elevated temperatures. Dropwise addition of the appropriate alkyllithium compound R³Li in a solvent such as hexanes or ether to a solution of the Weinreb amide 17 in an aprotic solvent such as THF cooled to −78° C., followed by stirring for 1-8 h affords ketone 18, as described in *J. Org. Chem.*, 1991, 56, 3750. Reaction of 18 with the desired α-bromoketone BrCH₂C(O)CH₂C(R⁴)₃ in a solvent such as DMF at elevated temperatures for 2 to 24 h, according to the method described in *J. Org. Chem.*, 1972, 37, 3622, provides the 2-ketoindole 3. Elaboration of the indole nitrogen by reaction with R²X (X=I, Br or OH), as described in Scheme 2 (vide supra), provides intermediate 4. Reaction of the N-substituted indole 4 in an aprotic solvent such as toluene or THF or a mixture of such solvents cooled to −78° C. with a base such as potassium bis-(trimethylsilyl)amide (KHMDS), followed by addition of benzyl bromide 5 and reaction at reduced or ambient temperatures affords the benzylated product 6. Further modification of intermediate 6 to obtain compound I can be undertaken as described in Scheme 2 (vide supra).

General Experimental: Chemical reactions were monitored by LC-MS, and the purity and identity of the reaction products were assayed by LC-MS according to the following conditions:

Method A (LCMS A): Column: Waters Xterra C18 (3.0×50 mm). Gradient: 10-100% CH₃CN (containing 0.05% TFA)/H₂O (containing 0.06% TFA) over 3.75 min (1 mL/min Method B (LCMS B): Column: MetaChem Polaris (4.6×50 mm). Gradient: 5-95% CH₃CN/H₂O, (both with 0.05% TFA) over 2.5 min @ 2.5 mL/min Method C (LCMS C): Column: Waters Xterra C18 (3.0×50 mm). Gradient: 10-98% $CH_3CN$ (containing 0.05% TFA)/$H_2O$ (containing 0.06% TFA) over 3.25 min @ 1.5 mL/min Method D (LCMS D): Column: Waters Xterra C18 (3.0×50 mm). Gradient: 10-98% $CH_3CN$ (containing 0.05% TFA)/$H_2O$ (containing 0.06% TFA) over 1.25 min @ 1.5 mL/min Method E (LCMS E): Column: Waters Xterra C18 (3.0×50 mm). Gradient: 10-100% MeCN (containing 0.05% formic acid)/$H_2O$ (containing 0.06% formic acid) over 3.75 min @ 1 mL/min Preparative HPLC was performed on either a YMC-Pack Pro C18 column (150×20 mm i.d.) or a Kromasil 100-10C8 column (100×30 mm i.d.) at an initial flow rate of 4 mL/min for 1.35 min, followed by 20 mL/min for 10.6 min. The gradients employed during the faster part of the run are described, and all runs were followed with 100% organic at 20 mL/min for 0.5 min.

Flash chromatography on silica gel was performed using pre-packed silica gel columns on a Biotage Horizon or Biotage SP-1 instrument equipped with a UV detector.

The following examples are provided so that the invention might be more fully understood. They should not be construed as limiting the invention in any way.

Preparation of many of the intermediates that are used in the synthesis of the Examples is described below.

INTERMEDIATE 1

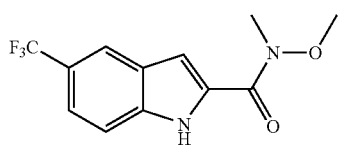

N-Methoxy-N-methyl-5-(trifluoromethyl)-1H-indole-2-carboxamide

To a flask containing 2-iodo-4-trifluoromethylaniline (5.66 g, 19.7 mmol) were added pyruvic acid (4.17 mL, 59.2 mmol), DABCO (6.68 g, 59.2 mmol), magnesium sulfate (3.56 g, 29.6 mmol), and palladium acetate (443 mg, 1.97 mmol). The mixture was purged with $N_2$ and dry DMF (60 mL) was added. The resultant suspension was deoxygenated via $N_2$-sparge for 15 min, then was capped and placed in a 105° C. bath. After 48 h, the mixture was allowed to cool to room temperature. The insoluble materials were filtered and the filtrate was diluted with EtOAc. The organic phase was washed ($H_2O$, then 1 N HCl), dried over anhydrous $Na_2SO_4$, and concentrated in vacuo: LCMS E, $t_r$=2.95 min, m/z 228.1 [M–H]. To a flask containing the crude product obtained above were added EDC (8.0 g, 42.0 mmol), HOBt (5.67 g, 42.0 mmol) and N,O-dimethylhydroxylamine hydrochloride (4.10 g, 42.0 mmol). The resultant mixture was dissolved in DMF (30 mL), DIEA (11.8 mL, 67 mmol) was added, and the reaction mixture was stirred at 50° C. for 18 h. The mixture was then allowed to cool to room temperature and was quenched by pouring into sat. aq. $NaHCO_3$. The aqueous phase was extracted with EtOAc (2×) and the combined organic phases were concentrated in vacuo. Purification by flash chromatography on silica gel (20 to 40%, then 40 to 100% EtOAc in hexanes) provided the title compound: LCMS B, $t_r$=2.08 min, m/z 273.1 [M+H]$^+$. $^1$H NMR (500 MHz, $CDCl_3$) δ 9.67 (br s, 1H), 8.02 (s, 1H), 7.52 (d, J=1.0 Hz, 2H), 7.31 (d, J=2.0 Hz, 1H), 3.86 (s, 3H), 3.46 (s, 3H).

INTERMEDIATE 2

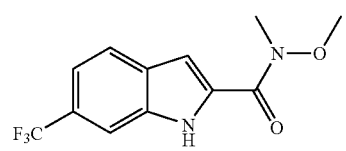

N-Methoxy-N-methyl-6-(trifluoromethyl)-1H-indole-2-carboxamide

To cooled (–78° C.) solution of 6-trifluoromethyl indole (1.44 g, 7.77 mmol) in THF (10 mL) was added n-BuLi (5.1 mL, 1.6 M in hexanes, 8.2 mmol). After 30 min, a stream of dry $CO_2$ (Aldrich lecture bottle) was bubbled through the mixture for 10 min. The resultant mixture was held at –78° C. for a further 10 min, then was concentrated in vacuo. The resultant solid was dissolved in THF (10 mL), cooled to –78° C., and t-BuLi (4.8 mL, 1.7 M in pentane, 8.2 mmol) was added. After 1 h, a stream of dry $CO_2$ was bubbled through the reaction mixture for 10 min. After an additional 1 h at –78° C., the mixture was quenched with $H_2O$ and allowed to warm to room temperature. The mixture was diluted with EtOAc, then poured into a mixture of sat. aq. $NH_4Cl$ and 1 N HCl (1:1). The phases were separated, and aqueous phase was extracted with EtOAc. The combined organic phases were dried over $Na_2SO_4$ and concentrated in vacuo. To a flask containing the crude product obtained above were added EDC (2.97 g, 15.5 mmol), HOBt (2.10 g, 15.5 mmol), N,O-dimethylhydroxylamine hydrochloride (1.52 g, 15.5 mmol). The resultant mixture was dissolved in DMF (20 mL), DIEA (6.9 mL, 39 mmol) was added, and the reaction mixture was stirred at 50° C. for 18 h. The mixture was quenched by addition of sat. aq. $NaHCO_3$. The aqueous phase was extracted with EtOAc and the organic phase was concentrated in vacuo. Purification by flash chromatography on silica gel (10 to 60%, then 60 to 100% EtOAc in hexanes) provided the title compound: LCMS A, $t_r$=3.23 min, m/z 273.2 [M+H]$^+$; $^1$H NMR (500 MHz, $CDCl_3$) δ 9.67 (s, 1H), 7.79 (d, J=8.5 Hz, 1H), 7.75 (s, 1H), 7.36 (d, J=9.0 Hz, 1H), 7.28 (s, 1H), 3.87 (s, 3H), 3.46 (s, 3H).

EXAMPLE 1

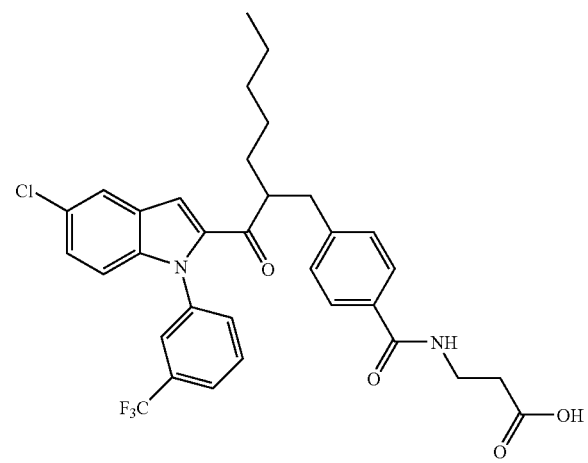

Step A. 5-Chloro-N-methoxy-N-methyl-1H-indole-2-carboxamide

To a flask containing 5-chloroindole-2-carboxylic acid (8.33 g, 42.6 mmol) were added EDC (12.6 g, 63.9 mmol), HOBt (8.63 g, 63.9 mmol), N,O-dimethylhydroxylamine hydrochloride (6.23 g, 63.9 mmol) sequentially. N,N-Dimethylformamide (100 mL) was added, followed by DIEA (22.6 mL, 128 mmol), and the resulting solution was stirred at 40° C. for 18 h. The reaction mixture was allowed to cool to room temperature, then was poured into saturated aqueous sodium bicarbonate and extracted with ethyl acetate. The combined organic phases were dried over anhydrous sodium sulfate and concentrated in vacuo. The resulting amide was taken forward without further purification: LCMS B, $t_r$=2.03 min, m/z 239.1 [M+H]$^+$; $^1$H NMR (500 MHz, CDCl$_3$) δ 9.55 (s, 1H), 7.66 (d, J=2.0 Hz, 1H), 7.37 (d, J=8.5 Hz, 1H), 7.24 (dd, J=8.5, 2.0 Hz, 1H), 7.16 (s, 1H), 3.85 (s, 3H), 3.44 (s, 3H).

Step B. 1-(5-Chloro-1H-indol-2-yl)heptan-1-one

To a cooled (−78° C.) solution of the title compound of Example 1 Step A (ca. 42.6 mmol) in THF (100 mL) was added n-hexyllithium (74 mL, 2.3 M in hexanes, 170.4 mmol) dropwise. The mixture was stirred at −78° C. for 2 h, then was quenched by addition of 2 N aqueous hydrochloric acid. The resulting suspension was allowed to warm to room temperature, then was extracted with ethyl acetate. The organic phase was concentrated in vacuo. Purification by flash chromatography on silica gel (10% EtOAc in hexanes) provided the title compound: LCMS B, $t_r$=2.70 min, m/z 264.2 [M+H]$^+$; $^1$H NMR (500 MHz, CDCl$_3$) δ 9.37 (br s, 1H), 7.68 (d, J=2.0 Hz, 1H), 7.37 (d, J=9.0 Hz, 1H), 7.29 (dd, J=9.0, 2.0 Hz, 1H), 7.13 (s, 1H), 2.94 (t, J=7.5 Hz, 2H), 1.78 (quint., J=7.5 Hz, 2H), 1.43-1.29 (m, 6H), 0.89 (t, J=7.0 Hz, 3H).

Step C. 1-{5-Chloro-1-[3-(trifluoromethyl)phenyl]-1H-indol-2-yl}heptan-1-one To a vial containing the title compound of Example 1 Step B (3.0 g, 11.36 mmol), were added 3-iodobenzotrifluoride (1.97 mL, 13.6 mmol), copper iodide (218 mg, 1.14 mmol), potassium phosphate (5.05 g, 23.9 mmol), and 1,2-trans-N,N-dimethylcyclohexane diamine (0.718 mL, 4.54 mmol). The reaction mixture was placed under a nitrogen atmosphere, and anhydrous toluene (11.4 mL, deoxygenated via nitrogen sparge) was added. The vial was then capped and placed in a pre-heated oil bath (110° C.) and stirred rapidly for 19 h. The mixture was allowed to cool to room temperature, then was filtered. The supernatant was washed extensively with EtOAc, and the organic phase was concentrated in vacuo. Purification by flash chromatography (10% EtOAc in hexanes) afforded the title compound: LCMS B, $t_r$=3.02 min, m/z 408.2 [M+H]$^+$; $^1$H NMR (500 MHz, CDCl$_3$) δ 7.74-7.72 (m, 2H), 7.64 (t, J=8.0 Hz, 1H), 7.52 (s, 1H), 7.46 (d, J=8.0 Hz, 1H), 7.37 (s, 1H), 7.26 (dd, J=9.0, 2.0 Hz, 1H), 6.96 (d, J=9.0 Hz, 1H), 2.94 (t, J=7.5 Hz, 2H), 1.68 (quint., J=7.5 Hz, 2H), 1.38-1.28 (m, 6H), 0.88 (t, J=7.0 Hz, 3H).

Step D. Methyl 4-[(2RS)-({5-chloro-1-[3-(trifluoromethyl)phenyl]-1H-indol-2-yl}carbonyl)heptyl]benzoate To a cooled (−78° C.) solution of the title compound of Example 1 Step C (2.0 g, 4.90 mmol) in THF (25 mL), was added KHMDS (19.6 mL, 0.5 M in toluene, 9.80 mmol). After 30 min, a solution of methyl 4-bromomethylbenzoate (2.24 g, 9.80 mmol) in THF (5 mL) was added, dropwise. After 2 h, the mixture was removed from the −78° C. bath, and allowed to warm slowly to room temperature. After 2 h at room temperature, the reaction mixture was quenched by addition of saturated aq. NaHCO$_3$. The aqueous phase was extracted twice with ethyl acetate, and the combined organic phases were dried over anhydrous sodium sulfate, then concentrated in vacuo. The crude product was taken forward without further purification. A small portion was removed and purified by reverse phase HPLC (70 to 100% CH$_3$CN in H$_2$O, each with 0.1% v/v TA) for characterization: LCMS C, $t_r$=3.15 min, m/z 556.4 [M+H]$^+$; $^1$H NMR (500 MHz, CDCl$_3$) δ 7.93 (d, J=8.0 Hz, 2H), 7.75 (d, J=8.0 Hz, 1H), 7.71 (d, J=2.0 Hz, 1H), 7.65 (app t, J=8.0 Hz, 1H), 7.41 (br s, 1H), 7.29 (s, 1H), 7.28 (d, J=2.0 Hz, 1H), 7.26-7.24 (m, 1H obscured by residual CHCl$_3$)), 7.24 (d, J=8.0 Hz, 2H), 6.94 (d, J=8.5 Hz, 1H), 3.90 (s, 3H), 3.65 (dddd, J=8.5, 8.5, 5.5, 5.5 Hz, 1H), 3.07 (dd, J=13.5, 8.5 Hz, 1H), 2.85 (dd, J=13.5, 6.0 Hz, 1H), 1.83-1.76 (m, 1H), 1.61-1.56 (m, 1H), 1.37-1.27 (m, 6H), 0.88 (t, J=7.0 Hz, 3H).

Step E. tert-Butyl 3-({4-[(2SR)-2-({5-chloro-1-[3-(trifluoromethyl)phenyl]-1H-indol-2-yl}carbonyl)heptyl]phenyl}carbonyl)amino]propanoate The title compound of Example 1 Step D (ca. 4.90 mmol) was dissolved in 1,4-dioxane (20 mL), LiOH (12 mL, 2 N aqueous, 24 mmol) was added, and the mixture was stirred at 40° C. for 15 h. The mixture was then quenched by addition of 2 N aqueous hydrochloric acid, and the aqueous phase was extracted with ethyl acetate. The combined organic phases were dried over anhydrous sodium sulfate and concentrated in vacuo. To a flask containing the crude carboxylic acid were added EDC (2.81 g, 14.7 mmol), HOBt (1.98 g, 14.7 mmol), β-alanine tert-butyl ester hydrochloride (2.66 g, 14.7 mmol), DMF (10 mL) and DIEA (5.2 mL, 29.4 mmol). The mixture was stirred at 50° C. for 1 h, then was poured into saturated aqueous NaHCO$_3$. The aqueous phase was extracted with ethyl acetate, and the combined organic phases were concentrated in vacuo. Purification by flash chromatography on silica gel (0 to 40%, then 40 to 100% EtOAc in hexanes) provided the title compound: LCMS B, $t_r$=3.02 min, m/z 669.3 [M+H]$^+$; $^1$H NMR (500 MHz, CDCl$_3$) δ 7.73 (d, J=8.0 Hz, 1H), 7.68 (d, J=2.0 Hz, 1H), 7.64-7.61 (m, 3H), 7.40-7.30 (m, 2H), 7.25 (d, J=2.0 Hz, 1H), 7.23 (s, 1H), 7.20 (d, J=8.0 Hz, 2H), 6.92 (d, J=9.0 Hz, 1H), 6.80 (t, J=5.5 Hz, 1H), 4.05-4.00 (m, 1H), 3.64 (q, J=6.0 Hz, 2H), 3.64-3.58 (m, 1H), 3.04 (dd, J=13.5, 9.0 Hz, 1H), 2.80 (dd, J=13.5, 6.0 Hz, 1H), 2.52 (t, J=6.0 Hz, 2H), 1.80-1.72 (m, 1H), 1.58-1.51 (m, 2H) 1.44 (s, 9H), 1.26-1.21 (m, 5H), 0.84 (t, J=7.0 Hz, 3H).

Step F. 3-({4-[(2S)-2-({5-chloro-1-[3-(trifluoromethyl)phenyl]-1H-indol-2-yl}carbonyl)heptyl]benzoyl}amino)propanoic acid and 3-({4-[(2R)-2-({5-chloro-1-[3-(trifluoromethyl)phenyl]-1H-indol-2-yl}carbonyl)heptyl]benzoyl}amino)propanoic acid Chiral HPLC purification of the title compound of Example 1 Step E (ChiralCel AD-H column, 10% iPrOH in n-heptane, 9 mL/min flow rate) provided two isomers, $t_r$=23.4 min and $t_r$=30.7 min. Each amide (676 mg, 1.02 mmol) was separately dissolved in CH$_2$Cl$_2$ (10 mL) and TFA (10 mL), and the mixtures were stirred at room temperature for 45 min. The volatiles were removed in vacuo. Purification by reverse phase HPLC (70 to 100% CH$_3$CN in H$_2$O, each with 0.1% v/v TFA) provided the title compounds. The following data are for the more potent glucagon receptor antagonist, which is derived from the first eluting tert-butyl ester enantiomer: LCMS C, $t_r$=2.74 min, m/z 613.2 [M+H]$^+$; $^1$H NMR (500 MHz, d$_6$-DMSO) δ 8.40 (t, J=5.5 Hz, 1H), 7.88 (d, J=2.0 Hz, 1H), 7.85 (d, J=8.0 Hz, 1H), 7.76 (s, 1H), 7.69 (d, J=8.0 Hz, 2H), 7.53-7.46 (br m, 2H), 7.32 (dd, J=9.0, 2.0 Hz, 2H), 7.27 (d, J=8.0 Hz, 2H), 7.01 (d, J=9.0 Hz, 1H), 3.87-3.81 (m, 1H), 2.93 (dd, J=14.0, 8.3 Hz, 1H), 2.76 (dd, J=14.0, 6.3 Hz, 1H), 2.47 (t, J=7.0 Hz, 2H), 1.65-1.58 (m, 1H), 1.48-1.42 (m, 1H), 1.27-1.18 (m, 6H), 0.79 (t, J=7.0 Hz, 3H), α-NH β-alanine methylene group obscured by residual H$_2$O signal; $[α]_D^{20}$=+15.2 (c 1, EtOH). Data for the less potent glucagon receptor antagonist, which is derived from the second eluting tert-butyl ester enantiomer: LCMS C, $t_r$=2.74 min, m/z 613.2 [M+H]$^+$; $^1$H NMR (500 MHz, d$_6$-DMSO) δ 8.40 (t, J=5.5 Hz, 1H), 7.88 (d, J=2.0 Hz, 1H), 7.85 (d, J=8.0 Hz, 1H), 7.76 (s, 1H), 7.69 (d, J=8.0 Hz, 2H), 7.53-7.46 (br m, 2H), 7.32 (dd, J=9.0, 2.0 Hz, 2H), 7.27 (d, J=8.0 Hz, 2H), 7.01 (d, J=9.0 Hz, 1H), 3.87-3.81 (m, 1H), 3.40 (q, J=7.0 Hz, 2H), 2.93 (dd, J=14.0, 8.3 Hz, 1H), 2.76 (dd, J=14.0, 6.3 Hz, 1H), 2.47 (t, J=7.0 Hz, 2H), 1.65-1.58 (m, 1H), 1.48-1.42 (m, 1H), 1.27-1.18 (m, 6H), 0.79 (t, J=7.0 Hz, 3H); $[α]_D^{20}$=−13.3 (c 0.12, EtOH).

EXAMPLE 2

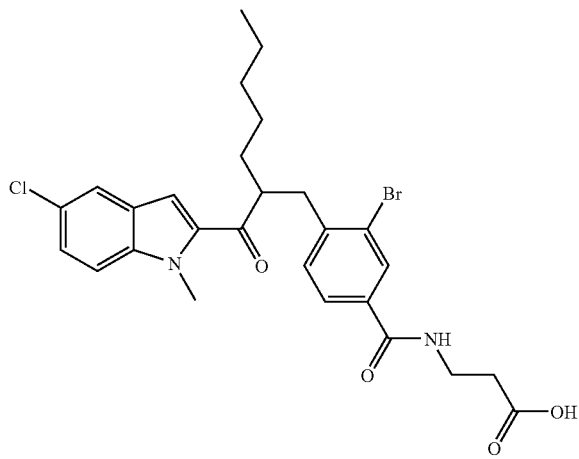

Step A. Methyl 3-bromo-4-(bromomethyl)benzoate

To a solution of methyl 3-bromo-4-methyl benzoate (4.20 g, 18.3 mmol) in CCl$_4$ (36 mL) were added N-bromosuccinimide (3.26 g, 18.3 mmol) and 2,2'-azo-bisisobutyronitrile (300.0 mg, 1.84 mmol). The resultant mixture was stirred at 90° C. for 18 h, then was allowed to cool to room temperature. The reaction mixture was filtered and concentrated in vacuo. Purification by flash chromatography on silica gel (0 to 5%, then 5 to 100% EtOAc in hexanes) afforded the title compound: $^1$H NMR (500 MHz, CDCl$_3$) δ 8.28 (d, J=1.5 Hz, 1H), 7.99 (dd, J=8.0, 1.5 Hz, 1H), 7.57 (d, J=8.0 Hz, 1H), 4.65 (s, 2H), 3.97 (s, 3H).

Step B. 1-(5-Chloro-1-methyl-1H-indol-2-yl)heptan-1-one

To a solution of the title compound of Example 1 Step B (98.0 mg, 0.37 mmol) in DMF was added NaH (15.0 mg, 60% suspension in mineral oil, 0.37 mmol). After 10 min, iodomethane (0.023 mL, 0.37 mmol) was added, and the mixture was stirred for 2 h, whereupon it was quenched by addition of sat. aq. NaHCO$_3$. The aqueous phase was extracted with EtOAc, and the organic phase was concentrated in vacuo. Purification by flash chromatography on silica gel (0 to 10%, then 10 to 100% EtOAc in hexanes) provided the title compound: LCMS C, $t_r$=2.78 min, m/z 278.3 [M+H]$^+$; $^1$H NMR (500 MHz, CDCl$_3$) δ 7.65 (app t, J=1.0 Hz, 1H), 7.31 (d, J=1.0 Hz, 2H), 7.20 (s, 1H), 4.05 (s, 3H), 2.95 (t, J=7.0 Hz, 2H), 1.79-1.72 (m, 2H), 1.43-1.26 (m, 6H), 0.90 (t, J=7.5 Hz, 3H).

Step C. Methyl 3-bromo-4-{(2RS)-2-[(5-chloro-1-methyl-1H-indol-2-yl)carbonyl]heptyl}benzoate To a cooled (−78° C.) solution of the title compound of Example 1 Step B (161 mg, 0.58 mmol) in THF (3 mL) was added KHMDS (2.30 mL, 0.5 M in toluene, 1.15 mmol). After 30 min, a solution of the title compound of Example 2 Step A (357.0 mg, 1.16 mmol) in THF (3 mL) was added, and the resultant mixture was allowed to warm slowly to room temperature over 15 h. The mixture was then quenched by addition of sat. aq. NaHCO$_3$, and the aqueous phase was extracted with EtOAc. The organic phase was dried over anhydrous Na$_2$SO$_4$, and concentrated in vacuo. The crude product was taken forward without further purification. A small portion was removed and purified by reverse phase HPLC (85 to 100% CH$_3$CN in H$_2$O, both with 0.1% v/v TFA) for characterization: LCMS C, $t_r$=3.12 min, m/z 506.2 [M+H]$^+$; $^1$H NMR (500 MHz, CDCl$_3$) δ 8.19 (d, J=1.5 Hz, 1H), 7.79 (dd, J=8.0, 2.0 Hz, 1H), 7.63 (d, J=1.5 Hz, 1H), 7.33-7.25 (m, 3H), 7.11 (s, 1H), 4.02 (s, 3H), 3.89 (s, 3H), 3.83 (dddd, J=9.0, 9.0, 6.0, 6.0 Hz, 1H), 3.21 (dd, J=13.5, 9.0 Hz, 1H), 3.06 (dd, J=13.5, 6.0 Hz, 1H), 1.91-1.83 (m, 2H), 1.63-1.56 (m, 1H), 1.39-1.26 (m, 5H), 0.86 (t, J=6.5 Hz, 3H).

Step D. 3-[(3-Bromo-4-{(2S)-2-[(5-chloro-1-methyl-1H-indol-2-yl)carbonyl]heptyl}benzoyl)amino]propanoic acid and 3-[(3-Bromo-4-{(2R)-2-[(5-chloro-1-methyl-1H-indol-2-yl)carbonyl]heptyl}benzoyl)amino]propanoic acid To a solution of the title compound of Example 2 Step C (ca. 0.58 mmol) in 1,4-dioxane (2 mL) was added a solution of LiOH (50.0 mg, 2.10 mmol) in H$_2$O (2 mL), and the resultant mixture was stirred at 50° C. for 2 h. The mixture was allowed to cool to room temperature whereupon it was quenched by the addition of 2 N aq. HCl. The aqueous phase was extracted with EtOAc, and the organic phase was dried over Na$_2$SO$_4$ and concentrated in vacuo. To the crude carboxylic acid obtained above were added EDC (213 mg, 1.12 mmol), HOBt (150 mg, 1.12 mmol), and β-alanine tert-butyl ester hydrochloride (202 mg, 1.12 mmol). The resultant mixture was dissolved in DMF (2 mL), DIEA (0.643 mL, 3.63 mmol) was added, and the reaction mixture was stirred at 50° C. for 4 h. The reaction mixture was quenched by addition of sat. aq. NH$_4$Cl, and the aqueous phase was extracted with EtOAc. The organic phase was concentrated in vacuo. Purification by flash chromatography on silica gel (0 to 50%, then 50 to 100% EtOAc in hexanes) provided the title compound as a racemic mixture. Chiral HPLC purification (ChiralCel OD column, 10% iPrOH in heptane, 9 mL/min) provided two isomers, $t_r$=19.2 min and $t_r$=21.8 min. Each amide was separately dissolved in CH$_2$Cl$_2$ (1 mL) and TFA (1 mL). After 30 min, the mixtures were concentrated in vacuo. Purification by reverse phase HPLC (75 to 100% CH$_3$CN in H$_2$O, each with 0.1% v/v TFA) provided the title compounds. The following data are for the more potent glucagon receptor antagonist, which is derived from the second eluting tert-butyl ester enantiomer: LCMS A, t$_r$=4.17 min, m/z 563.4 [M+H]$^+$; $^1$H NMR (500 MHz, d$_6$-DMSO) δ 8.54 (t, J=5.5 Hz, 1H), 7.99 (d, J=1.5 Hz, 1H), 7.77 (d, J=2.0 Hz, 1H), 7.66 (dd, J=8.0, 2.0 Hz, 1H), 7.58 (d, J=9.0 Hz, 1H), 7.40 (s, 1H), 7.38 (d, J=8.0 Hz, 1H), 7.34 (dd, J=9.0, 2.0 Hz, 1H), 3.94 (s, 3H), 3.86-3.81 (m, 1H), 3.10 (dd, J=13.5, 8.0 Hz, 1H), 2.94 (dd, J=13.5, 6.0 Hz, 1H), 1.75-1.69 (m, 1H), 1.51-1.44 (m, 1H), 1.27-1.16 (m, 6H), 0.77 (t, J=7.0.Hz, 3H), β-alanine methylene protons obscured by residual H$_2$O and DMSO signals.

EXAMPLE 3

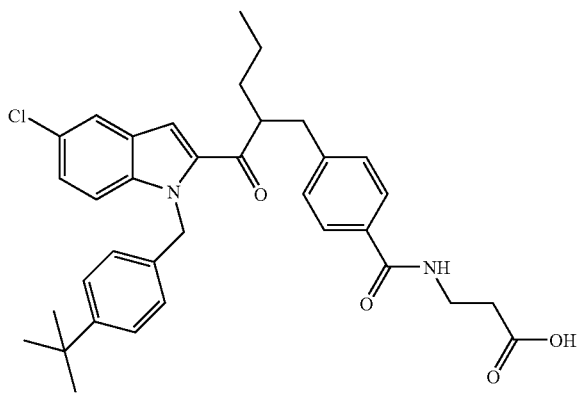

Step A. 1-(5-Chloro-1H-indol-2-yl)pentan-1-one

To a cooled (−78° C.) solution of the title compound of Example 1 Step A (2.40 g, 10.1 mmol) in THF (30 mL) was added n-BuLi (15.7 mL, 1.6 M in hexanes, 25.1 mmol), and the mixture was stirred for 1.5 h, whereupon it was transferred to a 0° C. bath. After 45 min, the reaction mixture was quenched by addition of 2 N aq. HCl. The aqueous phase was extracted with EtOAc, and the organic phase was dried over anhydrous Na$_2$SO$_4$ and concentrated in vacuo. Purification by flash chromatography on silica gel (0 to 25%, then 25 to 100% EtOAc in hexanes) provided the title compound: LCMS A, t$_r$=3.74 min, m/z 236.1 [M+H]$^+$; $^1$H NMR (500 MHz, CDCl$_3$) □9.34 (br s, 1H), 7.68 (d, J=2.0 Hz, 1H), 7.37 (d, J=8.5 Hz, 1H), 7.29 (dd, J=8.5, 1.5 Hz, 1H), 7.13 (d, J=1.5 Hz, 1 H), 2.95 (t, J=7.5 Hz, 2H), 1.80-1.74 (m, 2H), 1.47-1.40 (m, 2H), 0.97 (t, J=7.5 Hz, 3H).

Step B. 1-[5-Chloro-1-(phenylmethyl)-1H-indol-2-yl]pentan-1-one

To a solution of the title compound of Example 3 Step A (1.35 g, 5.73 mmol) in DMF (25 mL) was added NaH (252 mg, 60% suspension if mineral oil, 6.30 mmol). After 20 min, benzyl bromide (0.750 mL, 6.30 mmol) was added, and the mixture was allowed to stir for 15 h, whereupon it was quenched by addition of sat. aq. NH$_4$Cl. The aqueous phase was extracted with EtOAc, and the organic phase was dried over Na$_2$SO$_4$ and concentrated in vacuo. Purification by flash chromatography on silica gel (0 to 15%, then 15 to 100% EtOAc in hexanes) provided the title compound: LCMS A, t$_r$=4.36 min, m/z 326.2 [M+H]$^+$; $^1$H NMR (500 MHz, CDCl$_3$) δ 7.74 (d, J=1.0 Hz, 1H), 7.34-7.22 (m, 6 H), 7.04 (d, J=7.0 Hz, 2H), 5.88 (s, 2H), 2.99 (t, J=7.5 Hz, 2H), 1.76-1.70 (m, 2H), 1.44-1.36 (m, 2 H), 0.97 (t, J=7.0 Hz, 3H).

Step C. Methyl 4-{(2RS)-2-[(1-benzyl-5-chloro-1H-indol-2-yl)carbonyl]pentyl}benzoate To a cooled (−78° C.) solution of the title compound of Example 3 Step B (1.50 g, 4.61 mmol) in THF (20 mL) was added KHMDS (13.8 mL, 0.5 M in toluene, 6.90 mmol). After 25 min, a solution of methyl 4-bromomethyl benzoate (1.27 g, 5.54 mmol) in THF (5 mL) was added, and the resultant mixture was allowed to warm slowly to room temperature over 4 h. The reaction mixture was then poured into sat. aq. NH$_4$Cl, and the aqueous phase was extracted with EtOAc. The organic phase was dried over anhydrous Na$_2$SO$_4$ and concentrated in vacuo: LCMS A, t$_r$=4.52 min, m/z 474.2 [M+H]$^+$; $^1$H NMR (500 MHz, CDCl$_3$) δ 7.84 (d, J=8.0 Hz, 2 h), 7.64-7.63 (m, 1H), 7.27-7.25 (m, 3H), 7.22-7.19 (m, 2H), 7.15 (d, J=8.0 Hz, 2H), 7.14 (s, 1H), 5.80 (ABq, J=16.0 Hz, Δv=61.8 Hz, 2H), 3.87 (s, 3H), 3.63-3.59 (m, 1H), 3.07 (dd, J=13.5, 8.5 Hz, 1H), 2.77 (dd, J=13.5, 6.0 Hz, 1H), 1.74-1.69 (m, 1H), 1.53-1.45 (m, 1H), 1.23-1.18 (m, 2H), 0.82 (t, J=7.5 Hz, 3H).

Step D. Methyl 4-{(2RS)-2-[(5-chloro-1H-indol-2-yl)carbonyl]pentyl}benzoate

To flask containing AlCl$_3$ (1.57 g, 11.7 mmol) was added a solution of the title compound of Example 3 Step C (1.39 g, 2.94 mmol) in benzene (8.0 mL). After 1 h, the reaction mixture was quenched by addition of sat. aq. NH$_4$Cl. The aqueous phase was extracted with EtOAc, and organic phase was dried over anhydrous Na$_2$SO$_4$ and concentrated in vacuo. Purification by flash chromatography on silica gel (0 to 25%, then 25 to 100% EtOAc in hexanes) provided the title compound: LCMS A, t$_r$=4.03 min, m/z 384.3 [M+H]$^+$; $^1$H NMR (500 MHz, CDCl$_3$) δ 9.29 (s, 1H), 7.94 (d, J=8.5 Hz, 2H), 7.68 (s, 1H), 7.40-7.28 (m, 4H), 7.07 (d, J=1.5 Hz, 1H), 3.92 (s, 3H), 3.63 (dddd, J=8.0, 8.0, 6.0, 6.0 Hz 1H), 3.22 (dd, J=14.0, 8.5 Hz, 1H), 2.93 (dd, J=14.0, 6.0 Hz, 1 H), 1.92-1.84 (m, 1H), 1.66-1.59 (m, 1H), 1.41-1.34 (m, 2H), 0.93 (t, J=7.5 Hz, 3H).

Step E. Methyl 4-((2RS)-2-{[1-(4-tert-butylbenzyl)-5-chloro-1H-indol-2-yl]carbonyl}pentyl)benzoate To a solution of the title compound of Example 3 Step D (240 mg, 0.63 mmol) in DMF (2.5 mL) was added NaH (30 mg, 60% suspension in mineral oil, 0.75 mmol). After 15 min, 4-tert-butylbenzyl bromide (0.126 mL, 0.69 mmol) was added, and the resultant mixture was stirred for 1.5 h, whereupon it was quenched by addition of sat. aq. NH$_4$Cl. The aqueous phase was extracted with EtOAc, and the organic phase was dried over anhydrous Na$_2$SO$_4$ and concentrated in vacuo. Purification by flash chromatography on silica gel (0 to 25%, then 25 to 100% EtOAc in hexanes) provided the title compound: LCMS B, t$_r$=3.30 min, m/z 530.3 [M+H]$^+$; $^1$H NMR (500 MHz, CDCl$_3$) δ 7.84 (d, J=8.5 Hz, 2H), 7.63 (d, J=2.0 Hz, 1H), 7.29-7.23 (m, 4H), 7.15 (d, J=8.0 Hz, 2H), 7.13 (s, 1H), 6.82 (d, J=8.5 Hz, 2H), 5.78 (ABq, J=16.0 Hz, Δv=71.0 Hz, 2H), 3.87 (s, 3H), 3.62 (dddd, J=8.5, 8.5, 5.5, 5.5 Hz, 1H), 3.08 (dd, J=14.0, 8.5 Hz, 1H), 2.78 (dd, J=14.0, 5.5 Hz, 1H), 1.76-1.70 (m, 1H), 1.52-1.45 (m, 1H), 1.26 (s, 9H), 1.23-1.18 (m, 2H), 0.81 (t, J=7.5 Hz, 3H).

Step F. 3-{[4-((2R)-2-{[1-(4-tert-butylbenzyl)-5-chloro-1H-indol-2-yl]carbonyl}pentyl)benzoyl]amino}propanoic acid and 3-{[4-((2S)-2-{[1-(4-tert-butylbenzyl)-5-chloro-1H-indol-2-yl]carbonyl}pentyl)benzoyl]amino}propanoic acid To a solution of the title compound of Example 3 Step E (330 mg, 0.63 mmol) in 1,4-dioxane (3 mL) was added LiOH (150 mg, 6.25 mmol), and the resultant mixture was stirred at 45° C. for 4 h. The mixture was allowed to cool to room temperature whereupon it was quenched by the addition of 2 N aq. HCl. The aqueous phase was extracted with EtOAc, and the organic phase was dried over $Na_2SO_4$ and concentrated in vacuo. To the crude carboxylic acid obtained above were added EDC (359 mg, 1.88 mmol), HOBt (253 mg, 1.88 mmol), and β-alanine tert-butyl ester hydrochloride (341 mg, 1.88 mmol). The resultant mixture was dissolved in DMF (3 mL), DIEA (1.09 mL, 6.16 mmol) was added, and the reaction mixture was stirred at 50° C. for 12 h. The reaction mixture was quenched by addition of sat. aq. $NaHCO_3$, and the aqueous phase was extracted with EtOAc. The organic phase was concentrated in vacuo. Purification by flash chromatography on silica gel (0 to 50%, then 50 to 100% EtOAc in hexanes) provided the racemic amide: LCMS B, $t_r$=3.14 min, m/z 643.3 [M+H]$^+$. Chiral HPLC purification (ChiralPak OD column, 10% iPrOH in heptane, 9 mL/min) provided two isomers, $t_r$=13.2 min and $t_r$=15.7 min. Each amide was separately dissolved in $CH_2Cl_2$ (1 mL) and TFA (1 mL) was added. After 45 min, the mixtures were concentrated in vacuo. Purification by reverse phase HPLC (30 to 100% $CH_3CN$ in $H_2O$, each with 0.1% v/v TFA) provided the title compounds. The following data are for the more potent glucagon receptor antagonist, which is derived from the second eluting tert-butyl ester enantiomer: LCMS B, $t_r$=2.86 min, m/z 587.2 [M+H]$^+$; $^1$H NMR (500 MHz, $d_6$DMSO) δ 8.41 (t, J=5.5 Hz, 1H), 7.79 (d, J=2.0 Hz, 1H), 7.68 (d, J=8.5 Hz, 2H), 7.65 (s, 1H), 7.60 (d, J=9.0 Hz, 1H), 7.33 (dd, J=9.0, 2.0 Hz, 1H), 7.28 (d, J=8.0 Hz, 2H), 7.17 (d, J=8.0 Hz, 2H), 6.73 (d, J=8.0 Hz, 2H), 5.80 (ABq, J=16.0 Hz, Δv=92.6 Hz, 2H), 3.92-3.87 (m, 1H), 3.42 (q, J=7.0 Hz, 2H), 2.96 (dd, J=13.5, 8.5 Hz, 1H), 2.80 (dd, J=13.5, 6.0 Hz, 1H), 2.48 (t, J=7.0 Hz, 2H), 1.60-1.54 (m, 1H), 1.47-1.41 (m, 1H), 1.19 (s, 9H), 1.19-1.11 (m, 2H), 0.76 (t, J=7.0 Hz, 3H).

EXAMPLE 4

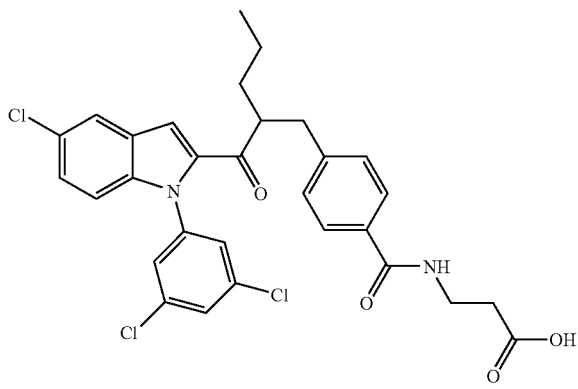

Step A. tert-Butyl 3-{[4-((2RS)-2-{[5-chloro-1-(3,5-dichlorophenyl)-1H-indol-2-yl]carbonyl}pentyl)benzoyl]amino}propanoate To a vial containing the title compound of Example 3 Step D (100 mg, 0.26 mmol), were added 3,5-dichloro iodobenzene (0.045 mL, 0.31 mmol), copper iodide (2.5 mg, 0.012 mmol), potassium phosphate (116 mg, 0.55 mmol), and 1,2-trans-N,N-dimethylcyclohexane diamine (0.0082 mL, 0.05 mmol). The reaction mixture was placed under a nitrogen atmosphere, and anhydrous toluene (0.300 mL, deoxygenated via nitrogen sparge), was added. The vial was then capped and placed in a pre-heated oil bath (110° C.) and stirred rapidly for 20 h. The mixture was allowed to cool to room temperature, then was filtered through a silica gel plug, eluting with EtOAc. The filtrate was concentrated in vacuo: LCMS B, $t_r$=3.10 min, m/z 528.1 [M+H]$^+$. The crude adduct was dissolved in 1,4-dioxane (1.5 mL). 2 N aq. LiOH (1.3 mL, 2.6 mmol) was added, and the resultant mixture was stirred at 50° C. for 1 h. The mixture was allowed to cool to room temperature whereupon it was quenched by the addition of 2 N aq. HCl. The aqueous phase was extracted with EtOAc, and the organic phase was dried over $Na_2SO_4$ and concentrated in vacuo. To the crude carboxylic acid obtained above were added EDC (150 mg, 0.78 mmol), HOBt (105 mg, 0.78 mmol), and beta-alanine tert-butyl ester hydrochloride (141 mg, 0.78 mmol). The resultant mixture was dissolved in DMF (2 mL), DIEA (0.275 mL, 1.56 mmol) was added, and the reaction mixture was stirred at 50° C. for 18 h. The reaction mixture was quenched by addition of sat. aq. $NH_4Cl$, and the aqueous phase was extracted with EtOAc. The organic phase was concentrated in vacuo. Purification by flash chromatography on silica gel (0 to 70%, then 70 to 100% EtOAc in hexanes) provided the title compound: LCMS B, $t_r$=3.01 min, m/z 663.1 [M+H]$^+$; $^1$H NMR (500 MHz, CDCl$_3$) δ 7.67 (d, J=2.0 Hz, 1H), 7.66 (s, 1H), 7.65 (d, J=8.0 Hz, 2H), 7.46 (t, J=7.0 Hz, 1H), 7.27-7.21 (m, 4H), 6.96 (d, J=8.0 Hz, 2H), 8.87 (t, J=5.5 Hz, 1H), 3.65 (q, J=6.0 Hz, 2H), 3.64-3.59 (m, 1 H), 3.04 (dd, J=14.0, 9.0 Hz, 1H), 2.83 (dd, J=14.0, 5.5 Hz, 1H), 2.52 (t, J=6.0 Hz, 1H), 1.80-1.73 (m, 1H), 1.59-1.52 (m, 1H), 1.44 (s, 9H), 1.41-1.33 (m, 2H), 0.92 (t, J=7.0 Hz, 3H).

Step B. 3-{[4-((2R)-2-{[5-Chloro-1-(3,5-dichlorophenyl)-1H-indol-2-yl]carbonyl}pentyl)benzoyl]amino}propanoic acid and 3-{[4-((2S)-2-{[5-Chloro-1-(3,5-dichlorophenyl)-1H-indol-2yl]carbonyl}pentyl)benzoyl]amino}propanoic acid Chiral HPLC purification of the title compound of Example 4 Step A (ChiralCel OD column, 12% iPrOH in heptane, 9 mL/min) provided two isomers, $t_r$=19.5 min and $t_r$=22.2 min. Each was separately dissolved in $CH_2Cl_2$ (1 mL) and TFA (1 mL). After 30 min, the mixtures were concentrated in vacuo. Purification by reverse phase HPLC (75 to 100% $CH_3CN$ in $H_2O$, each with 0.1% v/v TFA) provided the title compounds. The following data are for the more potent glucagon receptor antagonist, which is derived from the second eluting tert-butyl ester enantiomer: LCMS B, $t_r$=2.80 min, m/z 586.9 [M+H]$^+$; $^1$H NMR (500 MHz, $d_6$DMSO) δ 8.40 (t, J=5.5 Hz, 1H), 7.87 (d, J=2.0 Hz, 1 H), 7.78 (s, 1H), 7.75 (t, J=2.0 Hz, 1H), 7.69 (d, J=8.0 Hz, 2H), 7.33 (dd, J=9.0, 2.0 Hz, 1H), 7.33-7.20 (m, 2H), 7.27 (d, J=8.0 Hz, 2H), 7.09 (d, J=9.0 Hz, 1H), 3.87-3.82 (m, 1H), 2.94 (dd, J=14.0, 9.0 Hz, 1H), 2.79 (dd, J=14.0, 6.0 Hz, 1H), 1.66-1.58 (m, 1H), 1.47-1.40 (m, 1H), 1.32-1.23 (m, 2H), 0.83 (t, J=7.0 Hz, 3H), β-alanine methylene protons obscured by residual H₂O and DMSO signals.

EXAMPLE 5

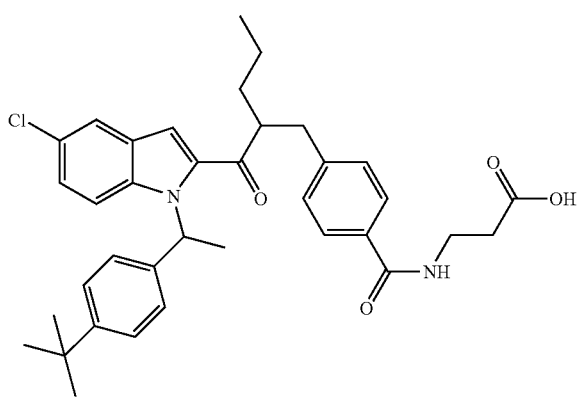

Step A. Methyl 4-[(2SR)-2-({1-[(1SR) 1-(4-tert-butylphenyl)ethyl]-5-chloro-1H-indol-2-yl}carbonyl)pentyl]benzoate and Methyl 4-[(2RS)-2-({1-[(1SR)-1-(4-tert-butylphenyl)ethyl]-5-chloro-1H-indol-2-yl}carbonyl)pentyl]benzoate To a solution of the title compound of Example 3 Step D (110 mg, 0.29 mmol) and racemic 4-tert-butyl-sec-phenethyl alcohol (153 mg, 0.86 mmol) in toluene (2 mL) were added triphenylphosphine (225 mg, 0.86 mmol) and diisopropyl azodicarboxylate (0.169 mL, 0.86 mmol), and the mixture was heated to 60° C. After 45 min, the mixture was allowed to cool to room temperature, then was concentrated in vacuo. The resulting mixture of diastereomers was filtered through a pad of silica gel, then taken forward without further purification: LCMS A, t$_r$=3.78 min, m/z 544.4 [M+H]⁺.

Step B. 3-({4-[(2SR)-2-({1-[(1SR)-1-(4-tert-Butylphenyl)ethyl]-5-chloro-1H-indol-2-yl}carbonyl)pentyl]benzoyl}amino)propanoic acid and 3-({4-[(2RS)-2-({1-[(1SR)-1-(4-tert-Butylphenyl)ethyl]-5-chloro-1H-indol-2-yl}carbonyl)pentyl]benzoyl}amino)propanoic acid To a solution of the title compound of Example 5 Step A (45 mg, 0.08 mmol) in 1,4-dioxane (0.4 mL) was added a solution of LiOH (19.8 mg, 0.83 mmol) in H₂O (0.4 mL), and the resultant mixture was stirred at 50° C. for 18 h. The mixture was allowed to cool to room temperature whereupon it was quenched by the addition of 2 N aq. HCl. The aqueous phase was extracted with EtOAc, and the organic phase was dried over Na₂SO₄ and concentrated in vacuo. To the crude carboxylic acid obtained above were added EDC (48 mg, 0.25 mmol), HOBt (34 mg, 0.25 mmol), and β-alanine tert-butyl ester hydrochloride (45 mg, 0.25 mmol). The resultant mixture was dissolved in DMF (0.4 mL), DIEA (0.144 mL, 0.81 mmol) was added, and the reaction mixture was stirred at 50° C. for 2 h. The reaction mixture was quenched by addition of sat. aq. NH₄Cl, and the aqueous phase was extracted with EtOAc. The organic phase was concentrated in vacuo, then dissolved in CH₂Cl₂ (0.5 mL) and TFA (0.5 mL). After 30 min, the mixture was concentrated in vacuo. Purification by reverse phase HPLC (30 to 100% CH₃CN in H₂O, each with 0.1% v/v TFA) provided the title compounds. Data for the first eluting diastereomer: LCMS A, t$_r$=4.24 min, m/z 601.4 [M+H]⁺; ¹H NMR (500 MHz, d₆DMSO) δ 8.42 (t, J=5.5 Hz, 1H), 7.71 (d, J=8.5 Hz, 2H), 7.45 (d, J=8.5 Hz, 1H), 7.29-7.26 (m, 6H), 7.21 (dd, J=8.5, 2.0 Hz, 1H), 7.15 (d, J=8.5 Hz, 2H), 5.22 (q, J=7.5 Hz, 1H), 3.84-3.81 (m, 1H), 3.42 (q, J=6.0 Hz, 2H), 3.08 (dd, J=13.5, 8.0 Hz, 1H), 2.82 (dd, J=13.5, 6.0 Hz, 1H), 1.67 (d, J=7.5 Hz, 3H), 1.66-1.59 (m, 1H), 1.49-1.42 (m, 1H), 1.29-1.23 (m, 2H), 1.24 (s, 9H), 0.80 (t, J=7.0 Hz, 3H), α-CO₂H β-alanine methylene group obscured by DMSO signal. Data for the second eluting diastereomer: LCMS A, t$_r$=4.26 min, m/z 601.4 [M+H]⁺; ¹H NMR (500 MHz, d₆DMSO) δ 8.43 (t, J=5.5 Hz, 1H), 7.72 (d, J=8.0 Hz, 2H), 7.46 (d, J=8.5 Hz, 1H), 7.30 (d, J=8.0 Hz, 2H), 7.24-7.20 (m, 6H), 7.06 (d, J=8.5 Hz, 2H), 5.22 (q, J=7.5 Hz, 1H), 3.88-3.82 (m, 1H), 3.43 (q, J=6.0 Hz, 2H), 3.06 (dd, J=13.5, 8.0 Hz, 1H), 2.86 (dd, J=13.5, 6.0 Hz, 1H), 2.48 (q, J=7.0 Hz, 2H), 1.68-1.61 (m, 1H), 1.64 (d, J=7.5 Hz, 3H), 1.30-1.22 (m, 2H), 1.23 (s, 9H), 0.81 (t, J=7.0 Hz, 3H).

EXAMPLE 6

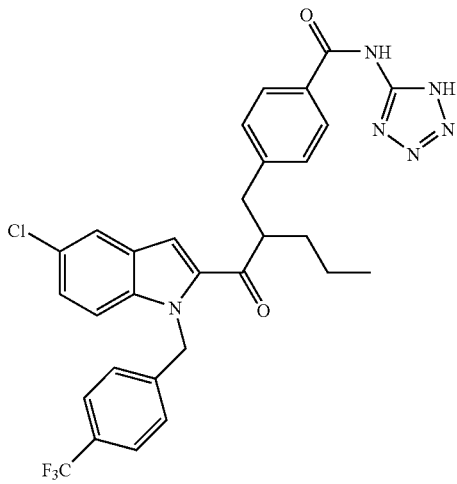

Step A. Methyl 4-[(2RS)-2-({5-chloro-1-[4-(trifluoromethyl)benzyl]-1H-indol-2-yl}carbonyl)pentyl]benzoate To a solution of the title compound of Example 3 Step D (39.0 mg, 0.10 mmol) in DMF (1.0 mL) was added NaH (4.3 mg, 60% suspension in mineral oil, 0.11 mmol). After 10 min, a solution of 4-trifluoromethylbenzyl bromide (26.0 mg, 0.11 mmol) in DMF (0.5 mL) was added, and the reaction mixture was stirred for 18 h, whereupon it was quenched by addition of sat. aq. NaHCO₃. The aqueous phase was extracted with EtOAc, and the organic phase was dried over anhydrous Na₂SO₄ and concentrated in vacuo. Purification by flash chromatography on silica gel (0 to 10%, then 10 to 100% EtOAc in hexanes) provided the title compound: LCMS A, t$_r$=4.65 min, m/z 542.1 [M+H]⁺; ¹H NMR (500 MHz, CDCl₃) δ 7.87 (d, J=8.5 Hz, 2H), 7.71 (d, J=1.5 Hz, 1H), 7.51 (d, J=8.5 Hz, 2H), 7.33-7.23 (m, 3H), 7.19 (d, J=8.5 Hz, 2H), 6.98 (d, J=8.0 Hz, 2H), 5.88 (ABq, J=16.5 Hz, Δν=86 Hz, 2H), 3.91 (s, 3H), 3.69 (dddd, J=9.0, 9.0, 5.5, 5.5 Hz, 1H), 3.10 (dd, J=13.5, 9.0 Hz, 1H), 2.85 (dd, J=13.5, 5.5 Hz, 1H), 1.79-1.74 (m, 2H), 1.58-1.53 (m, 2H), 0.92 (t, J=7.0 Hz, 3H).

Step B. 4-[(2RS)-2-({5-Chloro-1-[4-(trifluoromethyl)benzyl]-1H-indol-2-yl}carbonyl)pentyl]-N-1H-tetrazol-5-ylbenzamide To a solution of the title compound of Example 6 Step A (49.0 mg, 0.091 mmol) in 1,4-dioxane (0.5 mL) was added a solution of LiOH (22.0 mg, 0.91 mmol) in H$_2$O (0.5 mL), and the resultant mixture was stirred at 45° C. for 4 h. The mixture was allowed to cool to room temperature whereupon it was quenched by the addition of 2 N aq. HCl. The aqueous phase was extracted with EtOAc, and the organic phase was dried over Na$_2$SO$_4$ and concentrated in vacuo. To the crude carboxylic acid obtained above were added EDC (52.0 mg, 0.27 mmol), HOBt (37.0 mg, 0.27 mmol), and 5-amino-1H-tetrazole (28.0 mg, 0.27 mmol). The resultant mixture was dissolved in DMF (1 mL), DIEA (0.158 mL, 0.91 mmol) was added, and the reaction mixture was stirred at 50° C. for 2 h. The reaction mixture was quenched by addition of sat. aq. NH$_4$Cl, and the aqueous phase was extracted with EtOAc (2×). The combined organic phases were concentrated in vacuo. Purification by reverse phase HPLC (30 to 100% CH$_3$CN in H$_2$O, each with 0.1% v/v TFA) provided the title compound: LCMS A, t$_r$=4.15 min, m/z 595.1 [M+H]$^+$; $^1$H NMR (500 MHz, d$_6$DMSO) δ 7.92 (d, J=8.0 Hz, 2H), 7.82 (d, J=2.0 Hz, 1H), 7.70 (m, 1H), 7.64 (d, J=8.0 Hz, 1H), 7.55 (d, J=9.0 Hz, 2H), 7.36-7.34 (m, 3H), 6.98 (d, J=8.0 Hz, 2H), 5.90 (ABq, J=16.5 Hz, Δv=37.0 Hz), 3.93-3.89 (m, 1H), 2.98 (dd, J=14.0, 9.0 Hz, 1H), 2.81 (dd, J=14.0, 6.0 Hz, 1H), 1.56-1.51 (m, 1H), 1.44-1.37 (m, 1H), 1.09-1.01 (m, 2H), 0.71 (t, J=7.0 Hz, 3H).

EXAMPLE 7

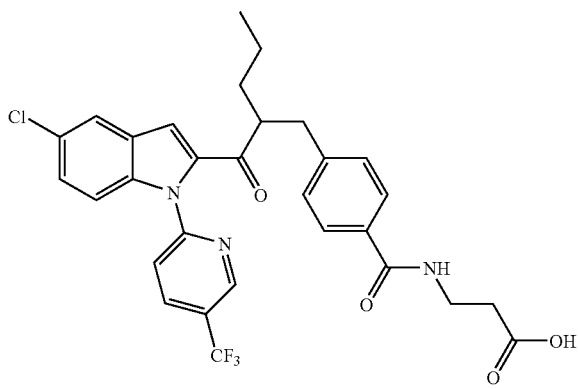

Step A. tert-Butyl 3-[(4-{(2R)-2-[(5-chloro-1H-indol-2-yl)carbonyl]pentyl}benzoyl)amino]propanoate and tert-Butyl 3-[(4-{(2S)-2-[(5-chloro-1H-indol-2-yl)carbonyl]pentyl}benzoyl)amino]propanoate To a solution of the title compound of Example 3 Step D (668 mg, 1.74 mmol) in 1,4-dioxane (9 mL) was added 2 N aq. LiOH (8.7 mL, 17.4 mmol), and the resultant mixture was stirred at 50° C. for 1.5 h. The mixture was allowed to cool to room temperature whereupon it was quenched by the addition of 2 N aq. HCl. The aqueous phase was extracted with EtOAc, and the organic phase was dried over Na$_2$SO$_4$ and concentrated in vacuo. To the crude carboxylic acid obtained above were added EDC (1.00 g, 5.24 mmol), HOBt (705 mg, 5.24 mmol), and β-alanine tert-butyl ester hydrochloride (948 mg, 5.24 mmol). The resultant mixture was dissolved in DMF (9 mL), DIEA (3.0 mL, 16.9 mmol) was added, and the reaction mixture was stirred at 50° C. for 1 h. The reaction mixture was quenched by addition of sat. aq. NH$_4$Cl, and the aqueous phase was extracted with EtOAc. The organic phase was concentrated in vacuo. Purification by flash chromatography on silica gel (0 to 50%, then 50 to 100% EtOAc in hexanes) provided the title compound as a racemic mixture. Chiral HPLC purification (ChiralPak AD-H column, 30% iPrOH in heptane, 9 mL/min) provided two isomers, t$_r$=16.2 min and t$_r$=20.7 min. The following data are for the first eluting enantiomer: LCMS B, t$_r$=2.60 min, m/z 497.3 [M+H]$^+$; $^1$H NMR (500 MHz, CDCl$_3$) δ 9.17 (s, 1H), 7.64 (s, 1H), 7.61 (d, J=8.0 Hz, 2H), 7.33-7.28 (m, 3H), 7.22 (d, J=8.0 Hz, 2H), 7.02 (s, 1H), 6.78 (t, J=6.0 Hz, 1H), 3.63 (q, J=6.0 Hz, 2H), 3.60-3.54 (m, 1H), 3.15 (dd, J=13.5, 8.0 Hz, 1H), 2.86 (dd, J=13.5, 6.0 Hz, 1H), 2.51 (t, J=6.0 Hz, 2H), 1.86-1.78 (m, 1H), 1.61-1.54 (m, 1H), 1.43 (s, 9H), 1.36-1.29 (m, 2H), 0.88 (t, J=8.0 Hz, 3H).

Step B. tert-Butyl 3-({4-[(2R)-2-({5-chloro-1-[5-(trifluoromethyl)pyridin-2-yl]-1H-indol-2-yl}carbonyl)pentyl]benzoyl}amino)propanoate or tert-Butyl 3-({4-[(2S)-2-({5-chloro-1-[5-(trifluoromethyl)pyridin-2-yl]-1H-indol-2-yl}carbonyl)pentyl]benzoyl}amino)propanoate To a vial containing the title compound of Example 7 Step A (first eluting enantiomer, 25.0 mg, 0.050 mmol) were added 2-bromo-5-trifluoromethylpyridine (14.0 mg, 0.06 mmol), potassium phosphate (22.0 mg, 0.11 mmol), copper iodide (1.5 mg, 0.01 mmol), and trans N,N-dimethyl-1,2-cyclohexanediamine (0.006 mL, 0.04 mmol). The resulting mixture was purged with N$_2$, and degassed toluene (0.100 mL) was added. The reaction mixture was capped, placed in a 110° C. bath, and was stirred for 18 h. Upon cooling to room temperature, the mixture was filtered through a short pad of silica gel, concentrated in vacuo, and taken forward without further purification. A small portion of the crude mixture was removed for characterization. The crude product was determined to have 70% enantiomeric excess (ChiralPak AD-H column, 20% iPrOH in n-heptane, 0.5 mL/min, major isomer t$_r$=15.3 min, minor isomer t$_r$=33.9 min): LCMS A, t$_r$=4.25 min, m/z 586.1 [M−tBu+H]$^+$; $^1$H NMR (500 MHz, CDCl$_3$) δ 8.77 (d, J=5.0 Hz, 1H), 7.69 (d, J=2.0 Hz, 1H), 7.64 (d, J=8.0 Hz, 2H), 7.58 (d, J=5.0 Hz, 1H), 7.31 (s, 1H), 7.29 (dd, J=8.5, 2.0 Hz, 1H), 7.25-7.02 (m, 4H), 6.87 (t, J=6.0 Hz, 1H), 3.65 (q, J=6.0 Hz, 2H), 3.64-3.61 (m, 1H), 3.09 (dd, J=13.5, 9.0 Hz, 1H), 2.82 (dd, J=13.5, 5.5 Hz, 1H), 2.53 (t, J=6.0 Hz, 2H), 1.81-1.74 (m, 2H), 1.57-1.53 (m, 1H), 1.44 (s, 9H), 1.41-1.36 (m, 1H), 0.91 (t, J=7.5 Hz, 3H).

Step C. 3-({4-[(2S)-2-({5-Chloro-1-[5-(trifluoromethyl)pyridin-2-yl]-1H-indol-2-yl}carbonyl)pentyl]benzoyl}amino)propanoic acid or 3-({4-[(2R)-2-({5-Chloro-1-[5-(trifluoromethyl)pyridin-2-yl]-1H-indol-2-yl}carbonyl)pentyl]benzoyl}amino)propanoic acid The title compound of Example 7 Step B was dissolved in CH$_2$Cl$_2$ (1 mL), and TFA (1 mL) was added. After 1 h, the reaction mixture was concentrated in vacuo. Purification by reverse phase HPLC (50 to 100% CH$_3$CN in H$_2$O, each with 0.1% v/v TFA) provided the title compound: LCMS D, t$_r$=1.27 min, m/z 586.1 [M+H]$^+$; $^1$H NMR (500 MHz, d$_6$DMSO) δ 8.84 (d, J=5.0 Hz, 1H), 8.40 (t, J=5.5 Hz, 1H), 7.89-7.88 (m, 2H), 7.80 (s, 1H), 7.69 (d, J=8.5 Hz, 2H), 7.68 (s, 1H), 7.37 (dd, J=9.0, 2.0 Hz, 1H), 7.32-7.29 (m, 3H), 3.88-3.83 (m, 1H), 2.97 (dd, J=13.5, 8.0 Hz, 1H), 2.77 (dd, J=13.5, 6.0 Hz, 1H), 2.46 (t, J=7.0 Hz, 2H), 1.66-1.59 (m, 1H), 1.48-1.42 (m, 1H), 1.32-1.25 (m, 2H), 0.83 (t, J=7.0 Hz, 3H), α-NH β-alanine methylene obscured by residual H₂O signal.

EXAMPLE 8

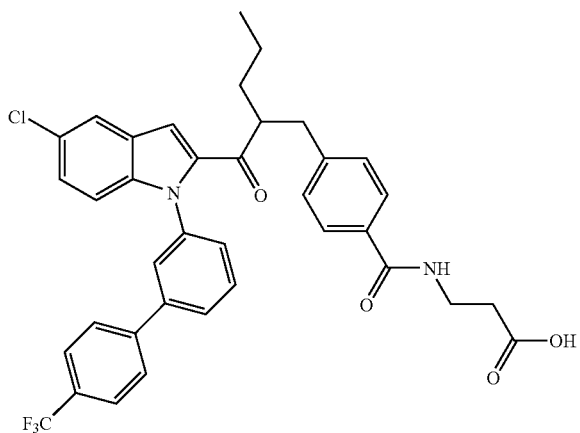

Step A. tert-Butyl 3-{[4-((2RS)-2-{[1-(3-bromophenyl)-5-chloro-1H-indol-2-yl]carbonyl}pentyl)benzoyl]amino}propanoate To a vial containing the title compound of Example 3 Step D (300 mg, 0.78 mmol), were added 3-bromo iodobenzene (0.120 mL, 0.94 mmol), copper iodide (11.0 mg, 0.078 mmol), potassium phosphate (349 mg, 1.64 mmol), and 1,2-trans-N,N-dimethylcyclohexane diamine (0.049 mL, 0.31 mmol). The reaction mixture was placed under a nitrogen atmosphere, and anhydrous toluene (1.0 mL, deoxygenated via nitrogen sparge), was added. The vial was then capped and placed in a pre-heated oil bath (110° C.) and stirred rapidly for 20 h. The mixture was then allowed to cool to room temperature, then was filtered through a silica gel plug, eluting with EtOAc. The filtrate was concentrated in vacuo: LCMS B, $t_r$=3.11 min, m/z 540.0 [M+H]⁺. The crude adduct was dissolved in 1,4-dioxane (4 mL). 2 N aq. LiOH (3.9 mL, 7.8 mmol) was added, and the resultant mixture was stirred at 50° C. for 4 h. The mixture was allowed to cool to room temperature whereupon it was quenched by the addition of 2 N aq. HCl. The aqueous phase was extracted with EtOAc, and the organic phase was dried over Na₂SO₄ and concentrated in vacuo. To the crude carboxylic acid obtained above were added EDC (450 mg, 2.36 mmol), HOBt (317 mg, 2.36 mmol), and β-alanine tert-butyl ester hydrochloride (426 mg, 2.36 mmol). The resultant mixture was dissolved in DMF (4 mL), DIEA (1.36 mL, 7.69 mmol) was added, and the reaction mixture was stirred at 50° C. for 18 h. The reaction mixture was quenched by addition of sat. aq. NH₄Cl, and the aqueous phase was extracted with EtOAc. The organic phase was concentrated in vacuo. Purification by flash chromatography on silica gel (0 to 50%, then 50 to 100% EtOAc in hexanes) provided the title compound: LCMS A, $t_r$=4.48 min, m/z 597.3 [M−tBu+H]⁺; ¹H NMR (500 MHz, CDCl₃) δ 7.67-7.64 (m, 4H), 7.59 (d, J=9.0 Hz, 1H), 7.39-7.35 (m, 1H), 7.24-7.20 (m, 5H), 6.95 (d, J=9.0 Hz, 1H), 6.81-6.79 (m, 1H), 3.64 (q, J=6.0 Hz, 2H), 3.63-3.56 (m, 1H), 3.05 (dd, J=13.5, 9.0 Hz, 1H), 2.80 (dd, J=13.5, 5.5 Hz, 1H), 2.52 (t, J=6.0 Hz, 2H), 1.79-1.72 (m, 1H), 1.56-1.47 (m, 1H), 1.44 (s, 9H), 1.39-1.30 (m, 2H), 0.90 (t, J=7.0 Hz, 3H).

Step B. 3-({4-[(2RS)-2-({5-chloro-1-[4'-(trifluoromethyl)biphenyl-3-yl]-1H-indol-2-yl}carbonyl)pentyl]benzoyl}amino)propanoic acid To a vial containing the title compound of Example 8 Step A (20.0 mg, 0.031 mmol) were added 4-trifluoromethylbenzene boronic acid (8.7 mg, 0.046 mmol), palladium acetate (2.0 mg, 0.009 mmol), tri-o-tolyl phosphine (9.0 mg, 0.031 mmol), and cesium carbonate (7.5 mg, 0.023 mmol). The mixture was purged with N₂, and degassed toluene (0.20 mL) was added. The resulting suspension was capped and placed in a 110° C. bath. After 18 h, the mixture was allowed to cool to room temperature, and was filtered through a silica gel plug, eluting with EtOAc. The filtrate was concentrated in vacuo, then was dissolved in CH₂Cl₂ (1 mL) and TFA (1 mL) was added. After 30 min, the mixture was concentrated in vacuo. Purification by reverse phase HPLC (60 to 100% CH₃CN in H₂O, each with 0.1% v/v TFA) provided the title compound: LCMS B, $t_r$=2.87 min, m/z 661.1 [M+H]⁺; ¹H NMR (500 MHz, d₆DMSO) δ 8.40 (t, J=5.5. Hz, 1H), 7.91-7.58 (m, 11H), 7.31 (dd, J=9.0, 2.0 Hz, 1H), 7.28 (d, J=8.0 Hz, 2H), 7.10 (d, J=9.0 Hz, 1H), 6.53-6.49 (m, 1H), 3.88-3.84 (m, 1H), 3.40 (q, J=7.0 Hz, 2H), 2.94 (dd, J=13.5, 8.5 Hz, 1H), 2.76 (dd, J=13.5, 6.5 Hz, 1H), 2.46 (t, J=7.0 Hz, 2H), 1.65-1.58 (m, 1H), 1.46-1.40 (m, 1H), 1.32-1.23 (m, 1H), 0.82 (t, J=7.0 Hz, 3H).

EXAMPLE 9

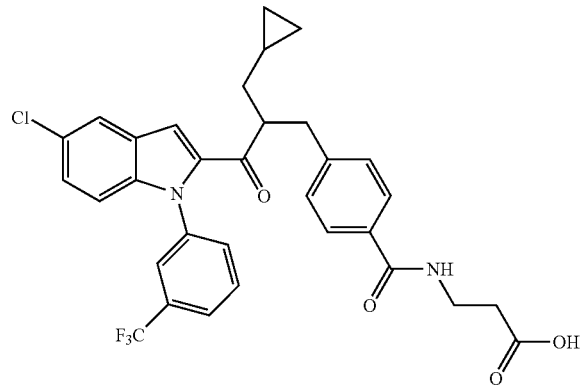

Step A. Ethyl 5-chloro-1-[3-(trifluoromethyl)phenyl]-1H-indole-2-carboxylate

To a vial containing ethyl 5-chloroindole-2-carboxylate (1.50 g, 6.70 mmol), were added 3-iodobenzotrifluoride (1.16 mL, 8.10 mmol), potassium phosphate (2.98 g, 14.1 mmol), copper iodide (64.0 mg, 0.34 mmol), and 1,2-trans-N,N'-dimethylcyclohexane diamine (0.211 mL, 1.33 mmol), and the mixture was purged with N₂. Anhydrous toluene (degassed via N₂-sparge, 6.7 mL) was added, and the reaction vial was capped and placed in a pre-heated (110° C.) oil bath. The mixture was stirred vigorously for 18 h, then was allowed to cool to room temperature. The reaction mixture was filtered, rinsing with ethyl acetate, and the filtrate was concentrated in vacuo. Purification by flash chromatography on silica gel (0 to 30%, then 30 to 100% hexanes in ethyl acetate)

afforded the title compound: LCMS C, t$_r$=2.86 min, m/z 368.1 [M+H]$^+$; $^1$H NMR (500 MHz, CDCl$_3$) δ 7.76 (d, J=8.0 Hz, 1H), 7.71 (d, J=2.0 Hz, 1H), 7.66 (t, J=8.0 Hz, 1H), 7.60 (s, 1H), 7.53 (d, J=8.0 Hz, 1H), 7.42 (s, 1H), 7.25 (dd, J=9.0, 2.0 Hz, 1H), 6.97 (d, J=9.0 Hz, 1H), 4.22 (q, J=7.0 Hz, 2H), 1.22 (t, J=7.0 Hz, 3H).

Step B. tert-Butyl 3-{5-chloro-1-[3-(trifluoromethyl)phenyl]-1H-indol-2-yl}-3-oxopropanoate To a cooled (−78° C.) solution of LHMDS (13 mL, 1.0 M in THF, 13.0 mmol) in THF (13 mL) was added tert-butyl acetate (1.76 mL, 13.0 mmol), dropwise. After 30 min, a solution of the title compound of Example 9 Step A (1.60 g, 4.36 mmol) in THF (4 mL) was added, and the mixture was held at −78° C. for 30 min, then was placed in a 0° C. bath. After 1.5 h, the reaction mixture was poured into sat. aq. NaHCO$_3$ and extracted twice with ethyl acetate. The combined organic phases were concentrated in vacuo. Purification by flash chromatography on silica gel (0 to 30%, then 30 to 100% hexanes in ethyl acetate) afforded the title compound: LCMS C, t$_r$=2.99 min, m/z 382.1 [M−tBu+H]$^+$; $^1$H NMR (500 MHz, CDCl$_3$) δ 7.74 (d, J=2.0 Hz, 1H), 7.72 (d, J=8.0 Hz, 1H), 7.64 (t, J=8.0 Hz, 1H), 7.56 (s, 1H), 7.50 (d, J=8.0 Hz, 1H), 7.38 (s, 1H), 7.29 (dd, J=9.0, 2.0 Hz, 1H), 7.01 (d, J=9.0 Hz, 1H), 3.83 (s, 2H), 1.44 (s, 9H).

Step C. 1-{5-Chloro-1-[3-(trifluoromethyl)phenyl]-1H-indol-2-yl}-3-cyclopropylpropan-1-one To a solution of the title compound of Example 9 Step B (650 mg, 1.48 mmol) in DMF (3 mL) was added sodium hydride (65 mg, 60% suspension in mineral oil, 1.63 mmol). After 15 min, bromomethyl cyclopropane (0.159 mL, 1.63 mmol) was added, then the mixture was placed in a heated (60° C.) oil bath. The reaction mixture was stirred for 18 h, then was allowed to cool to room temperature and was quenched by addition of saturated aq. NaHCO$_3$. The aqueous phase was extracted twice with EtOAc. The combined organic phases were dried over anhydrous Na$_2$SO$_4$ and concentrated in vacuo: LCMS A, t$_r$=4.44 min, m/z 490.3 [M+H]$^+$. The crude adduct was dissolved in CH$_2$Cl$_2$ (4 mL) and trifluoroacetic acid (4 mL) and stirred for 2 h. The volatiles were removed in vacuo, and the crude β-keto acid was dissolved in benzene (10 mL), then was heated at 90° C. for 15 h. The mixture was allowed to cool to room temperature and was concentrated in vacuo. Purification by reverse phase HPLC (60 to 100% CH$_3$CN in H$_2$O, both 0.1% v/v trifluoroacetic acid) afforded the title compound: LCMS A, t$_r$=4.31 min, m/z 392.3 [M+H]$^+$; $^1$H NMR (500 MHz, CDCl$_3$) δ 7.73 (d, J=2.0 Hz, 1H), 7.72 (d, J=7.5 Hz, 1H), 7.64 (t, J=8.0 Hz, 1H), 7.53 (s, 1H), 7.46 (d, J=8.0 Hz, 1H), 7.41 (s, 1H), 7.26 (dd, J=9.0, 2.0 Hz, 1H), 6.95 (d, J=9.0 Hz, 1H), 3.06 (t, J=7.5 Hz, 2H), 1.59 (q, J=7.5 Hz, 2H), 0.78-0.70 (m, 1H), 0.40 (app dq, J=8.0, 4.5 Hz, 2H), 0.05 (dd, J=10.5, 4.5 Hz, 2H).

Step D. 3-({4-[(2R)-3-{5-Chloro-1-[3-(trifluoromethyl)phenyl]-1H-indol-2-yl}-2-(cyclopropylmethyl)-3-oxopropyl]benzoyl}amino)propanoic acid and 3-({4-[(2S)-3-{5-Chloro-1-[3-(trifluoromethyl)phenyl]-1H-indol-2-yl}-2-(cyclopropylmethyl)-3-oxopropyl]benzoyl}amino)propanoic acid To a cooled (−78° C.) solution of the title compound of Example 9 Step C (200 mg, 0.51 mmol) in THF (2 mL) was added KHMDS (2.0 mL, 0.5 M solution in toluene, 1.0 mmol). After 30 min, a solution of methyl 4-(bromomethyl) benzoate (117 mg, 1.0 mmol) in THF (1 mL) was added. After 1 h, the reaction mixture was removed from the −78° C. bath, and allowed to warm slowly to room temperature, whereupon it was quenched by addition of sat. aq. NaHCO$_3$. The aqueous phase was extracted with EtOAc, and the organic phase was dried over anhydrous Na$_2$SO$_4$ and concentrated in vacuo: LCMS A, t$_r$=4.46 min, m/z 540.4 [M+H]$^+$. The crude adduct obtained above was dissolved in 1,4-dioxane (2 mL), aqueous LiOH (1.25 mL, 2.0 M aqueous, 2.5 mmol) was added, and the mixture was stirred at 40° C. for 15 h. The reaction mixture was quenched by addition of 2 N aq. HCl, and was extracted with EtOAc. The combined organic phases were dried over anhydrous Na$_2$SO$_4$ and concentrated in vacuo. To a flask containing the crude carboxylic acid obtained above, were added EDC (292 mg, 1.53 mmol), HOBt (207 mg, 1.53 mmol), and β-alanine tert-butyl ester hydrochloride (277 mg, 1.53 mmol). The mixture was dissolved in DMF (2 mL), DIEA was added (0.541 mL, 3.06 mmol), and the resultant solution was stirred at 50° C. for 45 min, whereupon it was quenched by addition of sat. aq. NaHCO$_3$. The aqueous phase was extracted with EtOAc, and the organic phase was concentrated in vacuo. Purification by flash chromatography on silica gel (0 to 40% then 40 to 100% EtOAc in hexanes) provided the racemic amides: LCMS A, t$_r$=4.31 min, m/z 597.4 [M−tBu+H]$^+$. Chiral HPLC purification (ChiralPak AD-H column, 10% iPrOH in heptane, 9 mL/min) provided two isomers, t$_r$=34.8 min and t$_r$=40.7 min. Each amide was separately dissolved in CH$_2$Cl$_2$ (1 mL) and TFA (1 mL) was added. After 30 min, the mixtures were concentrated in vacuo. Reverse phase HPLC purification (50 to 100% CH$_3$CN in H$_2$O, each containing 0.1% v/v TFA) provided the title compounds. The following data are for the more potent glucagon receptor antagonist, which is derived from the first eluting tert-butyl ester enantiomer: LCMS B, t$_r$=2.71 min, m/z 597.2 [M+H]$^+$; $^1$H NMR (500 MHz, d$_6$DMSO) δ 8.40 (t, J=5.5 Hz, 1H), 7.88 (d, J=2.0 Hz, 1H), 7.85 (d, J=8.0 Hz, 1H), 7.80 (s, 1H), 7.39 (d, J=8.0 Hz, 1H), 7.69 (d, J=8.0 Hz, 1H), 7.56-7.42 (br m, 2H), 7.32 (dd, J=9.0, 2.0 Hz, 1H), 7.27 (d, J=8.0 Hz, 2H), 6.99 (d, J=9.0 Hz, 1H), 4.00-3.94 (m, 1H), 2.94 (dd, J=13.5, 8.5 Hz, 1H), 2.84 (dd, J=13.5, 6.0 Hz, 1H), 2.46 (t, J=7.0 Hz, 2H), 1.44 (ddd, J=14.0, 8.0, 8.0 Hz, 1H), 1.38 (ddd, J=13.0, 6.0, 6.0 Hz, 1H), 0.70-0.62 (m, 1H), 0.39-0.28 (m, 2H), 0.04-0.00 (m, 1H), −0.04-(−0.086) (m, 1H), α-NH β-alanine methylene group obscured by residual H$_2$O signal.

EXAMPLE 10

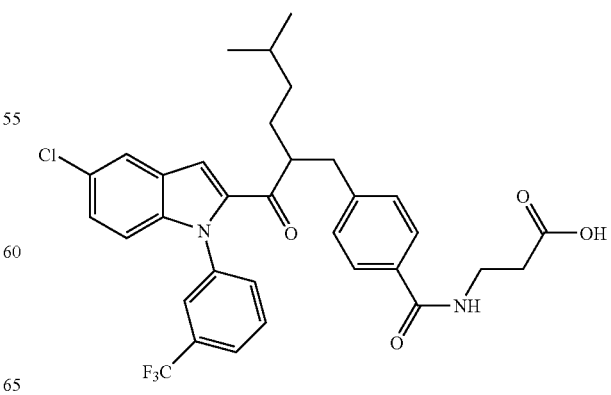

Step A. Methyl 4-(3-{5-chloro-1-[3-(trifluoromethyl)phenyl]-1H-indol-2-yl}-3-oxopropyl)benzoate To a solution the title compound of Example 9 Step B (1.17 g, 2.67 mmol) in DMF (3.5 mL) was added NaH (112 mg, 60% suspension in mineral oil, 2.81 mmol). After 10 min, a solution of methyl 4-bromomethyl benzoate (643 mg, 2.81 mmol) in DMF (1.5 mL) was added, and the resultant mixture was stirred for 3 h, whereupon it was quenched by addition of sat. aq. NaHCO$_3$. The aqueous phase was extracted with EtOAc, and the organic phase was dried over anhydrous Na$_2$SO$_4$ and concentrated in vacuo: LCMS A, t$_r$=4.20 min, m/z 530.3 [M−tBu+H]$^+$. The crude adduct obtained above was dissolved in CH$_2$Cl$_2$ (3 mL) and TFA (3 mL) was added. After 2 h, the reaction mixture was concentrated in vacuo. Residual TFA was removed by azeotroping from benzene to provide a crude oil that was dissolved in anhydrous benzene, and heated at 80° C. for 2 h. After cooling to room temperature, the mixture was concentrated in vacuo. Purification by flash chromatography on silica gel (0 to 10%, then 10 to 100% EtOAc in hexanes) provided the title compound: LCMS A, t$_r$=4.37 min, m/z 486.3 [M+H]$^+$; $^1$H NMR (500 MHz, CDCl$_3$) δ 7.96 (d, J=8.5 Hz, 2H), 7.76-7.72 (m, 1H), 7.70 (d, J=2.0 Hz, 1H), 7.64 (app t, J=8.0 Hz, 1H), 7.51 (s, 1H), 7.42 (d, J=8.0 Hz, 1H), 7.36 (s, 1H), 7.28 (d, J=2.0 Hz, 1H), 7.26 (d, J=2.0 Hz, 1H), 6.94 (d, J=9.5 Hz, 1H), 3.90 (s, 3H), 3.31 (t, J=7.5 Hz, 2H), 3.06 (t, J=7.5 Hz, 2H).

Step B. tert-Butyl 3-({4-[(2RS)-2-({5-chloro-1-[3-(trifluoromethyl)phenyl]-1-indol-2-yl}-2-(cyclopropylmethyl)-3-oxopropyl]benzoyl}amino)propanoic acid To a cooled (−78° C.) solution of the title compound of Example 10 Step A (170 mg, 0.35 mmol) in THF (1.5 mL) was added KHMDS (0.91 mL, 0.5 M in toluene, 0.45 mmol). After 30 min, 1-bromo-3-methyl-2-butene (0.061 mL, 0.53 mmol) was added, and the resultant mixture was allowed to warm slowly to room temperature over 15 h. The mixture was then quenched by addition of 1 N aq. HCl, and the aqueous phase was extracted with EtOAc. The organic phase was dried over anhydrous Na$_2$SO$_4$, and concentrated in vacuo: LCMS B, t$_r$=3.16 min, m/z 554.2 [M+H]$^+$. To a solution of the crude adduct obtained above in 1,4-dioxane (2 mL) was added 2 N aq. LiOH (1.7 mL, 3.4 mmol), and the resultant mixture was stirred at 40° C. for 2 h. The mixture was allowed to cool to room temperature whereupon it was quenched by the addition of 2 N aq. HCl. The aqueous phase was extracted with EtOAc, and the organic phase was dried over Na$_2$SO$_4$ and concentrated in vacuo. To the crude carboxylic acid obtained above were added EDC (200 mg, 1.05 mmol), HOBt (142 mg, 1.05 mmol), and β-alanine tert-butyl ester hydrochloride (190 mg, 1.05 mmol). The resultant mixture was dissolved in DMF (1 mL), DIEA (0.370 mL, 2.10 mmol) was added, and the reaction mixture was stirred at 50° C. for 2 h. The reaction mixture was quenched by addition of sat. aq. NaHCO$_3$, and the aqueous phase was extracted with EtOAc. The organic phase was concentrated in vacuo. Purification by flash chromatography on silica gel (0 to 40%, then 40 to 100% EtOAc in hexanes) provided the title compound: LCMS B, t$_r$=3.08 min, m/z 667.2 [M+H]$^+$; $^1$H NMR (500 MHz, CDCl$_3$) δ 7.72 (d, J=8.0 Hz, 1H), 7.67 (d, J=2.0 Hz, 1H), 7.63-7.60 (m, 3H), 7.37 (br s, 1H), 7.23 (dd, J=9.0, 2.0 Hz, 1H), 7.20 (d, J=7.5 Hz, 2H), 7.19 (s, 1H), 6.92 (d, J=9.0 Hz, 1H), 6.80-6.78 (m, 3H), 5.12 (t, J=7.0 Hz, 1H), 3.67-3.61 (m, 3H), 3.03 (dd, J=14.0, 9.0 Hz, 1H), 2.82 (dd, J=14.0, 5.5 Hz, 1H), 2.52 (t, J=6.0 Hz, 2H), 2.44 (ddd, J=14.0, 7.5, 7.5 Hz, 1H), 2.28 (ddd, J=14.0, 7.0, 7.0 Hz, 1H), 1.66 (s, 3H), 1.55 (s, 3H), 1.44 (s, 9H).

Step C. 3-({4-[(2R)-2-({5-Chloro-1-[3-(trifluoromethyl)phenyl]-1H-indol-2-yl}carbonyl)-5-methylhexyl]benzoyl}amino)propanoic acid and 3-({4-[(2s)-2-({5-Chloro-1-[3-(trifluoromethyl)phenyl]-1H-indol-2-yl}carbonyl)-5-methylhexyl]benzoyl}amino)propanoic acid To a solution of the title compound of Example 10 Step B (35 mg, 0.05 mmol) in MeOH (2 mL) was added 5% Pt/C (5 mg), and the suspension was placed under an atmosphere of H$_2$. After 1 h, the reaction mixture was filtered through a pad of Celite and concentrated in vacuo: LCMS B, t$_r$=3.17 min, m/z 669.3 [M+H]$^+$. Chiral HPLC purification (ChiralPak AD-H column, 10% iPrOH in heptane, 9 mL/min) provided two isomers, t$_r$=19.9 min and t$_r$=28.2 min. Each amide was separately dissolved in CH$_2$Cl$_2$ (1 mL) and TFA (1 mL) was added. After 30 min, the mixtures were concentrated in vacuo. Purification by reverse phase HPLC (50 to 100% CH$_3$CN in H$_2$O, each with 0.1% v/v TFA) provided the title compounds. The following data are for the more potent glucagon receptor antagonist, which is derived from the first eluting tert-butyl ester enantiomer: LCMS B, t$_r$=2.86 min, m/z 613.2 [M+H]$^+$; $^1$H NMR (500 MHz, d$_6$DMSO) δ 8.40 (t, J=5.5 Hz, 1H), 7.88 (d, J=2.0 Hz, 1H), 7.85 (d, J=8.0 Hz, 1H), 7.76-7.73 (m, 2H), 7.69 (d, J=8.5 Hz, 2H), 7.52-7.43 (m, 2H), 7.33 (dd, J=9.0, 2.0 Hz, 1H), 7.28 (d, J=8.5 Hz, 2H), 7.02 (d, J=9.0 Hz, 1H), 3.85-3.80 (m, 1H), 2.93 (dd, J=13.5, 8.0 Hz, 1H), 2.76 (dd, J=13.5, 6.0 Hz, 1H), 2.46 (t, J=7.0 Hz, 2H), 1.66-1.59 (m, 1H), 1.51-1.43 (m, 1H), 1.21-1.05 (m, 3H), 0.78 (d, J=6.5 Hz, 3H), 0.77 (d, J=6.5 Hz, 3H), α-NH β-alanine methylene group obscured by residual H$_2$O signal.

EXAMPLE 11

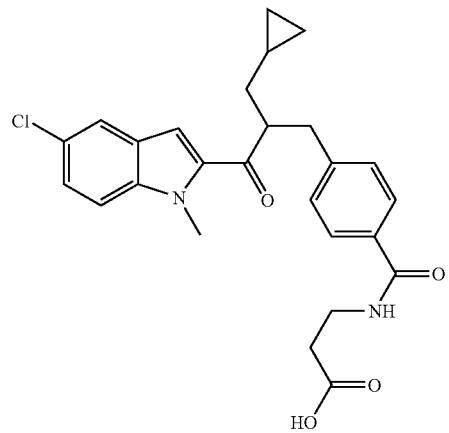

Step A. Ethyl 5-chloro-1-methyl-1H-indole-2-carboxylate

To a solution of ethyl 5-chloroindole-2-carboxylic acid (2.0 g, 8.94 mmol) in DMF (10 mL) was added NaH (393 mg, 60% suspension in mineral oil, 9.8 mmol). After 10 min, iodomethane (0.610 mL, 9.8 mmol) was added, and the mixture was allowed to stir for 22 h, whereupon it was quenched by addition of sat. aq. NaHCO$_3$. The aqueous phase was extracted with EtOAc, and the organic phase was concentrated in vacuo. Purification by flash chromatography on silica gel (0 to 15%, then 15 to 100% EtOAc in hexanes) provided the title compound: LCMS C, t$_r$=2.35 min, m/z 238.2 [M+H]$^+$; $^1$H NMR (500 MHz, CDCl$_3$) δ 7.68 (d, J=1.0 Hz, 1H), 7.37-7.34 (m, 2H), 7.26 (s, 1H), 4.43 (q, J=7.0 Hz, 2H), 4.11 (s, 3H), 1.46(t, J=7.0 Hz, 3H).

Step B. tert-Butyl 3-(5-chloro-1-methyl-1H-indol-2-yl)-3-oxopropanoate

To a cooled (−78° C.) solution of LHMDS (20.1 mL, 1.0 M in THF, 20.1 mmol) in THF (10 mL), was added tert-butyl acetate (2.71 mL, 20.1 mmol). After 30 min, a solution of the title compound of Example 11 Step A (1.59 g, 6.7 mmol) in THF (10 mL) was added. After 30 min, the reaction mixture was placed in a 0° C. bath, and was stirred at this temperature for 3 h, whereupon it was quenched by addition of sat. aq. NaHCO$_3$. The aqueous phase was extracted with EtOAc, and the organic phase was concentrated in vacuo. Purification by flash chromatography on silica gel (0 to 30%, then 30 to 100% EtOAc in hexanes) provided the title compound: LCMS C, t$_r$=2.38 min, m/z 252.2 [M−tBu+H]$^+$; $^1$H NMR (500 MHz, CDCl$_3$) δ 7.66 (d, J=2.0 Hz, 1H), 7.34 (dd, J=9.0, 2.0 Hz, 1H), 7.31 (d, J=9.0 Hz, 1H), 7.21 (s, 1H), 4.06 (s, 3H), 3.87 (s, 2H), 1.49 (s, 9H).

Step C. Methyl 4-[(2RS)-3-(5-chloro-1-methyl-1H-indol-2-yl)-2-(cyclopropylmethyl)-3-oxopropyl]benzoate To a solution of the title compound of Example 11 Step B (454 mg, 1.48 mmol) in DMF (2 mL) was added NaH (71 mg, 60% suspension in mineral oil, 1.77 mmol). After 10 min, bromomethyl cyclopropane (0.172 mL, 1.77 mmol) was added, and the resultant mixture was heated at 60° C. for 16 h. The reaction mixture was allowed to cool to room temperature, then was quenched by addition of sat. aq. NaHCO$_3$. The aqueous phase was extracted with EtOAc, and the organic phase was dried over anhydrous Na$_2$SO$_4$ and concentrated in vacuo: LCMS C, t$_r$=2.70 min, m/z 306.2 [M−tBu+H]$^+$. To a solution of the crude adduct obtained above in DMF (2 mL) was added NaH (89 mg, 60% suspension in mineral oil, 2.22 mmol). After 10 min, a solution of methyl 4-bromomethyl benzoate (508 mg, 2.22 mmol) in DMF (1 mL) was added, and the resultant mixture was stirred for 3 h, whereupon it was quenched by addition of sat. aq. NaHCO$_3$. The aqueous phase was extracted with EtOAc, and the organic phase was dried over anhydrous Na$_2$SO$_4$ and concentrated in vacuo: LCMS C, t$_r$=2.92 min, m/z 454.3 [M−tBu+H]$^+$. The crude adduct obtained above was dissolved in CH$_2$Cl$_2$ (3 mL) and TFA (3 mL) was added. After 3 h, the reaction mixture was concentrated in vacuo. Residual TFA was removed by azeotroping from benzene to provide a crude oil that was dissolved in anhydrous benzene, and heated at 80° C. for 15 h. After cooling to room temperature, the mixture was concentrated in vacuo. Purification by flash chromatography on silica gel (0 to 10%, then 10 to 100% EtOAc in hexanes) provided the title compound: LCMS C, t$_r$=2.72 min, m/z 410.3 [M+H]$^+$; $^1$H NMR (500 MHz, CDCl$_3$) δ 7.89 (d, J=8.0 Hz, 2H), 7.61 (d, J=1.5 Hz, 1H), 7.29 (dd, J=9.0, 1.5 Hz, 1H), 7.28-7.25 (m, 3H), 7.14 (s, 1H), 4.00 (s, 3H), 3.86 (s, 3H), 3.76 (dddd, J=8.5, 8.5, 6.0, 6.0, 1H), 3.18 (dd, J=14.0, 8.5 Hz, 1H), 2.90 (dd, J=14.0, 6.0 Hz, 1H), 1.75 (ddd, J=14.0, 7.5, 7.5 Hz, 1H), 1.52-1.46 (m, 1H), 0.69-0.62 (m, 1H), 0.43-0.37 (m, 1H), 0.36-0.32 (m, 1H), 0.05-(−0.021) (m, 2H).

Step D. 3-({4-[(2R)-3-(5-Chloro-1-methyl-1H-indol-2-yl)-2-(cyclopropylmethyl)-3-oxopropyl]benzoyl}amino)propanoic acid and 3-({4-[(2S)-3-(5-Chloro-1-methyl-1H-indol-2-yl)-2-(cyclopropylmethyl)-3-oxopropyl]benzoyl}amino)propanoic acid To a solution of the title compound of Example 11 Step C (80 mg, 0.20 mmol) in 1,4-dioxane (2 mL) was added 2 N aq. LiOH (1 mL, 2.0 mmol), and the resultant mixture was stirred at 40° C. for 18 h. The mixture was allowed to cool to room temperature whereupon it was quenched by the addition of 2 N aq. HCl. The aqueous phase was extracted with EtOAc, and the organic phase was dried over Na$_2$SO$_4$ and concentrated in vacuo. To the crude carboxylic acid obtained above were added EDC (115 mg, 0.60 mmol), HOBt (81 mg, 0.60 mmol), and β-alanine tert-butyl ester hydrochloride (109 mg, 0.60 mmol). The resultant mixture was dissolved in DMF (1 mL), DIEA (0.212 mL, 1.2 mmol) was added, and the reaction mixture was stirred at 50° C. for 2 h. The reaction mixture was quenched by addition of sat. aq. NaHCO$_3$, and the aqueous phase was extracted with EtOAc. The organic phase was concentrated in vacuo. Purification by flash chromatography on silica gel (0 to 40%, then 40 to 100% EtOAc in hexanes) provided the racemic amide: LCMS C, t$_r$=2.66 min, m/z 467.3 [M−tBu+H]$^+$; $^1$H NMR (500 MHz, CDCl$_3$) δ 7.67 (d, J=8.0 Hz, 2H), 7.66 (s, 1H), 7.33 (d, J=2.0 Hz, 1H), 7.32 (s, 1H), 7.29 (d, J=8.0 Hz, 2H), 7.18 (s, 1H), 6.82 (t, J=5.5 Hz, 1H), 4.04 (s, 3H), 3.80 (dddd, J=8.0, 8.0, 6.0, 6.0 Hz, 1H), 3.68 (q, J=6.0 Hz, 2H), 3.21 (dd, J=13.5, 8.5 Hz, 1H), 2.92 (dd, J=13.5, 6.0 Hz, 1H), 2.56 (t, J=6.0 Hz, 2H), 1.78 (ddd, J=14.0, 7.0, 7.0 Hz, 1H), 1.55-1.50 (m, 1H), 1.48 (s, 9H), 0.73-0.67 (m, 1H), 0.47-0.43 (m, 1H), 0.40-0.36 (m, 1H), 0.088-0.017 (m, 2H). Chiral HPLC purification (ChiralPak OD column, 10% iPrOH in heptane, 9 mL/min) provided two isomers, t$_r$=31.1 min and t$_r$=38.5 min. Each amide was separately dissolved in CH$_2$Cl$_2$ (1 mL) and TFA (1 mL) was added. After 30 min, the mixtures were concentrated in vacuo. Purification by reverse phase HPLC (50 to 100% CH$_3$CN in H$_2$O, each with 0.1% v/v TFA) provided the title compounds. The following data are for the more potent glucagon receptor antagonist, which is derived from the second eluting tert-butyl ester enantiomer: LCMS C, t$_r$=2.29 min, m/z 467.1 [M+H]$^+$; $^1$H NMR (500 MHz, d$_6$DMSO) δ 8.37 (t, J=5.5 Hz, 1H), 7.75 (d, J=2.0 Hz, 1H), 7.67 (d, J=8.0 Hz, 2H), 7.58 (d, J=9.0 Hz, 1H), 7.51 (s, 1H), 7.34 (dd, J=9.0, 2.0 Hz, 1H), 3.96-3.89 (m, 1H), 3.93 (s, 3H), 3.03 (dd, J=14.0, 9.0 Hz, 1H), 2.85 (dd, J=14.0, 6.5 Hz, 1H), 2.45 (t, J=7.0 Hz, 2H), 1.60 (ddd, J=14.0, 8.0, 8.0 Hz, 1H), 1.44 (ddd, J=14.0, 5.5, 5.5 Hz, 1H), 0.67-0.62 (m, 1H), 0.35-0.30 (m, 1H), 0.26-0.21 (m, 1H), −0.017-(−0.07) (m, 2H), α-NH β-alanine methylene group obscured by residual H₂O signal.

EXAMPLE 12

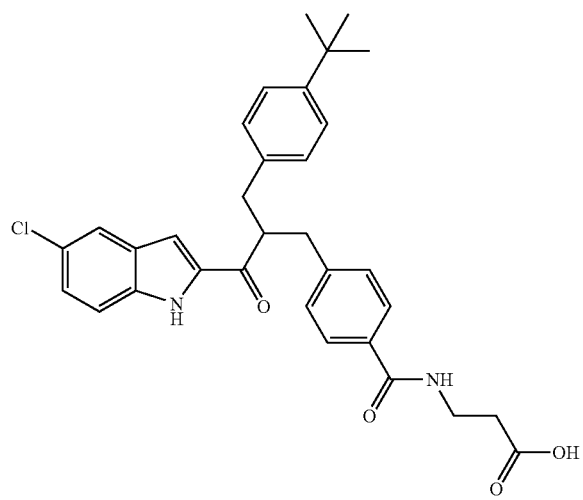

Step A. Ethyl 5-chloro-1-(phenylmethyl)-1H-indole-2-carboxylate

To a solution of ethyl 5-chloroindole-2-carboxylic acid (4.00 g, 17.9 mmol) in DMF (50 mL) was added NaH (787 mg, 60% suspension in mineral oil, 19.7 mmol). After 20 min, benzyl bromide (2.30 mL, 19.7 mmol) was added, and the resultant mixture was stirred for 2 h, whereupon it was quenched by addition of saturated aq. NH₄Cl. The aqueous phase was extracted with EtOAc, and the organic phase was dried over anhydrous Na₂SO₄ and concentrated in vacuo. Purification by flash chromatography on silica gel (0-25%, then 25-75% EtOAc in hexanes) provided the title compound: LCMS A, $t_r$=4.19 min, m/z 314.2 [M+H]⁺; ¹H NMR (500 MHz, CDCl₃) δ 7.67 (d, J=1.5 Hz, 1H), 7.31 (s, 1H), 7.28-7.19 (m, 5H), 7.01 (d, J=7.0 Hz, 2H), 5.83 (s, 2H), 4.33 (q, J=7.0 Hz, 2H), 1.36 (t, J=7.0 Hz, 3H).

Step B. tert-Butyl 3-(1-benzyl-5-chloro-1H-indol-2-yl)-3-oxopropanoate

To a cooled (−78° C.) solution of LHMDS (38 mL, 1.0 M in THF, 38 mmol) was added tert-butyl acetate (5.2 mL, 38.3 mmol). After 30 min, a solution of the title compound of Example 12 Step A (4.00 g, 12.8 mmol) in THF (10 mL) was added, and the mixture was held at −78° C. for 50 min, whereupon it was placed in a 0° C. bath. After 2 h, the reaction mixture was quenched by addition of sat. aq. NH₄Cl, and the aqueous phase was extracted with EtOAc. The organic phase was dried over anhydrous Na₂SO₄ and concentrated in vacuo. Purification by flash chromatography on silica gel (0 to 20%, then 20-100% EtOAc in hexanes) provided the title compound: LCMS B, $t_r$=2.70 min, m/z 328.1 [M−tBu+H]⁺; ¹H NMR (500 MHz, CDCl₃) δ 7.70 (s, 1H), 7.31 (s, 1H), 7.29-7.18 (m, 5H), 7.02 (d, J=7.0 Hz, 2H), 5.84 (s, 2H), 3.86 (s, 2H), 1.40 (s, 9H).

Step C. Methyl 4-[(2RS)-3-(1-benzyl-5-chloro-1H-indol-2-yl)-2-(4-tert-butylbenzyl)-3-oxopropyl]benzoate To a solution of the title compound of Example 12 Step B (300 mg, 0.75 mmol) in DMF (3.5 mL) was added NaH (33 mg, 60% suspension in mineral oil, 0.83 mmol). After 10 min, 4-tert-butylbenzyl bromide (0.152 mL, 0.83 mmol) was added, and the resultant mixture was stirred for 1.5 h. The reaction mixture was quenched by addition of sat. aq. NH₄Cl. The aqueous phase was extracted with EtOAc, and the organic phase was dried over anhydrous Na₂SO₄ and concentrated in vacuo: LCMS A, $t_r$=4.54 min, m/z 474.4 [M−tBu+H]⁺. To a solution of the crude adduct obtained above in DMF (3 mL) was added NaH (45 mg, 60% suspension in mineral oil, 1.13 mmol). After 10 min, a solution of methyl 4-bromomethyl benzoate (259 mg, 1.13 mmol) in DMF (0.5 mL) was added, and the resultant mixture was stirred for 4 h, whereupon it was quenched by addition of sat. aq. NH₄Cl. The aqueous phase was extracted with EtOAc, and the organic phase was dried over anhydrous Na₂SO₄ and concentrated in vacuo LCMS A, $t_r$=4.70 min, m/z 622.5 [M−tBu+H]⁺. The crude adduct obtained above was dissolved in CH₂Cl₂ (3 mL) and TFA (3 mL) was added. After 1 h, the reaction mixture was concentrated in vacuo. Residual TFA was removed by azeotroping from benzene to provide a crude oil that was dissolved in anhydrous benzene (3 mL), and heated at 80° C. for 15 h. After cooling to room temperature, the mixture was concentrated in vacuo. Purification by flash chromatography on silica gel (0 to 20%, then 20 to 100% EtOAc in hexanes) provided the title compound: LCMS A, $t_r$=4.55 min, m/z 578.5 [M+H]⁺; ¹H NMR (500 MHz, CDCl₃) δ 7.81 (d, J=8.0 Hz, 2H), 7.57 (s, 1H), 7.24-7.20 (m, 7H), 7.11 (d, J=8.5 Hz, 2H), 7.03 (d, J=8.5 Hz, 2H), 6.99 (s, 1H), 6.87-6.85 (m, 2H), 5.77 (ABq, J=16.0 Hz, Δν=50.0 Hz, 2H), 3.89-3.85 (m, 1H), 3.86 (s, 3H), 3.10 (dd, J=14.0, 8.0 Hz, 1H), 3.04 (dd, J=14.0, 9.0 Hz, 1H), 2.82 (dd, J=13.5, 5.0 Hz, 1H), 2.73 (dd, J=13.5, 7.0 Hz, 1H), 1.24 (s, 9H).

Step D. Methyl 4-[(2RS)-2-(4-tert-butylbenzyl)-3-(5-chloro-1H-indol-2-yl)-3-oxopropyl]benzoate To a cooled (0° C.) flask containing AlCl₃ (622 mg, 4.66 mmol) was added a solution of the title compound of Example 12 Step C (674 mg, 1.17 mmol) and anisole (0.253 mL, 2.33 mmol) in toluene (3 mL). After 30 min, the mixture was removed from the 0° C. bath and allowed to stir at room temperature for 1.5 h, whereupon it was poured into H₂O. The aqueous phase was extracted with EtOAc, and the organic phase was concentrated in vacuo. Purification by flash chromatography on silica gel (0 to 30%, then 30 to 100% EtOAc in hexanes) provided the title compound: LCMS E, $t_r$=4.50 min, m/z 488.2 [M+H]⁺; ¹H NMR (500 MHz, CDCl₃) δ 8.92 (s, 1H), 7.86 (d, J=8.5 Hz, 2H), 7.57 (s, 1H), 7.29-7.25 (m, 2H), 7.23 (d, J=7.0 Hz, 2H), 7.20 (d, J=8.5 Hz, 2H), 7.08 (d, J=8.0 Hz, 2H), 6.86 (d, J=2.0 Hz, 1H), 3.86-3.81 (m, 1H), 3.85 (s, 3H), 3.20 (dd, J=14.0, 9.0 Hz, 1H), 3.13 (dd, J=14.0, 7.5 Hz, 1H), 2.92 (dd, J=13.5, 5.5 Hz, 1H), 2.83 (dd, J=13.5, 7.0 Hz, 1H), 1.23 (s, 9H).

Step E. 3-({4-[(2R)-2-(4-tert-Butylbenzyl)-3-(5-chloro-1H-indol-2-yl)-3-oxopropyl]benzoyl}amino) propanoic acid and 3-({4-[(2S)-2-(4-tert-Butylbenzyl)-3-(5-chloro-1H-indol-2-yl)-3-oxopropyl] benzoyl}amino)propanoic acid To a solution of the title compound of Example 12 Step D (175 mg, 0.36 mmol) in 1,4-dioxane (2 mL) was added LiOH (86.0 mg, 3.59 mmol), and the resultant mixture was stirred at 40° C. for 18 h. The mixture was allowed to cool to room temperature whereupon it was quenched by the addition of 2 N aq. HCl. The aqueous phase was extracted with EtOAc, and the organic phase was dried over $Na_2SO_4$ and concentrated in vacuo. To the crude carboxylic acid obtained above were added EDC (206 mg, 1.08 mmol), HOBt (146 mg, 1.08 mmol), and β-alanine tert-butyl ester hydrochloride (196 mg, 1.08 mmol). The resultant mixture was dissolved in DMF (2 mL), DIEA (0.624 mL, 3.53 mmol) was added, and the reaction mixture was stirred at 50° C. for 2 h. The reaction mixture was quenched by addition of sat. aq. $NaHCO_3$, and the aqueous phase was extracted with EtOAc. The organic phase was concentrated in vacuo. Purification by flash chromatography on silica gel (0 to 50%, then 50 to 100% EtOAc in hexanes) provided the racemic amide: LCMS B, $t_r$=2.81 min, m/z 601.3 $[M+H]^+$. Chiral HPLC purification (ChiralPak OD column, 15% iPrOH in heptane, 9 mL/min) provided two isomers, $t_r$=23.1 min and $t_r$=29.5 min. Each amide was separately dissolved in $CH_2Cl_2$ (1 mL) and TFA (1 mL) was added. After 45 min, the mixtures were concentrated in vacuo. Purification by reverse phase HPLC (30 to 100% $CH_3CN$ in $H_2O$, each with 0.1% v/v TFA) provided the title compounds. The following data are for the more potent glucagon receptor antagonist, which is derived from the second eluting tert-butyl ester enantiomer: LCMS A, $t_r$=3.92 min, m/z 545.2 $[M+H]^+$; $^1$H NMR (500 MHz, $d_6$-DMSO) δ 8.38 (t, J=5.5 Hz, 1H), 7.67 (s, 1H), 7.66 (d, J=8.0 Hz, 2H), 7.36 (d, J=9.0 Hz, 1H), 7.30 (d, J=2.0 Hz, 1H), 7.29 (d, J=8.0 Hz, 2H), 7.23 (dd, J=9.0, 2.0 Hz, 1H), 7.19 (d, J=8.5 Hz, 2H), 7.10 (d, J=8.5 Hz, 2H), 4.14-4.10 (m, 1H), 3.08 (dd, J=13.5, 8.5 Hz, 1H), 3.00 (d, J=13.5, 8.5 Hz, 1H), 2.83 (dd, J=14.0, 6.0 Hz, 1H), 2.74 (dd, J=14.0, 6.0 Hz, 1H), 2.45 (t, J=7.5 Hz, 2H), 1.16 (s, 9H), α-NH β-alanine methylene group obscured by residual $H_2O$ signal.

EXAMPLE 13

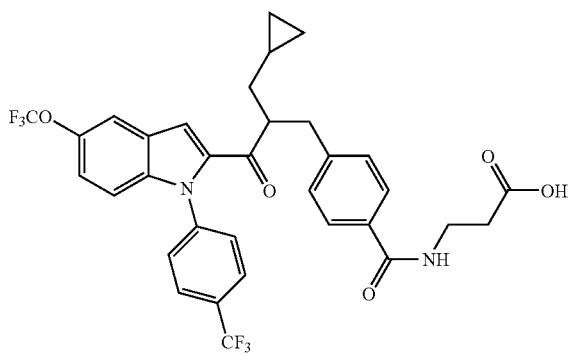

Step A. Ethyl 5-[(trifluoromethyl)oxy]-1-[4-(trifluoromethyl)phenyl]-1H-indole-2-carboxylate To a vial containing ethyl 5-trifluoromethoxyindole-2-carboxylic acid (500 mg, 1.83 mmol) were added 4-iodobenzotrifluoride (323 mg, 2.20 mmol), potassium phosphate (815 mg, 3.84 mmol), copper iodide (17.5 mg, 0.092 mmol), and trans N,N'-dimethyl-1,2-cyclohexanediamine (0.058 mL, 0.37 mmol). The resulting mixture was purged with $N_2$, and degassed toluene (2 mL) was added. The reaction mixture was capped, placed in a 110° C. bath, and was stirred for 18 h. Upon cooling to room temperature, the mixture was filtered and concentrated in vacuo. Purification by flash chromatography on silica gel (0 to 30% then 30 to 100% EtOAc in hexanes) gave the title compound: LCMS A, $t_r$=4.28 min, m/z 418.1 $[M+H]^+$; $^1$H NMR (500 MHz, $CDCl_3$) δ 7.80 (d, J=8.5 Hz, 2H), 7.60 (s, 1H), 7.48 (s, 1H), 7.47 (d, J=8.5 Hz, 2H), 7.17 (dd, J=9.0, 1.5 Hz, 1H), 7.07 (d, J=9.0 Hz, 1H), 4.25 (q, J=7.0 Hz, 2H), 1.25 (t, J=7.0 Hz, 3H).

Step B. tert-Butyl 3-oxo-3-{5-(trifluoromethoxy)-1-[4-(trifluoromethyl)phenyl]-1H-indol-2-yl}propanoate To a cooled (−78° C.) solution of LHMDS (4.5 mL, 1.0 M in THF, 4.5 mmol) in THF (13 mL) was added tert-butyl acetate (0.600 mL, 4.46 mmol), dropwise. After 30 min, a solution of the title compound of Example 13 Step A (620 mg, 1.50 mmol) in THF (4 mL) was added, and the mixture was held at −78° C. for 30 min, then was placed in a 0° C. bath. After 1.5 h, the reaction mixture was poured into sat. aq. $NaHCO_3$ and extracted twice with EtOAc. The combined organic phases were concentrated in vacuo. Purification by flash chromatography on silica gel (0 to 30%, then 30 to 100% hexanes in EtOAc) afforded the title compound: LCMS B, $t_r$=2.90 min, m/z 432.0 $[M-tBu+H]^+$; $^1$H NMR (500 MHz, $CDCl_3$) δ 7.79 (d, J=8.5 Hz, 2H), 7.64 (s, 1H), 7.46 (s, 1H), 7.44 (d, J=8.5 Hz, 2H), 7.21 (dd, J=9.0, 2.0 Hz, 1H), 7.11 (d, J=9.0 Hz, 1H), 3.85 (s, 2H), 1.46 (s, 9H).

Step C. tert-Butyl 3-{[4-((2RS)-2-(cyclopropylmethyl)-3-oxo-3-{5-(trifluoromethoxy)-1-[4-(trifluoromethyl)phenyl]-1H-indol-2-yl}propyl)benzoyl]amino}propanoate To a solution of the title compound of Example 13 Step B (368 mg, 0.76 mmol) in DMF (2 mL) was added NaH (33 mg, 60% suspension in mineral oil, 0.83 mmol). After 10 min, bromomethyl cyclopropane (0.081 mL, 0.83 mmol) was added, and the resultant mixture was heated at 60° C. for 16 h. The reaction mixture was allowed to cool to room temperature, then was quenched by addition of sat. aq. $NaHCO_3$. The aqueous phase was extracted with EtOAc, and the organic phase was dried over anhydrous $Na_2SO_4$ and concentrated in vacuo. To a solution of the crude adduct obtained above in DMF (2 mL) was added NaH (46 mg, 60% suspension in mineral oil, 1.14 mmol). After 10 min, a solution of methyl 4-bromomethyl benzoate (261 mg, 1.14 mmol) in DMF (1 mL) was added, and the resultant mixture was stirred for 3 h, whereupon it was quenched by addition of sat. aq. $NaHCO_3$. The aqueous phase was extracted with EtOAc, and the organic phase was dried over anhydrous $Na_2SO_4$ and concentrated in vacuo: LCMS A, $t_r$=4.71 min, m/z 634.3 $[M-tBu+H]^+$. The crude adduct obtained above was dissolved in $CH_2Cl_2$ (3 mL) and TFA (3 mL) was added. After 4 h, the reaction mixture was concentrated in vacuo. Residual TFA was removed by azeotroping from benzene to provide a crude oil that was dissolved in anhydrous benzene, and heated at 80° C. for 15 h. After cooling to room temperature, the mixture was concentrated in vacuo. Purification by flash chromatography on silica gel (0 to 10%, then 10 to 100% EtOAc in hexanes) provided an oil: LCMS B, $t_r$=3.09 min, m/z 590.1 $[M+H]^+$. The compound obtained above was dissolved in 1,4-dioxane (3 mL). 2 N aq. LiOH (1.9 mL, 3.9 mmol) was added, and the resultant mixture was stirred at 40° C. for 24 h. The mixture was allowed to cool to room temperature whereupon it was quenched by the addition of 2 N aq. HCl. The aqueous phase was extracted with EtOAc, and the organic phase was dried over $Na_2SO_4$ and concentrated in vacuo. To the crude carboxylic acid obtained above were added EDC (435 mg, 2.28 mmol), HOBt (308 mg, 2.28 mmol), and β-alanine tert-butyl ester hydrochloride (413 mg, 2.28 mmol). The resultant mixture was dissolved in DMF (3 mL), DIEA (0.800 mL, 4.56 mmol) was added, and the reaction mixture was stirred at 50° C. for 2 h. The reaction mixture was quenched by addition of sat. aq. NaHCO$_3$, and the aqueous phase was extracted with EtOAc. The organic phase was concentrated in vacuo. Purification by flash chromatography on silica gel (0 to 40%, then 40 to 100% EtOAc in hexanes) provided the title compound: LCMS D, t$_r$=1.45 min, m/z 647.5 [M−tBu+H]$^+$; $^1$H NMR (500 MHz, CDCl$_3$) δ 7.76 (d, J=8.5 Hz, 2H), 7.64 (d, J=8.5 Hz, 2H), 7.59 (s, 1H), 7.40 (s, 1H), 7.26-7.20 (m, 2H), 7.22 (d, J=8.0 Hz, 2H), 7.16 (d, J=9.0 Hz, 1H), 7.00 (d, J=9.0 Hz, 1H), 6.85 (t, J=5.5 Hz, 1H), 3.79 (dddd, J=9.0, 9.0, 5.5, 5.5 Hz, 1H), 3.65 (q, J=6.0 Hz, 2H), 3.06 (dd, J=13.5, 9.0, 1H), 2.86 (dd, J=13.5, 5.5 Hz, 1H), 2.53 (t, J=6.0 Hz, 2H), 1.74-1.68 (m, 1H), 1.49-1.44 (m, 1H), 1.44 (s, 9H), 0.71-0.65 (m, 1H), 0.49-0.44 (m, 1H), 0.42-0.37 (m, 1H), 0.08-0.01 (m, 2H).

Step D. 3-{[4-((2R)-2-(cyclopropylmethyl)-3-oxo-3-{5-(trifluoromethoxy)-1-[4-(trifluoromethyl)phenyl]-1H-indol-2-yl}propyl)benzoyl]amino}propanoic acid and 3-{[4-((2S)-2-(cyclopropylmethyl)-3-oxo-3-{5-(trifluoromethoxy)-1-[4-(trifluoromethyl)phenyl]-1H-indol-2-yl}propyl)benzoyl]amino}propanoic acid Chiral HPLC purification of the title compound of Example 13 Step C (ChiralPak AD-H column, 10% iPrOH in heptane, 9 mL/min) provided two isomers, t$_r$=27.8 min and t$_r$=32.6 min. Each was separately dissolved in CH$_2$Cl$_2$ (1 mL) and TFA (1 mL) was added. After 30 min, the mixtures were concentrated in vacuo. Purification by reverse phase HPLC (50 to 100% CH$_3$CN in H$_2$O, each with 0.1% v/v TFA) provided the title compounds. The following data are for the more potent glucagon receptor antagonist, which is derived from the first eluting tert-butyl ester enantiomer: LCMS D t$_r$=1.34 min, m/z 647.5 [M+H]$^+$; $^1$H NMR (500 MHz, d$_6$DMSO) δ 8.41 (t, J=5.5 Hz, 1H), 7.89 (s, 1H), 7.87 (d, J=9.0 Hz, 1H), 7.84 (s, 1H), 7.70 (d, J=8.0 Hz, 2H), 7.38 (m, 2H), 7.30-7.27 (m, 2H), 7.28 (d, J=8.0 Hz, 2H), 7.12 (d, J=9.0 Hz, 1H), 4.00-3.95 (m, 1H), 3.39 (q, J=7.0 Hz, 2H), 2.95 (dd, J=13.5, 8.5 Hz, 1H), 2.83 (dd, J=13.5, 6.0 Hz, 1H), 2.46 (t, J=7.0 Hz, 2H), 1.61-1.55 (m, 1H), 1.41-1.36 (m, 1H), 0.71-0.66 (m, 1H), 0.40-0.29 (m, 2H), 0.05-0.00 (m, 1H), −0.03-(−0.07) (m, 1H).

EXAMPLE 14

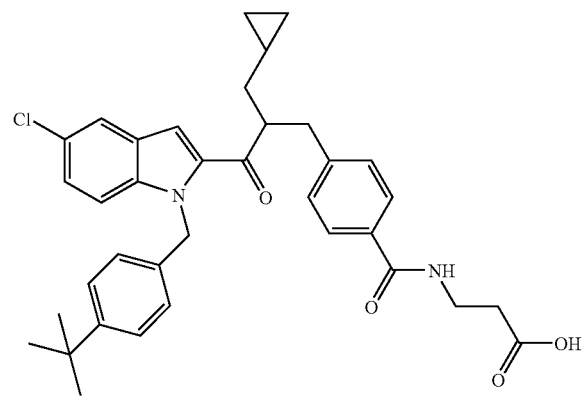

Step A. Ethyl 1-(4-tert-butylbenzyl)-5-chloro-1H-indole-2-carboxylate

To a solution of ethyl 5-chloroindole-2-carboxylate (4.50 g, 20.1 mmol) in DMF (50 mL) was added NaH (885 mg, 60% suspension in mineral oil, 22.1 mmol). After 20 min, 4-tert-butylbenzyl bromide (4.07 mL, 22.1 mmol) was added. After 3 h, the reaction mixture was quenched by addition of sat. aq. NH$_4$Cl. The aqueous phase was extracted with EtOAc, and the organic phase was dried over anhydrous Na$_2$SO$_4$ and concentrated in vacuo. Purification by flash chromatography on silica gel (0 to 20%, then 20 to 100% EtOAc in hexanes) provided the title compound: LCMS B, t$_r$=3.18 min, m/z 370.2 [M+H]$^+$; $^1$H NMR (500 MHz, CDCl$_3$) δ 7.71 (d, J=2.0 Hz, 1H), 7.35 (s, 1H), 7.33-7.27 (m, 4H), 7.01 (d, J=8.0 Hz, 2H), 5.84 (s, 2H), 4.38 (q, J=7.0 Hz, 2H), 1.41 (t, J=7.0 Hz, 3H), 1.30 (s, 9H).

Step B. tert-Butyl 3-[1-(4-tert-butylbenzyl)-5-chloro-1H-indol-2-yl]-3-oxopropanoate To a cooled (−78° C.) solution of LHMDS (36.5 mL, 1.0 M in THF, 36.5 mmol) was added tert-butyl acetate (4.92 mL, 36.5 mmol), dropwise. After 30 min, a solution of the title compound of Example 14 Step A (4.50 g, 12.2 mmol) in THF (12 mL) was added, and the mixture was held at −78° C. for 30 min, then was placed in a 0° C. bath. After 1.5 h, the reaction mixture was poured into sat. aq. NH$_4$Cl and extracted twice with ethyl acetate. The combined organic phases were dried over anhydrous Na$_2$SO$_4$ and concentrated in vacuo. Purification by flash chromatography on silica gel (0 to 20%, then 20 to 100% EtOAc in hexanes) afforded the title compound: LCMS B, t$_r$=3.11 min, m/z 462.2 [M+Na]$^+$; $^1$H NMR (500 MHz, CDCl$_3$) δ 7.69 (d, J=2.0 Hz, 1H), 7.31-7.24 (m, 5H), 6.97 (d, J=8.5 Hz, 2H), 5.80 (s, 2H), 3.85 (s, 2H), 1.39 (s, 9H), 1.25 (s, 9H).

Step C. Methyl 4-[(2SR)-3-[1-(4-tert-butylbenzyl)-5-chloro-1H-indol-2-yl]-2-cyclopropylmethyl)-3-oxopropyl]benzoate To a solution of the title compound of Example 14 Step B (634 mg, 1.44 mmol) in DMF (7.0 mL) was added NaH (63 mg, 60% suspension in mineral oil, 1.59 mmol). After 10 min, bromomethyl cyclopropane (0.154 mL, 1.59 mmol) was added, and the resultant mixture was stirred for 12 h at room temperature, then 3 h at 60° C. The reaction mixture was quenched by addition of sat. aq. NH$_4$Cl. The aqueous phase was extracted with EtOAc, and the organic phase was dried over anhydrous Na$_2$SO$_4$ and concentrated in vacuo: LCMS B, t$_r$=3.45 min, m/z 516.2 [M+Na]$^+$. To a solution of the crude adduct obtained above in DMF (5 mL) was added NaH (86 mg, 60% suspension in mineral oil, 2.16 mmol). After 10 min, a solution of methyl 4-bromomethyl benzoate (495 mg, 2.16 mmol) in DMF (1.0 mL) was added, and the resultant mixture was stirred for 16 h, whereupon it was quenched by addition of sat. aq. NH$_4$Cl. The aqueous phase was extracted with EtOAc, and the organic phase was dried over anhydrous Na$_2$SO$_4$ and concentrated in vacuo: LCMS A, t$_r$=3.82 min, m/z 586.3 [M−tBu+H]$^+$. The crude adduct obtained above was dissolved in CH$_2$Cl$_2$ (3 mL) and TFA (3 mL) was added. After 1 h, the reaction mixture was concentrated in vacuo.

Residual TFA was removed by azeotroping from benzene to provide a crude oil that was dissolved in anhydrous benzene (10 mL), and heated at 80° C. for 15 h. After cooling to room temperature, the mixture was concentrated in vacuo. Purification by flash chromatography on silica gel (0 to 20%, then 20 to 100% EtOAc in hexanes) provided the title compound: LCMS B, $t_r$=3.06 min, m/z 542.2 [M+H]$^+$; $^1$H NMR (500 MHz, CDCl$_3$) δ 7.83 (d, J=8.5 Hz, 2H), 7.63 (s, 1H), 7.28-7.20 (m, 5H), 6.15 (d, J=8.0 Hz, 2H), 6.82 (d, J=8.0 Hz, 2H), 5.76 (ABq, J=16.5 Hz, Δv=83.6 Hz, 2H), 3.86 (s, 3H), 3.75 (dddd, J=9.0, 9.0, 5.5, 5.5 Hz, 1H), 3.09 (dd, J=13.5, 9.0 Hz, 1H), 2.83 (dd, J=13.5, 5.5 Hz, 1H), 1.71-1.65 (m, 1H), 1.42-1.37 (m, 1H), 1.25 (s, 9H), 0.57-0.51 (m, 1H), 0.36-0.32 (m, 1H), 0.28-0.23 (m, 1H), -0.03-(-0.10) (m, 2H).

Step D. 3-({4-[(2R)-3-[1-(4-tert-Butylbenzyl)-5-chloro-1H-indol-2-yl]-2-(cyclopropylmethyl)-3-oxopropyl]benzoyl}amino)propanoic acid and 3-({4-[(2S)-3-[1-(4-tert-Butylbenzyl)-5-chloro-1H-indol-2-yl]-2-(cyclopropylmethyl)-3-oxopropyl]benzoyl}amino)propanoic acid To a solution of the title compound of Example 14 Step C (200 mg, 0.37 mmol) in 1,4-dioxane (2 mL) was added a solution of LiOH (88.0 mg, 3.7 mmol) in H$_2$O (2 mL), and the resultant mixture was stirred at 50° C. for 3 h. The mixture was allowed to cool to room temperature whereupon it was quenched by the addition of 2 N aq. HCl. The aqueous phase was extracted with EtOAc, and the organic phase was dried over Na$_2$SO$_4$ and concentrated in vacuo. To the crude carboxylic acid obtained above were added EDC (213 mg, 1.12 mmol), HOBt (150 mg, 1.12 mmol), and β-alanine tert-butyl ester hydrochloride (202 mg, 1.12 mmol). The resultant mixture was dissolved in DMF (2 mL), DIEA (0.643 mL, 3.63 mmol) was added, and the reaction mixture was stirred at 50° C. for 4 h. The reaction mixture was quenched by addition of sat. aq. NH$_4$Cl, and the aqueous phase was extracted with EtOAc. The organic phase was concentrated in vacuo. Purification by flash chromatography on silica gel (0 to 50%, then 50 to 100% EtOAc in hexanes) provided the racemic amides: LCMS A, $t_r$=4.66 min, m/z 599.4 [M−tBu+H]$^+$. Chiral HPLC purification (ChiralCel OD column, 10% iPrOH in heptane, 9 mL/min) provided two isomers, $t_r$=23.9 min and $t_r$=30.3 min. Each was separately dissolved in CH$_2$Cl$_2$ (1 mL) and TFA (1 mL). After 30 min, the mixtures were concentrated in vacuo. Purification by reverse phase HPLC (50 to 100% CH$_3$CN in H$_2$O, each with 0.1% v/v TFA) provided the title compounds. The following data are for the more potent glucagon receptor antagonist, which is derived from the second eluting tert-butyl ester enantiomer: LCMS A, $t_r$=4.35 min, m/z 599.1 [M+H]$^+$; $^1$H NMR (500 MHz, d$_6$ DMSO) δ 8.41 (t, J=5.5 Hz, 1H), 7.80 (d, J=2.0 Hz, 1H), 7.68 (d, J=8.0 Hz, 2H), 7.67 (s, 1H), 7.58 (d, J=9.0 Hz, 1H), 7.32 (dd, J=9.0, 2.0 Hz, 1H), 7.28 (d, J=8.0 Hz, 2H), 7.17 (d, J=8.5 Hz, 2H), 6.74 (d, J=8.5 Hz, 2H), 5.79 (ABq, J=16.0 Hz, Δv=112 Hz, 2H), 4.04-4.01 (m, 1H), 3.41 (q, J=7.0 Hz, 2H), 2.99 (dd, J=13.5, 8.5 Hz, 1H), 2.86 (dd, J=13.5, 6.0 Hz, 1H), 2.47 (t, J=7.0 Hz, 2H), 1.60-1.55 (m, 1H), 1.41-1.36 (m, 1H), 0.57-0.53 (m, 1H), 0.30-0.26 (m, 1H), 0.23-0.19 (m, 1H), -0.014-(-0.05) (m, 1H), -0.08-(-0.11) (m, 1H).

EXAMPLE 15

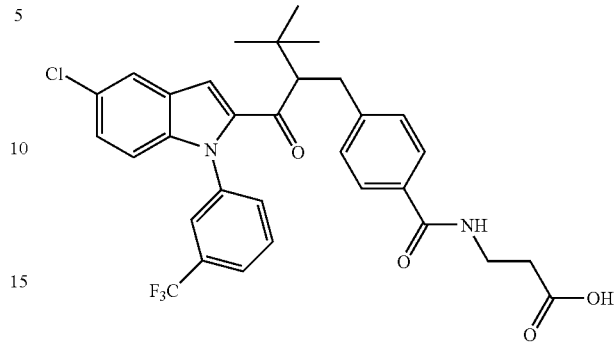

Step A. Methyl 2(RS)-2-({5-chloro-1-[3-(trifluoromethyl)phenyl]-1H-indol-2-yl}carbonyl)-3,3-dimethylbutanoate To a cooled (−78° C.) solution of LHMDS (4.1 mL, 1.0 M in THF, 4.1 mmol) was added methyl tert-butyl acetate (0.616 mL, 4.11 mmol), dropwise. After 30 min, a solution of the title compound of Example 9 Step A (504 mg, 1.37 mmol) in THF (5 mL) was added, and the mixture was held at −78° C. for 30 min, then was placed in a 0° C. bath. After 1.5 h, the reaction mixture was poured into sat. aq. NH$_4$Cl and extracted twice with ethyl acetate. The combined organic phases were dried over anhydrous Na$_2$SO$_4$ and concentrated in vacuo. Purification by flash chromatography on silica gel (0 to 20%, then 20 to 100% hexanes in ethyl acetate) afforded the title compound: LCMS A, $t_r$=4.20 min, m/z 396.2 [M+H]$^+$; $^1$H NMR (500 MHz, CDCl$_3$) δ 7.74 (d, J=2.0 Hz, 1H), 7.72 (d, J=9.0 Hz, 1H), 7.65 (t, J=7.5 Hz, 1H), 7.50 (s, 1H), 7.43 (d, J=9.0 Hz, 1H), 7.39 (s, 1H), 7.28 (dd, J=9.0, 2.0 Hz, 1H), 7.01 (d, J=9.0 Hz, 1H), 4.21 (s, 1H), 3.69 (s, 3H), 1.14 (s, 9H).

Step B. 1-{5-Chloro-1-[3-(trifluoromethyl)phenyl]-1H-indol-2-yl}-3,3-dimethylbutan-1-one To a solution of the title compound of Example 15 Step A (420 mg, 0.93 mmol) in DMSO (5 mL) were added LiCl (390 mg, 9.3 mmol) and H$_2$O (0.067 mL, 3.72 mmol) and the mixture was stirred at 140° C. for 18 h. The mixture was allowed to cool to room temperature, then was diluted with ether and washed with sat. aq. NaHCO$_3$. The organic phase was concentrated in vacuo. Purification by reverse phase HPLC (70 to 100% CH$_3$CN in H$_2$O) provided the title compound: LCMS A, $t_r$=4.28 min, m/z 394.2 [M+H]$^+$; $^1$H NMR (500 MHz, CDCl$_3$) δ 7.73 (d, J=2.0 Hz, 1H), 7.72 (d, J=8.0 Hz, 1H), 7.65 (d, J=7.5 Hz, 1H), 7.50 (s, 1H), 7.46 (d, J=8.0 Hz, 1H), 7.26 (dd, J=9.0, 2.0 Hz, 1H), 6.96 (d, J=9.0 Hz, 1H), 2.78 (s, 2H), 1.06 (s, 9H).

Step C. 3-({4-[(2RS)-2-({5-Chloro-1-[3-(trifluoromethyl)phenyl]-1H-indol-2-yl}carbonyl)-3,3-dimethylbutyl]benzoyl}amino)propanoic acid To a cooled (−78° C.) solution of the title compound of Example 15 Step B (65.0 mg, 0.17 mmol) in THF (1 mL) was added KHMDS (0.660 mL, 0.5 M in toluene, 0.33 mmol). After 30 min, methyl 4-bromomethylbenzoate (76.0 mg, 0.33 mmol) was added, and the resultant mixture was allowed to warm slowly to room temperature over 15 h. The mixture was then quenched by addition of sat. aq. NaHCO$_3$, and the aqueous phase was extracted with EtOAc. The organic phase was dried over anhydrous Na$_2$SO$_4$, and concentrated in vacuo. LCMS A, t$_r$=4.40 min, m/z 542.4 [M+H]$^+$. To a solution of the crude adduct obtained above in 1,4-dioxane (2 mL) was added a solution of LiOH (1 mL, 2.0 N in H$_2$O, 2.0 mmol), and the resultant mixture was stirred at 50° C. for 2 h. The mixture was allowed to cool to room temperature whereupon it was quenched by the addition of 2 N aq. HCl. The aqueous phase was extracted with EtOAc, and the organic phase was dried over Na$_2$SO$_4$ and concentrated in vacuo. To the crude carboxylic acid obtained above were added EDC (96.0 mg, 0.50 mmol), HOBt (68.0 mg, 0.50 mmol), and β-alanine tert-butyl ester hydrochloride (91.0 mg, 0.50 mmol). The resultant mixture was dissolved in DMF (1 mL), DIEA (0.177 mL, 1.0 mmol) was added, and the reaction mixture was stirred at 50° C. for 4 h. The reaction mixture was quenched by addition of sat. aq. NH$_4$Cl, and the aqueous phase was extracted with EtOAc. The organic phase was concentrated in vacuo. Purification by flash chromatography on silica gel (0 to 50%, then 50 to 100% EtOAc in hexanes) provided the amide product: LCMS A, t$_r$=4.31 min, m/z 599.4 [M−tBu+H]$^+$. The amide obtained above was dissolved in CH$_2$Cl$_2$ (1 mL) and TFA (1 mL). After 30 min, the mixture was concentrated in vacuo. Purification by reverse phase HPLC (75 to 100% CH$_3$CN in H$_2$O, each with 0.1% v/v TFA) provided the title compound: LCMS A, t$_r$=3.90 min, m/z 599.4 [M+H]$^+$; $^1$H NMR (500 MHz, d$_6$DMSO) δ 8.35 (t, J=5.5 Hz, 1H), 7.85 (d, J=8.5 Hz, 1H), 7.81 (d, J=2.0 Hz, 1H), 7.74 (t, J=8.0 Hz, 1H), 7.66 (s, 1H), 7.63 (d, J=8.0 Hz, 2H), 7.28 (dd, J=9.0, 2.0 Hz, 1H), 7.21 (d, J=8.0 Hz, 2H), 6.92 (d, J=9.0 Hz, 1H), 3.81-3.77 (m, 1H), 2.94-2.83 (m, 2H), 2.42 (t, J=7.0 Hz, 2H), 1.02 (s, 9H), α-NH β-alanine methylene group obscured by residual H$_2$O signal.

EXAMPLE 16

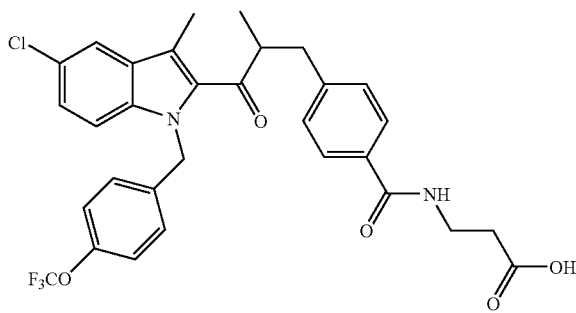

Step A. 1-[5-Chloro-3-methyl-1-({4-[(trifluoromethyl)oxy]phenyl}methyl)-1H-indol-2-yl]propan-1-one To a cooled (−78° C.) solution of 2-amino-5-chloro-N-methoxy-N-methylbenzamide (2.56 g, 11.9 mmol) in THF (20 mL) was added methyllithium (15.7 mL, 1.6 M in ether, 25.0 mmol). After 2 h, the reaction mixture was quenched by addition of 1 N HCl. The aqueous phase was extracted with EtOAc, and the organic phase was concentrated in vacuo: LCMS B, t$_r$=1.85 min, m/z 170.1 [M+H]$^+$. A solution of the methyl ketone obtained above (642 mg, 3.79 mmol) and 1-bromo-2-butanone (0.390 mL, 3.79 mmol) in DMF (9.5 mL) was stirred at 85° C. for 12 h. The mixture was then diluted with EtOAc, and the organic phase was washed with sat. aq. NaHCO$_3$ and concentrated in vacuo. The crude product was dissolved in DMF (5 mL), and NaH (71.0 mg, 60% suspension in mineral oil, 1.78 mmol) was added. After 10 min, 4-trifluoromethoxybenzyl bromide (285 mL, 1.78 mmol) was added, and mixture was allowed to stir for 2 h, whereupon it was quenched by addition of sat. aq. NaHCO$_3$. The aqueous phase was extracted with EtOAc, and the organic phase was concentrated in vacuo. Purification by flash chromatography on silica gel (0 to 10%, then 10 to 100% EtOAc in hexanes) provided the title compound: LCMS B, t$_r$=2.80 min, m/z 396.1 [M+H]$^+$; $^1$H NMR (500 MHz, CDCl$_3$) δ 7.68 (d, J=2.0 Hz, 1H), 7.28 (dd, J=9.0, 2.0 Hz, 1H), 7.22 (d, J=9.0 Hz, 1H), 7.08-6.94 (m, 4H), 5.67 (s, 2H), 2.91 (q, J=7.5 Hz, 2H), 2.62 (s, 3H), 1.15 (t, J=7.5 Hz, 3H).

Step B. 3-{[4-((2RS)-3-{5-chloro-3-methyl-1-[4-(trifluoromethoxy)benzyl]-1H-indol-2-yl}-2-methyl-3-oxopropyl)benzoyl]amino}propanoic acid To a cooled (−78° C.) solution of the title compound of Example 16 Step A (19.0 mg, 0.048 mmol) in THF (1 mL) was added KHMDS (0.240 mL, 0.5 M in toluene, 0.12 mmol). After 30 min, methyl 4-bromomethylbenzoate (27.0 mg, 0.12 mmol) was added, and the resultant mixture was allowed to warm slowly to room temperature over 15 h. The mixture was then quenched by addition of sat. aq. NaHCO$_3$, and the aqueous phase was extracted with EtOAc. The organic phase was dried over anhydrous Na$_2$SO$_4$, and concentrated in vacuo: LCMS B, t$_r$=2.91 min, m/z 544.1 [M+H]$^+$. To a solution of the crude adduct obtained above in 1,4-dioxane (1 mL) was added a solution of LiOH (0.5 mL, 2.0 N in H$_2$O, 1.0 mmol), and the resultant mixture was stirred at 50° C. for 2 h. The mixture was allowed to cool to room temperature whereupon it was quenched by the addition of 2 N aq. HCl. The aqueous phase was extracted with EtOAc, and the organic phase was dried over Na$_2$SO$_4$ and concentrated in vacuo. To the crude carboxylic acid obtained above were added EDC (60.0 mg, 0.31 mmol), HOBt (43.0 mg, 0.31 mmol), and β-alanine tert-butyl ester hydrochloride (50.0 mg, 0.31 mmol). The resultant mixture was dissolved in DMF (1 mL), DIEA (0.200 mL, 1.13 mmol) was added, and the reaction mixture was stirred at 50° C. for 2 h. The reaction mixture was quenched by addition of sat. aq. NH$_4$Cl, and the aqueous phase was extracted with EtOAc. The organic phase was concentrated in vacuo, then dissolved in CH$_2$Cl$_2$ (1 mL) and TFA (1 mL). After 30 min, the mixture was concentrated in vacuo. Purification by reverse phase HPLC (30 to 100% CH$_3$CN in H$_2$O, each with 0.1% v/v TFA) provided the title compound: LCMS B, t$_r$=2.56 min, m/z 601.2 [M+H]$^+$; $^1$H NMR (500 MHz, d$_6$DMSO) δ 8.41 (t, J=5.5 Hz, 1H), 7.84 (d, J=2.0 Hz, 1H), 7.69 (d, J=8.5 Hz, 2H), 7.56 (d, J=9.0 Hz, 1H), 7.32 (dd, J=9.0, 2.0 Hz, 1H), 7.24-7.21 (m, 4H), 6.95 (d, J=8.5 Hz, 2H), 5.62 (ABq, J=17.0 Hz, Δv=15.4 Hz, 2H), 3.70-3.64 (m, 1H), 3.41 (q, J=7.0 Hz, 2H), 2.97 (dd, J=13.5, 7.0 Hz, 1H), 0.88 (t, J=7.0 Hz, 3H), signals for one benzylic proton, the C3-methyl group, and the α-CO$_2$H β-alanine methylene group were obscured by residual H$_2$O and DMSO peaks.

Legend for Tables 1-3:
Stereochem: The designation "A" refers to a final product derived from the tert-butyl ester enantiomer which shows a positive CD signal at 235 nm. The designation "B" refers to a final product derived from the tert-butyl ester enantiomer which shows a negative CD signal at 235 nm. The designation "C" refers to the first eluting enantiomer on a ChiralPak AD-H column with a supercritical $CO_2$/iPrOH mobile phase. The designation "D" refers to the second eluting enantiomer on a ChiralPak AD-H column with a supercritical $CO_2$/iPrOH mobile phase.

The designation "RAC" refers to a racemic mixture.

In molecules that contain 2 stereogenic centers, "syn or anti" refers to a diastereomerically pure compound, the relative stereochemistry of which has not been determined.

TABLE 1

| Example | $R^1$ | $R^2$ | $C(R^4)_3$ | $R^5$ | Stereo-chem | LCMS conditions, $t_r$ m/z |
|---|---|---|---|---|---|---|
| 17 | 5-OBn | ~CH2-C6H4-OCF3 | n-propyl | H | RAC | LC A, 4.32 687.5(M + 1) |
| 18 | 5-Cl | Me | n-pentyl | H | B | LC B, 2.63 483.3(M + 1) |
| 19 | 5-Cl | Me | n-pentyl | H | A | LC B, 2.63 483.3(M + 1) |
| 20 | 5-Cl | Me | n-propyl | H | B | LC B, 2.39 455.2(M + 1) |
| 21 | 5-Cl | Me | n-propyl | H | A | LC B, 2.39 455.2(M + 1) |
| 22 | 5-Cl | allyl | n-propyl | H | RAC | LC E, 3.80 481.4(M + 1) |
| 23 | 5-Cl | Me | n-pentyl | 3-F | B | LC A, 4.01 501.3(M + 1) |
| 24 | 5-Cl | Me | n-pentyl | 3-F | A | LC A, 4.01 501.3(M + 1) |
| 25 | 5-Cl | Me | n-pentyl | 3-Cl | A | LC A, 4.14 515.5(M + 1) |
| 26 | 5-Cl | ~CH2-C6H4-OCF3 | n-pentyl | H | B | LC C, 2.81 643.3(M + 1) |
| 27 | 5-Cl | ~CH2-C6H4-OCF3 | n-pentyl | H | A | LC C, 2.81 643.3(M + 1) |
| 28 | 5-Cl | Me | ~CH2-cyclobutyl | H | A | LC A, 3.82 481.4(M + 1) |
| 29 | 5-OCF$_3$ | Me | n-propyl | H | B | LC B, 2.45 505.3(M + 1) |
| 30 | 5-OCF$_3$ | Me | n-propyl | H | A | LC B, 2.45 505.3(M + 1) |

TABLE 1-continued
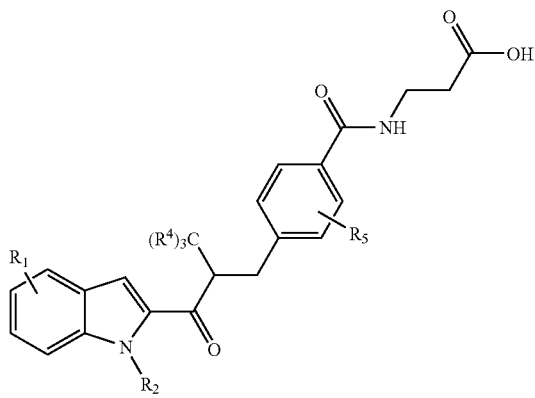
| Example | R¹ | R² | C(R⁴)₃ | R⁵ | Stereo-chem | LCMS conditions, $t_r$ m/z |
|---|---|---|---|---|---|---|
| 31 | 5-Cl | (benzothiazol-2-yl)ethyl | n-propyl | H | RAC | LC B, 2.44 588.3(M + 1) |
| 32 | 5-Cl | Me | methyl | H | A | LC B, 2.13 427.1(M + 1) |
| 33 | 5-Cl | (quinolin-8-yl)methyl | n-propyl | H | A | LC B, 2.25 582.3(M + 1) |
| 34 | 5-Cl | Me | 4-fluorobenzyl | H | B | LC A, 3.69 521.2(M + 1) |
| 35 | 5-Cl | Me | 4-fluorobenzyl | H | A | LC A, 3.69 521.2(M + 1) |
| 36 | 5-Cl | Me | 4-t-Bu-benzyl | H | B | LC B, 2.62 559.3(M + 1) |
| 37 | 5-Cl | Me | 4-t-Bu-benzyl | H | A | LC B, 2.62 559.3(M + 1) |
| 38 | 5-Cl | Me | 2-cyanobenzyl | H | RAC | LC C, 2.20 528.2(M + 1) |

TABLE 1-continued
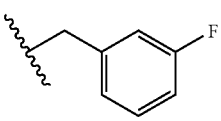
| Example | R¹ | R² | C(R⁴)₃ | R⁵ | Stereo-chem | LCMS conditions, $t_r$ m/z |
|---|---|---|---|---|---|---|
| 39 | 5-Cl | 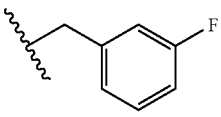 3-F benzyl | n-propyl | H | B | LC B, 2.58 549.2(M + 1) |
| 40 | 5-Cl | 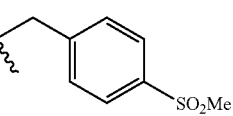 3-F benzyl | n-propyl | H | A | LC B, 2.58 549.2(M + 1) |
| 41 | 5-Cl | 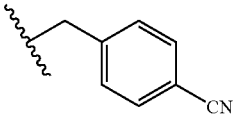 4-SO₂Me benzyl | n-propyl | H | A | LC B, 2.30 609.2(M + 1) |
| 42 | 5-Cl | Et | n-propyl | H | B | LC B, 2.48 469.2(M + 1) |
| 43 | 5-Cl | Et | n-propyl | H | A | LC B, 2.48 469.2(M + 1) |
| 44 | 5-Cl | Me | 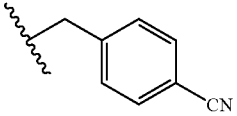 4-CN benzyl | H | B | LC C, 2.19 528.1(M + 1) |
| 45 | 5-Cl | Me | 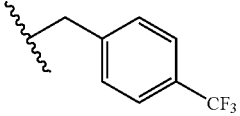 4-CN benzyl | H | A | LC C, 2.19 528.1(M + 1) |
| 46 | 5-Cl | Me | 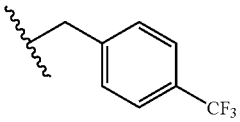 4-CF₃ benzyl | H | B | LC C, 2.44 571.2(M + 1) |
| 47 | 5-Cl | Me | 4-CF₃ benzyl | H | A | LC C, 2.44 571.2(M + 1) |

TABLE 1-continued
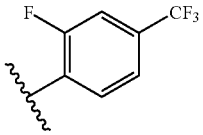
| Example | R¹ | R² | C(R⁴)₃ | R⁵ | Stereo-chem | LCMS conditions, $t_r$ m/z |
|---|---|---|---|---|---|---|
| 48 | 5-Cl | 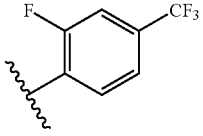 | n-propyl | H | B | LC A, 4.13 617.4(M + 1) |
| 49 | 5-Cl | 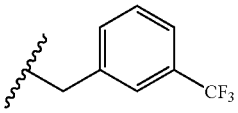 | n-propyl | H | A | LC A, 4.13 617.4(M + 1) |
| 50 | 5-Cl | 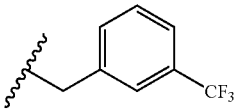 | n-propyl | H | B | LC A, 4.06 599.2(M + 1) |
| 51 | 5-Cl | 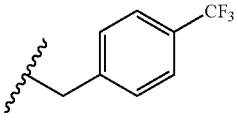 | n-propyl | H | A | LC A, 4.06 599.2(M + 1) |
| 52 | 5-Cl | 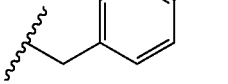 | n-propyl | H | B | LC A, 4.09 599.2(M + 1) |
| 53 | 5-Cl | 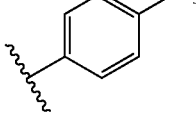 | n-propyl | H | A | LC A, 4.09 599.2(M + 1) |
| 54 | 5-Cl | 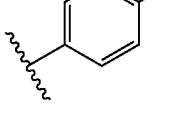 | n-propyl | H | B | LC A, 4.07 585.1(M + 1) |
| 55 | 5-Cl |  | n-propyl | H | A | LC A, 4.07 585.1(M + 1) |

TABLE 1-continued
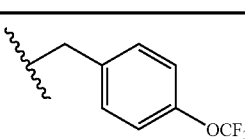
| Example | R¹ | R² | C(R⁴)₃ | R⁵ | Stereo-chem | LCMS conditions, t$_r$ m/z |
|---|---|---|---|---|---|---|
| 56 | 5-Cl | 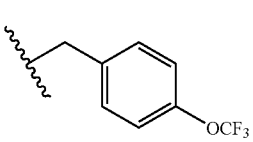 | ethyl | H | RAC | LC A, 4.02 601.1(M + 1) |
| 57 | 5-Cl | 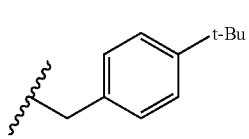 | methyl | H | RAC | LC A, 3.93 587.0(M + 1) |
| 58 | 5-Cl | 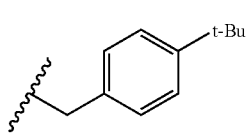 | methyl | H | A | LC B, 2.64 559.2(M + 1) |
| 59 | 5-Cl | 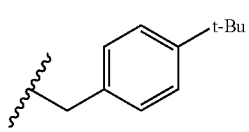 | Ethyl | H | B | LC B, 2.69 573.2(M + 1) |
| 60 | 5-Cl | 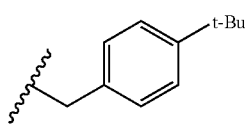 | Ethyl | H | A | LC B, 2.69 573.2(M + 1) |
| 61 | 5-Cl | 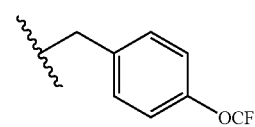 | 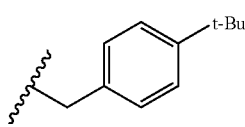 | H | B | LC C, 2.89 719.3(M + 1) |
| 62 | 5-Cl | 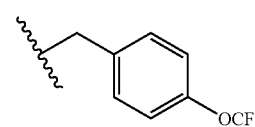 | 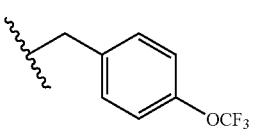 | H | A | LC C, 2.89 719.3(M + 1) |
| 63 | 5-Cl | 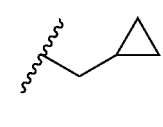 |  | H | A | LC A, 4.22 627.3(M + 1) |

TABLE 1-continued

| Example | R¹ | R² | C(R⁴)₃ | R⁵ | Stereo-chem | LCMS conditions, $t_r$ m/z |
|---|---|---|---|---|---|---|
| 64 | 5-Cl | 4-OCF₃-benzyl | cyclopropylmethyl | H | B | LC A, 4.22 627.3(M + 1) |
| 65 | 5-OBn | 4-OCF₃-benzyl | cyclopropylmethyl | H | A | LC A, 4.50 667.3(M + 1) |
| 66 | 5-Cl | 4-CF₃-benzyl | cyclopropylmethyl | H | C | LC B, 2.71 611.1(M + 1) |
| 67 | 5-Cl | 4-CF₃-benzyl | cyclopropylmethyl | H | D | LC B, 2.71 611.1(M + 1) |
| 68 | 5-Cl | 4-t-Bu-benzyl | n-propyl | H | A | LC A, 4.12 573.5(M + 1) |
| 69 | 5-Cl | 4-t-Bu-benzyl | n-propyl | H | B | LC B, 2.91 573.2(M + 1) |
| 70 | 5-OMe | 4-OCF₃-benzyl | cyclopropylmethyl | H | B | LC B, 2.61 623.1(M + 1) |
| 71 | 5-OMe | 4-OCF₃-benzyl | cyclopropylmethyl | H | A | LC B, 2.61 623.1(M + 1) |

TABLE 1-continued

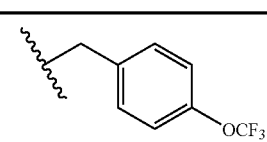

| Example | R¹ | R² | C(R⁴)₃ | R⁵ | Stereo-chem | LCMS conditions, t$_r$ m/z |
|---|---|---|---|---|---|---|
| 72 | 5-cyclopropyloxy | 4-OCF₃-benzyl | CH₂-cyclopropyl | H | RAC | LC A, 4.34 663.4(M + 1) |
| 73 | 5-Cl | 4-t-Bu-benzyl | n-propyl | Br | A | LC A, 4.45 667.3(M + 1) |
| 74 | 5-Cl | 4-OCF₃-benzyl | n-propyl | H | B | LC A, 4.06 601.3(M + 1) |
| 75 | 5-Cl | 4-OCF₃-benzyl | n-propyl | H | A | LC A, 4.06 601.1(M + 1) |
| 76 | 6-CF₃ | 4-t-Bu-benzyl | n-propyl | H | A | LC A, 4.33 621.4(M + 1) |
| 77 | 6-CF₃ | 4-t-Bu-benzyl | n-propyl | H | B | LC A, 4.33 621.4(M + 1) |
| 78 | 6-CF₃ | 3-CF₃-pyridinylmethyl | n-propyl | H | B | LC A, 4.08 633.3(M + 1) |
| 79 | 6-CF₃ | 4-CF₃-benzyl | n-propyl | H | A | LC A, 4.08 633.3(M + 1) |

TABLE 1-continued
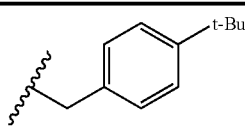
| Example | R¹ | R² | C(R⁴)₃ | R⁵ | Stereo-chem | LCMS conditions, t$_r$ m/z |
|---|---|---|---|---|---|---|
| 80 | 5-Cl | 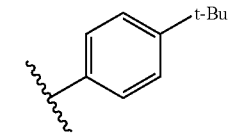 t-Bu | i-propyl | H | RAC | LC A, 4.25 587.4(M + 1) |
| 81 | 6-CF₃ | 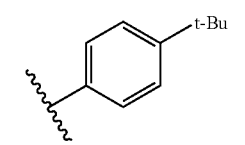 t-Bu | n-propyl | H | A | LC A, 4.27 607.3(M + 1) |
| 82 | 6-CF₃ | 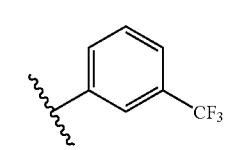 t-Bu | n-propyl | H | B | LC A, 4.27 607.4(M + 1) |
| 83 | 5-Cl | 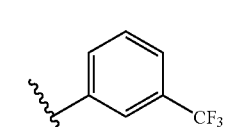 CF₃ | n-propyl | H | A | LC B, 2.69 585.1(M + 1) |
| 84 | 5-Cl | 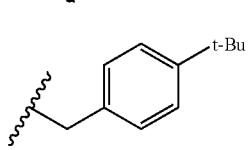 CF₃ | n-propyl | H | B | LC B, 2.69 585.1(M + 1) |
| 85 | 5-Cl | 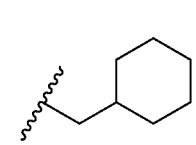 t-Bu | 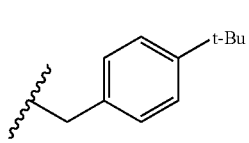 | H | B | LC A, 4.55 641.4(M + 1) |
| 86 | 5-Cl | 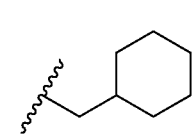 t-Bu | 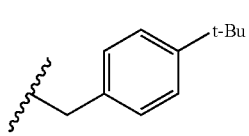 | H | A | LC A, 4.55 641.4(M + 1) |
| 87 | 5-Cl | 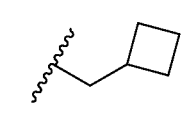 t-Bu |  | H | RAC | LC A, 4.42 613.4(M + 1) |

TABLE 1-continued

| Example | R¹ | R² | C(R⁴)₃ | R⁵ | Stereo-chem | LCMS conditions, t$_r$ m/z |
|---|---|---|---|---|---|---|
| 88 | 5-OCF₃ | 4-t-Bu-benzyl | cyclopropylmethyl | H | A | LC A, 4.29 649.4(M + 1) |
| 89 | 5-OCF₃ | 4-t-Bu-benzyl | cyclopropylmethyl | H | B | LC A, 4.29 649.4(M + 1) |
| 90 | 5-OCF₃ | 4-t-Bu-phenyl | cyclopropylmethyl | H | A | LC A, 4.31 635.4(M + 1) |
| 91 | 5-OCF₃ | 4-t-Bu-phenyl | cyclopropylmethyl | H | B | LC A, 4.31 635.4(M + 1) |
| 92 | 5-Cl | 3-F-phenyl | n-propyl | H | A | LC A, 3.81 535.2(M + 1) |
| 93 | 5-Cl | 6-CF₃-pyridin-2-yl | n-propyl | H | A | LC B, 2.39 532.2(M + 1) |
| 94 | 5-Cl | 4-Cl-phenyl | n-propyl | H | A | LC A, 3.84 551.3(M + 1) |

TABLE 1-continued

| Example | R¹ | R² | C(R⁴)₃ | R⁵ | Stereo-chem | LCMS conditions, t$_r$ m/z |
|---|---|---|---|---|---|---|
| 95 | 5-Cl | 3,5-dimethylphenyl | n-propyl | H | A | LC A, 3.84 545.3(M + 1) |
| 96 | 5-Cl | quinolin-3-yl | n-propyl | H | B | LC D, 1.26 568.4(M + 1) |
| 97 | 5-Cl | quinolin-3-yl | n-propyl | H | A | LC D, 1.26 568.4(M + 1) |
| 98 | 5-OMe | 4-t-Bu-phenyl | cyclopropylmethyl | H | A | LC D, 1.33 581.5(M + 1) |
| 99 | 5-OMe | 4-t-Bu-phenyl | cyclopropylmethyl | H | B | LC D, 1.33 581.5(M + 1) |
| 100 | 5-OMe | 4-t-Bu-benzyl | cyclopropylmethyl | H | A | LC D, 1.34 595.5(M + 1) |
| 101 | 5-Cl | 6-methoxynaphthalen-2-yl | cyclopropylmethyl | H | A | LC A, 4.05 597.3(M + 1) |

TABLE 1-continued

| Example | R¹ | R² | C(R⁴)₃ | R⁵ | Stereo-chem | LCMS conditions, $t_r$ m/z |
|---|---|---|---|---|---|---|
| 102 | 5-CF₃ | 3-CF₃-phenyl | n-propyl | H | A | LC B, 2.62 617(M + 1) |
| 103 | 5-CF₃ | 3-CF₃-phenyl | n-propyl | H | B | LC B, 2.62 617(M + 1) |
| 104 | 5-Cl | 3-F-4-methylphenyl | n-propyl | H | A | LC A, 3.99 549.3(M + 1) |
| 105 | 5-Cl | 3-F-4-methylphenyl | n-propyl | H | B | LC A, 3.99 549.3(M + 1) |
| 106 | 5-Cl | 3,4-difluorophenyl | n-propyl | H | A | LC A, 3.87 553.3(M + 1) |
| 107 | 5-Cl | 2,3-dihydrobenzo[1,4]dioxin-6-yl | n-propyl | H | A | LC A, 3.81 575.3(M + 1) |
| 108 | 5-Cl | 2,3-dihydrobenzo[1,4]dioxin-6-yl | n-propyl | H | B | LC A, 3.81 575.3(M + 1) |

TABLE 1-continued

| Example | R¹ | R² | C(R⁴)₃ | R⁵ | Stereo-chem | LCMS conditions, $t_r$ m/z |
|---|---|---|---|---|---|---|
| 109 | 5-Cl | 4-t-Bu-benzyl | n-propyl | 3-F | B | LC C, 2.81 617.5(M + 1) |
| 110 | 5-Cl | 4-t-Bu-benzyl | n-propyl | 3-F | A | LC B, 2.91 617.2(M + 1) |
| 111 | 5-Cl | 3-OCF₃-benzyl | n-pentyl | H | A | LC C, 2.78 629.2(M + 1) |
| 112 | 5-Cl | 3-OCF₃-benzyl | n-pentyl | H | B | LC C, 2.78 629.2(M + 1) |
| 113 | 5-Cl | 3-OCF₃-benzyl | n-propyl | H | A | LC A, 4.05 601.3(M + 1) |
| 114 | 5-Cl | 7-OCF₃-naphth-2-yl | n-propyl | H | A | LC A, 4.24 651.4(M + 1) |
| 115 | 5-Cl | 7-OCF₃-naphth-2-yl | n-propyl | H | B | LC A, 4.24 651.4(M + 1) |
| 116 | 5-CF₃ | 3,4-difluorobenzyl | n-propyl | H | RAC | LC B, 2.61 587.2(M + 1) |

TABLE 1-continued

| Example | R¹ | R² | C(R⁴)₃ | R⁵ | Stereo-chem | LCMS conditions, t$_r$ m/z |
|---|---|---|---|---|---|---|
| 117 | 5-CF₃ | 4-CF₃-benzyl | n-propyl | H | B | LC B, 2.70 633.2(M + 1) |
| 118 | 5-CF₃ | 4-CF₃-benzyl | n-propyl | H | A | LC B, 2.70 633.2(M + 1) |
| 119 | 5-CF₃ | 6-OMe-naphth-2-yl | n-propyl | H | A | LC B, 2.71 631.2(M + 1) |
| 120 | 5-CF₃ | 6-OMe-naphth-2-yl | n-propyl | H | B | LC B, 2.71 631.2(M + 1) |
| 121 | 5-CF₃ | 3-OCF₃-benzyl | n-propyl | H | A | LC B, 2.72 635.2(M + 1) |
| 122 | 5-CF₃ | 3-OCF₃-benzyl | n-propyl | H | B | LC B, 2.72 635.2(M + 1) |
| 123 | 5-Cl | 1,1,4,4-tetramethyltetralin-6-yl | n-propyl | H | RAC | LC B, 3.08 627.3(M + 1) |

TABLE 1-continued
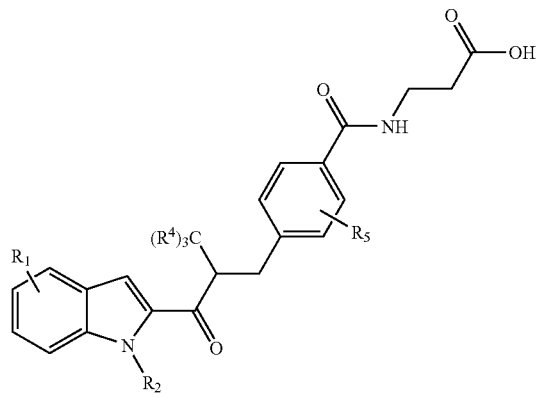
| Example | R¹ | R² | C(R⁴)₃ | R⁵ | Stereo-chem | LCMS conditions, t$_r$ m/z |
|---|---|---|---|---|---|---|
| 124 | 5-Cl | 4'-fluorobiphenyl-4-yl | n-propyl | H | RAC | LC B, 2.78 611.2(M + 1) |
| 125 | 5-Cl | 4-Me-3-CF₃-phenyl | n-propyl | H | RAC | LC A, 4.16 599.5(M + 1) |
| 126 | 5-Cl | 4-OCF₃-3-F-phenyl | n-propyl | H | RAC | LC A, 4.11 619.4(M + 1) |
| 127 | 5-Cl | 3-Br-phenyl | n-propyl | H | RAC | LC C, 2.68 597.2(M + 1) |
| 128 | 5-Cl | 4-cyclohexylphenyl | n-propyl | H | A | LC C, 2.92 599.5(M + 1) |
| 129 | 5-Cl | 4-cyclohexylphenyl | n-propyl | H | B | LC C, 2.92 599.5(M + 1) |

TABLE 1-continued
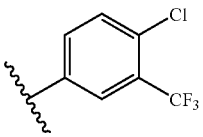
| Example | R¹ | R² | C(R⁴)₃ | R⁵ | Stereo-chem | LCMS conditions, $t_r$ m/z |
|---|---|---|---|---|---|---|
| 130 | 5-Cl | 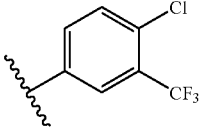 4-Cl, 3-CF₃ | n-propyl | H | A | LC B, 2.75 619.1(M + 1) |
| 131 | 5-Cl | 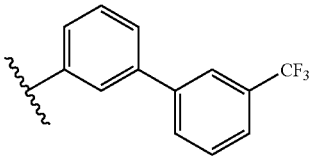 4-Cl, 3-CF₃ | n-propyl | H | B | LC B, 2.75 619.1(M + 1) |
| 132 | 5-Cl | 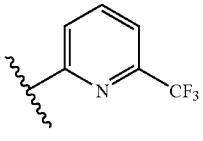 3'-CF₃-biphenyl | n-propyl | H | RAC | LC B, 2.87 661.2(M + 1) |
| 133 | 5-Cl | 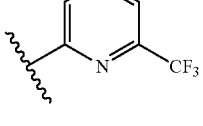 6-CF₃-pyridin-2-yl | n-propyl | H | A | LC B, 2.53 586.1(M + 1) |
| 134 | 5-Cl | 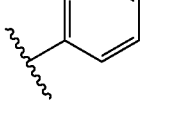 6-CF₃-pyridin-2-yl | n-propyl | H | B | LC B, 2.53 586.1(M + 1) |
| 135 | 5-Cl | 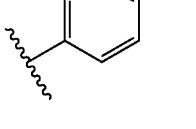 4-CF₃ | n-pentyl | H | A | LC B, 2.85 613.2(M + 1) |
| 136 | 5-Cl | 4-CF₃ | n-pentyl | H | B | LC B, 2.85 613.2(M + 1) |

TABLE 1-continued

| Example | R¹ | R² | C(R⁴)₃ | R⁵ | Stereo-chem | LCMS conditions, $t_r$ m/z |
|---|---|---|---|---|---|---|
| 137 | 5-Cl | 4-(prop-1-enyl)phenyl (Me) | n-propyl | H | RAC | LC A, 4.14 557.4(M + 1) |
| 138 | 5-Cl | 3-(cyclopent-1-enyl)phenyl | n-propyl | H | RAC | LC A, 4.32 583.4(M + 1) |
| 139 | 5-CF₃ | 4-t-Bu-benzyl | n-propyl | H | RAC | LC A, 4.31 621.5(M + 1) |
| 140 | 5-Cl | 4-OMe-3-CF₃-benzyl | n-propyl | H | A | LC A, 4.02 615.4(M + 1) |
| 141 | 5-Cl | 4-OMe-3-CF₃-benzyl | n-propyl | H | B | LC A, 4.02 615.4(M + 1) |
| 142 | 5-Cl | 3,4-(CF₃)-benzyl | n-propyl | 3-F | B | LC A, 4.12 617.4(M + 1) |
| 143 | 5-Cl | 4-CF₃-benzyl | n-propyl | 3-F | A | LC A, 4.12 617.4(M + 1) |

TABLE 1-continued
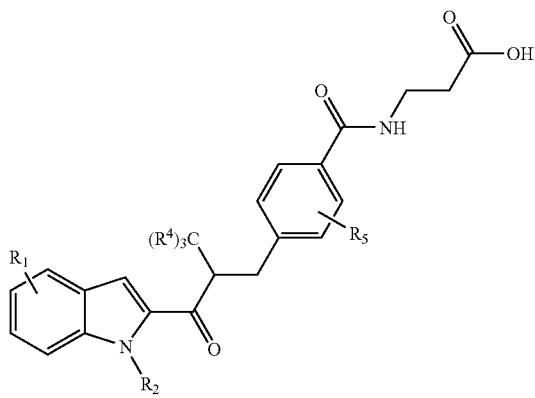
| Example | R¹ | R² | C(R⁴)₃ | R⁵ | Stereo-chem | LCMS conditions, t$_r$ m/z |
|---|---|---|---|---|---|---|
| 144 | 5-Cl | 4-(n-Pr)-phenyl | n-propyl | H | A | LC B, 2.76 559.2(M + 1) |
| 145 | 5-Cl | 4-OEt-phenyl | n-propyl | H | A | LC B, 2.60 561.2(M + 1) |
| 146 | 5-CF₃ | 4-OCF₃-benzyl | n-propyl | H | B | LC A, 4.09 649.4(M + 1) |
| 147 | 5-CF₃ | 4-OCF₃-benzyl | n-propyl | H | A | LC A, 4.09 649.4(M + 1) |
| 148 | 5-CF₃ | 6-CF₃-pyridin-2-yl-methyl | n-pentyl | H | RAC | LC B, 2.69 648.2(M + 1) |
| 149 | 5-CF₃ | 3-CF₃-benzyl | n-pentyl | H | A | LC A, 4.26 647.5(M + 1) |
| 150 | 5-CF₃ | 3-CF₃-benzyl | n-pentyl | H | B | LC A, 4.26 647.5(M + 1) |

TABLE 1-continued
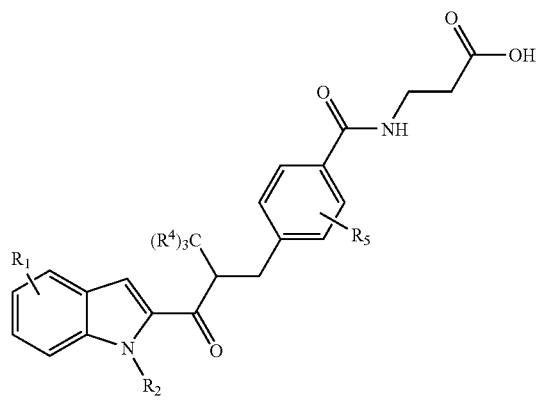
| Example | R¹ | R² | C(R⁴)₃ | R⁵ | Stereo-chem | LCMS conditions, $t_r$ m/z |
|---|---|---|---|---|---|---|
| 151 | 5-CF₃ | 6-CF₃-pyridin-2-yl | n-propyl | H | A | LC B, 3.88 620.4(M + 1) |
| 152 | 5-CF₃ | 6-CF₃-pyridin-2-yl | n-propyl | H | B | LC B, 3.88 620.4(M + 1) |
| 153 | 5-Cl | 3-CF₃-phenyl | n-pentyl | 3-F | A | LC A, 4.30 631.4(M + 1) |
| 154 | 5-Cl | 3-CF₃-phenyl | n-pentyl | 3-F | B | LC A, 4.30 631.4(M + 1) |
| 155 | 5-Cl | 4-CF₃-pyridin-2-yl | n-propyl | H | RAC | LC D, 1.28 586.1(M + 1) |
| 156 | 5-Cl | 3-CF₃-phenyl | n-pentyl | 3-Br | A | LC A, 3.03 693.1(M + 1) |
| 157 | 5-Cl | 6-CF₃-pyridin-2-yl | n-pentyl | H | A | LC A, 3.98 614.5(M + 1) |

TABLE 1-continued

| Example | R¹ | R² | C(R⁴)₃ | R⁵ | Stereo-chem | LCMS conditions, t$_r$ m/z |
|---|---|---|---|---|---|---|
| 158 | 5-Cl | 6-(trifluoromethyl)pyridin-2-yl | n-pentyl | H | B | LC A, 3.98 614.5(M + 1) |
| 159 | 5-Cl | 3-(trifluoromethyl)phenyl | n-butyl | H | A | LC B, 2.80 599.2(M + 1) |
| 160 | 5-Cl | 3-(trifluoromethyl)phenyl | n-butyl | H | B | LC B, 2.80 599.2(M + 1) |
| 161 | 5-F | 3-(trifluoromethyl)phenyl | n-pentyl | H | A | LC A, 4.02 597.5(M + 1) |
| 162 | 5-F | 3-(trifluoromethyl)phenyl | n-pentyl | H | B | LC A, 4.02 597.5(M + 1) |
| 163 | 5-F | 3-(trifluoromethyl)phenyl | n-propyl | H | A | LC A, 3.80 569.5(M + 1) |
| 164 | 5-F | 3-(trifluoromethyl)phenyl | n-propyl | H | B | LC A, 3.80 569.5(M + 1) |

TABLE 1-continued

| Example | R¹ | R² | C(R⁴)₃ | R⁵ | Stereo-chem | LCMS conditions, $t_r$ m/z |
|---|---|---|---|---|---|---|
| 165 | 5-Cl | 4-CF₃-benzyl | n-pentyl | H | B | LC A, 4.16 627.5(M + 1) |
| 166 | 5-Cl | 4-CF₃-benzyl | n-pentyl | H | A | LC A, 4.16 627.5(M + 1) |
| 167 | 5-CF₃ | 4-CF₃-benzyl | n-pentyl | H | B | LC A, 4.17 661.5(M + 1) |
| 168 | 5-CF₃ | 4-CF₃-benzyl | n-pentyl | H | A | LC A, 4.17 661.5(M + 1) |
| 169 | 5-Cl | 4-Cl-3-CF₃-benzyl | n-pentyl | H | A | LC A, 4.20 647.4(M + 1) |
| 170 | 5-Cl | 4-Cl-3-CF₃-benzyl | n-pentyl | H | B | LC A, 4.20 647.4(M + 1) |
| 171 | 5-CF₃ | 4-OCF₃-benzyl | n-pentyl | H | B | LC A, 4.16 677.5(M + 1) |
| 172 | 5-CF₃ | 4-OCF₃-benzyl | n-pentyl | H | A | LC A, 4.16 677.5(M + 1) |

TABLE 1-continued

| Example | R¹ | R² | C(R⁴)₃ | R⁵ | Stereo-chem | LCMS conditions, $t_r$ m/z |
|---|---|---|---|---|---|---|
| 173 | 5-F | 4-t-Bu-benzyl | n-pentyl | H | B | LC A, 4.18 599.6(M + 1) |
| 174 | 5-F | 4-t-Bu-benzyl | n-pentyl | H | A | LC A, 4.18 599.6(M + 1) |
| 175 | 5-F | 4-CF₃-benzyl | n-pentyl | H | B | LC A, 4.20 611.2(M + 1) |
| 176 | 5-F | 4-CF₃-benzyl | n-pentyl | H | A | LC A, 4.20 611.2(M + 1) |
| 177 | 5-F | 4-OCF₃-benzyl | n-pentyl | H | A | LC C, 2.72 627.5(M + 1) |
| 178 | 5-F | 4-Cl-3-CF₃-benzyl | n-pentyl | H | A | LC A, 4.04 631.5(M + 1) |
| 179 | 5-F | 4-Cl-3-CF₃-benzyl | n-pentyl | H | B | LC C, 2.75 631.4(M + 1) |

TABLE 2

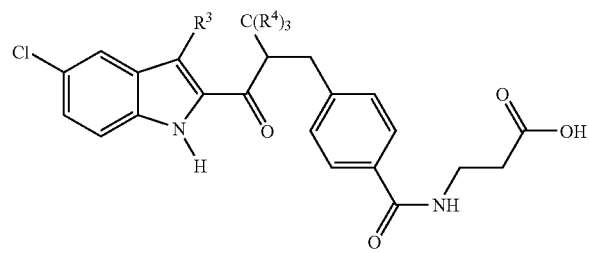

| Example | R³ | C(R⁴)₃ | Stereo-chem | LCMS conditions, $t_r$, m/z |
|---|---|---|---|---|
| 180 | H | n-propyl | A | LC A, 3.43 441.1(M + 1) |
| 181 | H | 4-OCF₃-benzyl | B | LC A, 3.71 573.0(M + 1) |
| 182 | H | 4-OCF₃-benzyl | A | LC A, 3.71 573.0(M + 1) |
| 183 | H | 2-OCF₃-benzyl | RAC | LC B, 2.34 573.1(M + 1) |

TABLE 2-continued

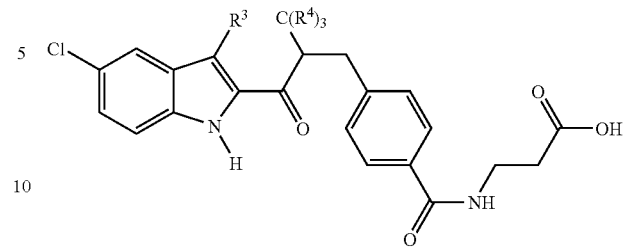

| Example | R³ | C(R⁴)₃ | Stereo-chem | LCMS conditions, $t_r$, m/z |
|---|---|---|---|---|
| 184 | H | 3-OCF₃-benzyl | C | LC A, 3.72 573.0(M + 1) |
| 185 | H | 3-OCF₃-benzyl | D | LC A, 3.72 573.0(M + 1) |
| 186 | Me | benzyl | RAC | LC B, 2.26 503.2(M + 1) |
| 187 | H | benzyl | RAC | LC A, 3.43 488.9(M + 1) |

TABLE 3

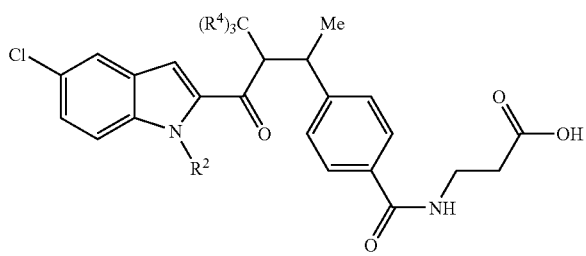

| Example | R² | C(R⁴)₃ | Stereo-chem | LCMS conditions, $t_r$, m/z |
|---|---|---|---|---|
| 188 | H | 4-OCF₃-benzyl | B, syn or anti | LC B, 2.44 587(M + 1) |
| 189 | H | 4-OCF₃-benzyl | A, syn or anti | LC A, 2.43 587(M + 1) |

TABLE 3-continued

[Structure: 5-chloroindole with N-R² substituent, connected via C(=O) to a carbon bearing C(R⁴)₃ group, adjacent to CH(Me) attached to phenyl ring with para-C(=O)NH-CH₂CH₂-COOH]

| Example | R² | C(R⁴)₃ | Stereo-chem | LCMS conditions, t_r, m/z |
|---|---|---|---|---|
| 190 | H | 4-t-Bu-benzyl | A, syn or anti | LC A, 4.07; 559(M + 1) |
| 191 | 3-CF₃-benzyl | allyl | RAC, syn or anti | LC B, 2.66; 597.2(M + 1) |
| 192 | 3-CF₃-benzyl | allyl | RAC, syn or anti | LC B, 2.70; 597.2(M + 1) |
| 193 | 3-CF₃-benzyl | n-propyl | B, syn or anti | LC A, 3.96; 599.3(M + 1) |
| 194 | 3-CF₃-benzyl | n-propyl | A, syn or anti | LC A, 3.96; 599.3(M + 1) |
| 195 | 3-CF₃-benzyl | n-pentyl | B, syn or anti | LC C, 2.76; 627.2(M + 1) |
| 196 | 3-CF₃-benzyl | n-pentyl | A, syn or anti | LC C, 2.77; 627.2(M + 1) |

Biological Assays

The ability of the compounds of the present invention to inhibit the binding of glucagon in treating or preventing type 2 diabetes mellitus and the related conditions can be the following in vitro assays.

Glucagon Receptor Binding Assay

A stable CHO (Chinese hamster ovary) cell line expressing cloned human glucagon receptor was maintained as described (Chicchi et al. *J Biol Chem* 272, 7765-9(1997); Cascieri et al. *J Biol Chem* 274, 8694-7(1999)). To determine antagonistic binding affinity of compounds 0.002 mg of cell membranes from these cells were incubated with $^{125}$I-Glucagon (New England Nuclear, MA) in a buffer containing 50 mM Tris-HCl (pH 7.5), 5 mM MgCl$_2$, 2 mM EDTA, 12% Glycerol, and 0.200 mg WGA coated PVT SPA beads (Amersham), +/−compounds or 0.001 mM unlabeled glucagon. After 3 hours incubation at room temperature, the radioactivity bound to the cell membranes was determined in a radioactive emission detection counter (Wallac-Microbeta). Data were analyzed using the software program Prism® from GraphPad. The IC$_{50}$ were calculated using non-linear regression analysis assuming single site competition. Compounds of the invention generally demonstrate binding activity in the range of about 1 nM to about 500 nM.

Inhibition of Glucagon-stimulated Intracellular cAMP Formation

Exponentially growing CHO cells expressing human glucagon receptor were harvested with the aid of enzyme-free dissociation media (Specialty Media), pelleted at low speed, and re-suspended in the Cell Stimulation Buffer included in the Flash Plate cAMP kit (New England Nuclear, SMP0004A). The adenylate cyclase assay was setup as per manufacturer instructions. Briefly, compounds were diluted from stocks in DMSO and added to cells at a final DMSO concentration of 5%. Cells prepared as above were preincubated in flash plates coated with anti-cAMP antibodies (NEN) in presence of compounds or DMSO controls for 30 minutes, and then stimulated with glucagon (250 pM) for an additional 30 minutes. The cell stimulation was stopped by addition of equal amount of a detection buffer containing lysis buffer as well as $^{125}$I-labeled cAMP tracer (NEN). After 3 hours of incubation at room temperature the bound radioactivity was determined in a liquid scintillation counter (Top-Count-Packard Instruments). Basal activity (100% inhibition) was determined using the DMSO control while 0% inhibition was defined at the amount of pmol cAMP produced by 250 pM glucagon.

Certain embodiments of the invention has been described in detail; however, numerous other embodiments are contemplated as falling within the invention. Thus, the claims are not limited to the specific embodiments described herein. All patents, patent applications and publications of any kind that are cited herein are hereby incorporated by reference in their entirety.

What is claimed is:

1. A compound represented by formula I:

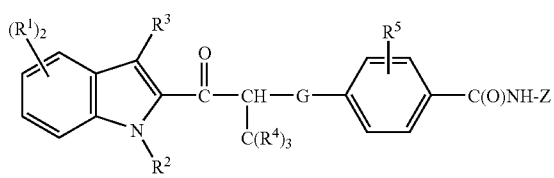

or a pharmaceutically acceptable salt thereof, wherein:
each $R^1$ represents H or is independently selected from the group consisting of:
a) OH, halo, CO$_2$R$^a$, C(O)NR$^b$R$^c$, NR$^b$R$^c$, CN or S(O)$_p$R$^d$; and
b) C$_{1-10}$alkyl, C$_{2-10}$alkenyl, OC$_{1-10}$alkyl and OC$_{3-10}$alkenyl, said groups being optionally substituted with: (1) 1-5 halo groups up to a perhaloalkyl group; (2) 1 oxo group; (3) 1-2 OH groups; (4) 1 phenyl ring, which is optionally substituted as follows: 1-5 halo groups up to perhalo, 1-3 C$_{1-10}$alkyl or alkoxy groups, each being further optionally substituted with 1-5 halo up to perhalo;

$R^2$ represents phenyl optionally substituted with 1-3 halo, C$_{1-6}$alkyl, C$_{1-6}$alkoxy, haloC$_{1-6}$alkyl and haloC$_{1-6}$alkoxy groups;

$R^3$ represents H, C$_{1-6}$alkyl;

3 $R^4$ groups are present, 0-3 of which are C$_{1-8}$alkyl, C$_{2-6}$alkenyl, C$_{2-6}$alkynyl or C$_{1-8}$alkoxy groups, said groups being optionally substituted with: (1) 1-5 halo atoms up to perhaloalkyl; (2) 1 oxo group; (3) 1-2 OH groups; (4) 1-2 C$_{1-10}$alkoxy groups, each optionally substituted with up to five halo atoms or a perhaloalkoxy, 1 OH or CO$_2$R$^a$ group; (5) 1-2 Aryl groups, each optionally substituted as follows: (i) 1-5 halo atoms, (ii) 1 OH, CO$_2$R$^a$, CN, S(O)$_p$R$^d$, NO$_2$ or C(O)NR$^b$R$^c$ group, (iii) 1-2 C$_{1-10}$alkyl or alkoxy groups, each optionally substituted with: 1-5 halo atoms, up to perhaloalkyl;

and 0-1 of which is Aryl optionally substituted as follows: (1) 1-3 halo atoms; (2) 1-2 OH, CO$_2$R$^a$, CN or S(O)$_p$R$^d$ groups; (3) 1-3 C$_{1-8}$alkyl groups optionally substituted with 1-5 halo groups, and (4) 1-3 C$_{1-10}$alkoxy groups, the alkyl portion of which is optionally substituted with 1-5 halo groups, and the remainder are hydrogen atoms;

$R^5$ represents H, halo, C$_{1-6}$ alkyl, C$_{1-6}$alkoxy, haloC$_{1-6}$ alkyl or haloC$_{1-6}$ alkoxy;

G represents —CHR$^x$— wherein R$^x$ represents H or C$_{1-8}$alkyl;

$R^a$ is H or C$_{1-10}$alkyl, optionally substituted with phenyl, OH, OC$_{1-6}$alkyl, CO$_2$H, CO$_2$C$_{1-6}$alkyl and 1-3 halo groups;

$R^b$ is H or C$_{1-10}$alkyl;

$R^c$ is H or is independently selected from: (a) C$_{1-10}$alkyl, (b) Aryl or Ar—C$_{1-6}$alkyl, each optionally substituted with 1-5 halos and 1-3 members selected from the group consisting of: CN, OH, C$_{1-10}$alkyl and OC$_{1-10}$ alkyl, said alkyl and alkoxy being further optionally substituted with 1-5 halo groups up to perhalo;

$R^d$ is C$_{1-10}$alkyl, Aryl or Ar—C$_{1-10}$alkyl;

p is an integer selected from 0, 1 and 2, and and Z is selected from CH$_2$CH$_2$CO$_2$R$^a$, CH$_2$CH(OH) CO$_2$R$^a$ and 5-tetrazolyl.

2. A compound in accordance with claim 1 wherein: each $R^1$ is hydrogen or is selected from the group consisting of: halo, NR$^b$R$^c$, CN, C$_{1-6}$alkyl optionally substituted with 1-3 halo groups, 1 phenyl group or 1 halo substituted phenyl group, and OC$_{1-6}$alkyl, optionally substituted with 1-3 halo groups.

3. A compound in accordance with claim 2 wherein: each $R^1$ represents hydrogen or is selected from the group consisting of: halo, C$_{1-6}$alkoxy optionally substituted with 1-3 halo groups, and C$_{1-6}$alkyl optionally substituted with 1-3 halo groups or 1 phenyl ring.

4. A compound in accordance with claim 3 wherein: each $R^1$ represents hydrogen or is selected from the group consisting of: halo selected from chloro and fluoro, CF$_3$, OCF$_3$, OCH$_3$ and CH$_3$.

5. A compound in accordance with claim 1 wherein $R^3$ represents H or methyl.

6. A compound of formula I:

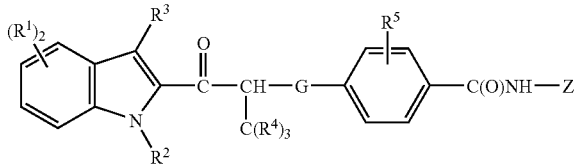

or a pharmaceutically acceptable salt thereof in accordance with claim 1 wherein:
three $R^4$ groups are present, defined as follows: (A) 0-3 $R^4$ groups are $C_{1-6}$alkyl, optionally substituted with: (1) 1-3 halo atoms; (2) 1 OH group; (3) 1 $C_{1-4}$alkoxy group, optionally substituted with up to three halo atoms; (4) 1 Aryl group, optionally substituted with: (i) 1-3 halo atoms, (ii) 1 OH, $CO_2R^a$, CN, $S(O)_pR^d$ or $C(O)NR^bR^c$ group, and (iii) 1-2 $C_{1-4}$alkyl or alkoxy groups, each optionally substituted with: 1-3 halo atoms;
and (B) 0-1 $R^4$ groups are Aryl optionally substituted as follows: (1) 1-3 halo atoms; (2) 1-2 $C_{1-6}$alkyl groups optionally substituted with 1-3 halo atoms, (3) 1 $C_{1-6}$alkoxy group, the alkyl portion of which is optionally substituted with 1-3 halo atoms, and (4) CN,
and the remainder are hydrogen atoms.

7. A compound in accordance with claim 6 wherein:
two $R^4$ groups represent hydrogen, and one $R^4$ is selected from the group consisting of:
(A) $C_{1-6}$alkyl, optionally substituted with: (1) 1-3 halo atoms; (2) 1 OH group; (3) 1 $C_{1-4}$alkoxy group, optionally substituted with up to three halo atoms; (4) 1 Aryl group, optionally substituted with: (i) 1-3 halo atoms, (ii) 1 OH, $CO_2R^a$, CN, $S(O)_pR^d$ or $C(O)NR^bR^c$ group, and (iii) 1-2 $C_{1-4}$alkyl or alkoxy groups, each optionally substituted with: 1-3 halo atoms; and
(B) Aryl optionally substituted with: (1) 1-3 halo atoms; (2) 1 $C_{1-6}$alkyl group optionally substituted with 1-3 halo atoms, (3) 1 $C_{1-6}$alkoxy group, the alkyl portion of which is optionally substituted with 1-3 halo atoms and (4) CN.

8. A compound in accordance with claim 7 wherein:
two $R^4$ groups represent hydrogen and one $R^4$ is selected from the group consisting of:
(A) $C_{1-6}$alkyl and
(B) Aryl optionally substituted with: (1) 1-3 halo atoms; (2) 1 $C_{1-6}$alkyl group optionally substituted with 1-3 halo atoms (3) 1 $C_{1-6}$alkoxy group, the alkyl portion of which is optionally substituted with 1-3 halo atoms and (4) CN.

9. A compound in accordance with claim 1 wherein G represents —$CH_2$— or —$CH(CH_3)$—.

10. A compound in accordance with claim 1 wherein $R^5$ represents H, halo, $C_{1-4}$alkyl, halo$C_{1-4}$alkyl, $C_{1-4}$alkoxy or halo$C_{1-4}$alkoxy.

11. A compound in accordance with claim 10 wherein $R^5$ represents H, fluoro, methyl or methoxy.

12. A compound in accordance with claim 1 wherein Z is $CH_2CH_2CO_2R^a$.

13. A compound in accordance with claim 1 wherein:
$R^1$ is hydrogen or is selected from the group consisting of: halo; $NR^bR^c$; CN; $C_{1-6}$alkyl optionally substituted with 1-3 halo groups, 1 phenyl or halo substituted phenyl group; and $OC_{1-6}$alkyl optionally substituted with 1-3 halo atoms;

$R^2$ is phenyl optionally substituted with 1-3 halo atoms and 1-2 $C_{1-6}$alkyl, $C_{1-6}$alkoxy, halo$C_{1-6}$alkyl and halo$C_{1-6}$alkoxy groups;
$R^3$ represents H or methyl;
three $R^4$ groups are present, defined as follows: (A) 0-3 $R^4$ groups are $C_{1-6}$alkyl, optionally substituted with: (1) 1-3 halo atoms; (2) 1 OH group; (3) 1 $C_{1-4}$alkoxy group, optionally substituted with up to three halo atoms; (4) 1 Aryl group, optionally substituted with: (i) 1-3 halo atoms, (ii) 1 OH, $CO_2R^a$, CN, $S(O)_pR^d$ or $C(O)NR^bR^c$ group, and (iii) 1-2 $C_{1-4}$alkyl or alkoxy groups, each optionally substituted with: 1-3 halo atoms;
and (B) 0-1 $R^4$ groups are Aryl optionally substituted as follows: (1) 1-3 halo atoms; (2) 1-2 $C_{1-6}$alkyl groups optionally substituted with 1-3 halo atoms, (3) 1 $C_{1-6}$alkoxy group, the alkyl portion of which is optionally substituted with 1-3 halo atoms,
and the remainder are hydrogen atoms;
$R^5$ represents H, halo, $C_{1-4}$alkyl, halo$C_{1-4}$alkyl, $C_{1-4}$alkoxy or halo$C_{1-4}$alkoxy;
G represents —$CH_2$— or —$CH(CH_3)$—;
$R^a$ is H or $C_{1-10}$alkyl, optionally substituted with phenyl, OH, $OC_{1-6}$alkyl, $CO_2H$, $CO_2C_{1-6}$alkyl and 1-3 halo groups;
$R^b$ is H or $C_{1-10}$alkyl;
$R^c$ is H or is independently selected from: (a) $C_{1-10}$alkyl, (b) Aryl or Ar—$C_{1-6}$alkyl, each optionally substituted with 1-5 halos and 1-3 members selected from the group consisting of: CN, OH, $C_{1-10}$alkyl and $OC_{1-10}$ alkyl, said alkyl and alkoxy being further optionally substituted with 1-5 halo groups up to perhalo;
$R^d$ is $C_{1-10}$alkyl, Aryl or Ar—$C_{1-10}$alkyl;
p is an integer selected from 0, 1 and 2, and
Z is $CH_2CH_2CO_2R^a$.

14. A compound in accordance with claim 13 wherein:
each $R^1$ represents hydrogen or is selected from the group consisting of: halo, $C_{1-6}$alkoxy optionally substituted with 1-3 halo groups, and $C_{1-6}$alkyl optionally substituted with 1-3 halo groups or 1 phenyl ring;
$R^2$ is phenyl optionally substituted with 1-3 halo atoms, and 1-2 $C_{1-6}$alkyl, $C_{1-6}$alkoxy, halo$C_{1-6}$alkyl and halo$C_{1-6}$alkoxy groups;
$R^3$ represents H or methyl;
two $R^4$ groups represent hydrogen, and one $R^4$ is selected from the group consisting of:
(A) $C_{1-6}$alkyl, optionally substituted with: (1) 1-3 halo atoms; (2) 1 OH group; (3) 1 $C_{1-4}$alkoxy group, optionally substituted with up to three halo atoms; (4) 1 Aryl group, optionally substituted with: (i) 1-3 halo atoms, (ii) 1 OH, $CO_2R^a$, CN, $S(O)_pR^d$ or $C(O)NR^bR^c$ group, and (iii) 1-2 $C_{1-4}$alkyl or alkoxy groups, each optionally substituted with: 1-3 halo atoms; and
(B) Aryl optionally substituted with: (1) 1-3 halo atoms; (2) 1 $C_{1-6}$alkyl group optionally substituted with 1-3 halo atoms, and (3) 1 $C_{1-6}$alkoxy group, the alkyl portion of which is optionally substituted with 1-3 halo atoms;
$R^5$ represents H, fluoro, methyl or methoxy,
and Z is $CH_2CH_2CO_2R^a$.

15. A compound in accordance with claim 1 selected from the following tables:
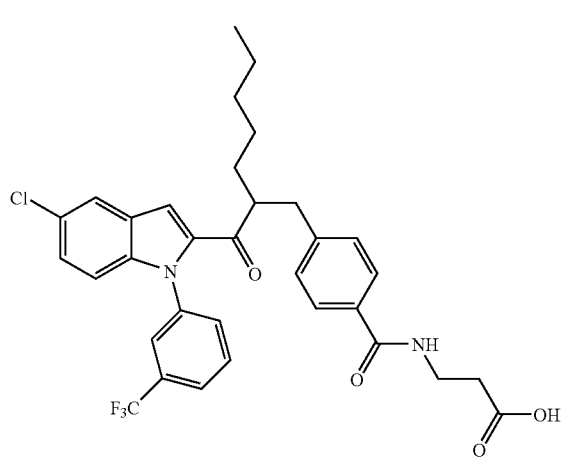
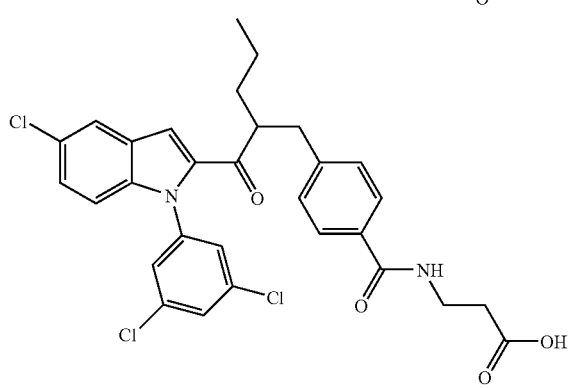
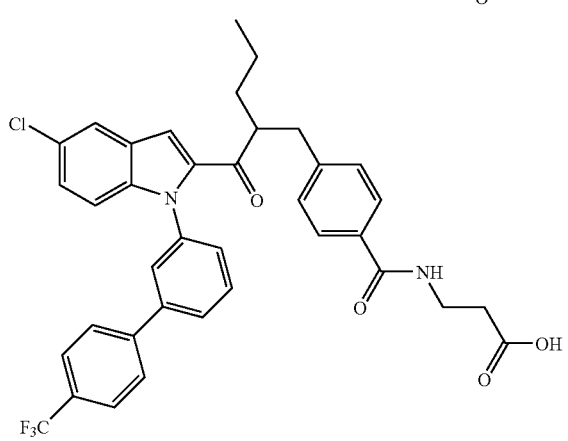
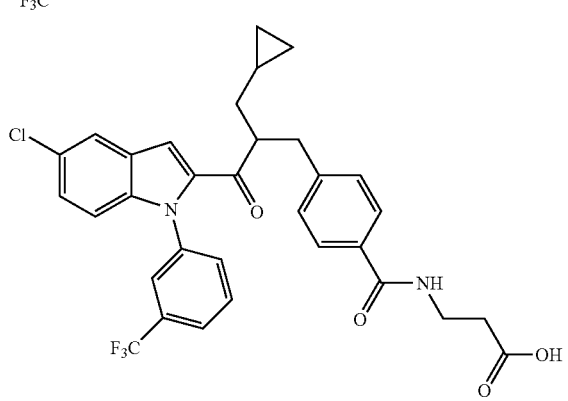
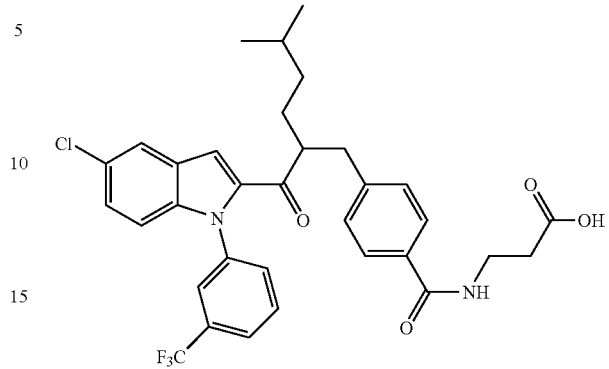
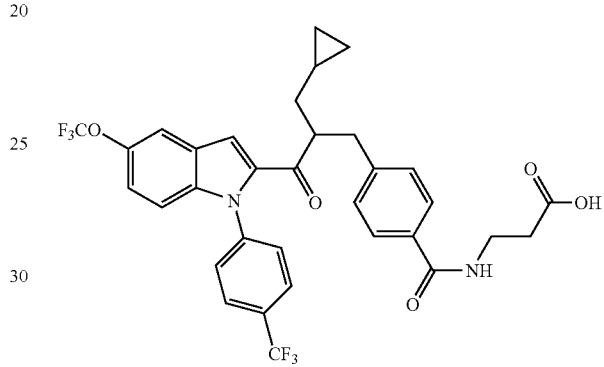
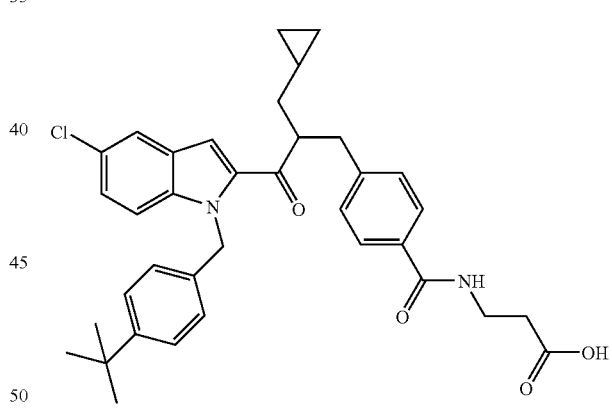
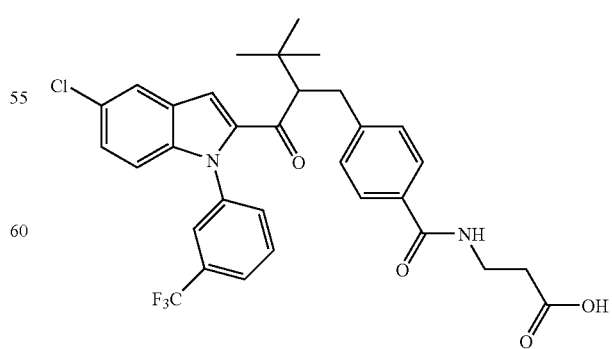
or a pharmaceutically acceptable salt thereof;

TABLE 1

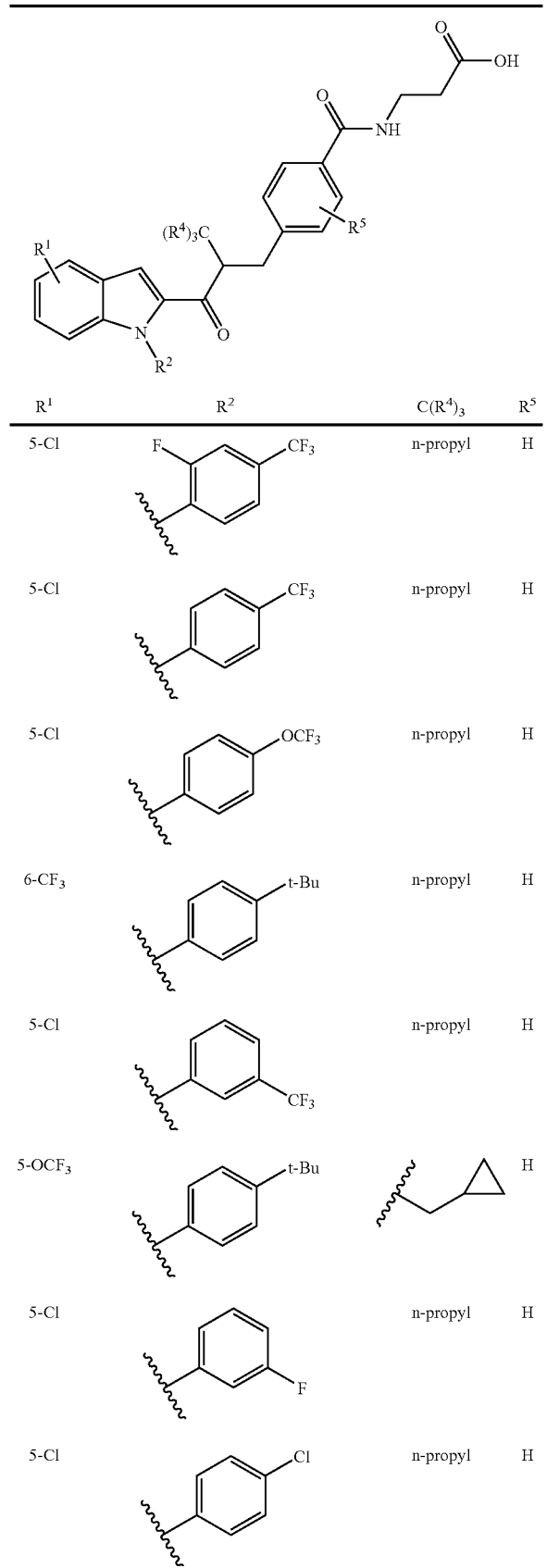

| R¹ | R² | C(R⁴)₃ | R⁵ |
|---|---|---|---|
| 5-Cl | 2-F-4-CF₃-phenyl | n-propyl | H |
| 5-Cl | 4-CF₃-phenyl | n-propyl | H |
| 5-Cl | 4-OCF₃-phenyl | n-propyl | H |
| 6-CF₃ | 4-t-Bu-phenyl | n-propyl | H |
| 5-Cl | 3-CF₃-phenyl | n-propyl | H |
| 5-OCF₃ | 4-t-Bu-phenyl | cyclopropylmethyl | H |
| 5-Cl | 3-F-phenyl | n-propyl | H |
| 5-Cl | 4-Cl-phenyl | n-propyl | H |

TABLE 1-continued

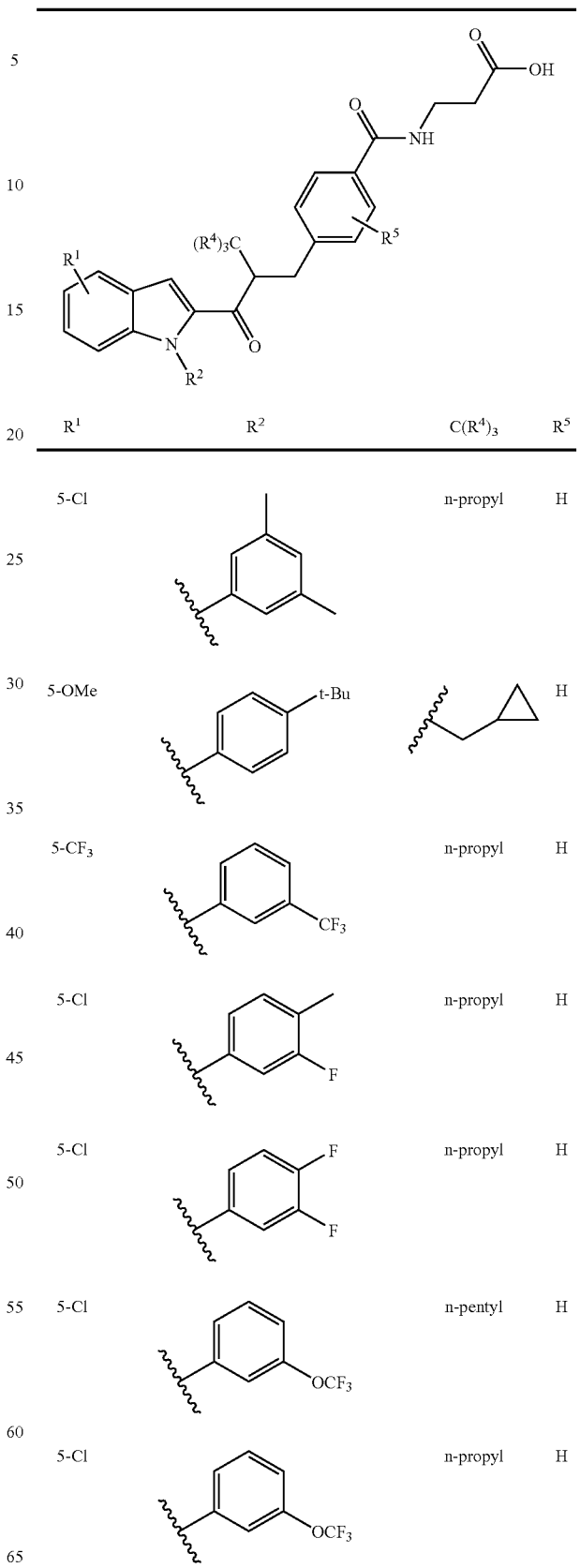

| R¹ | R² | C(R⁴)₃ | R⁵ |
|---|---|---|---|
| 5-Cl | 3,5-dimethylphenyl | n-propyl | H |
| 5-OMe | 4-t-Bu-phenyl | cyclopropylmethyl | H |
| 5-CF₃ | 3-CF₃-phenyl | n-propyl | H |
| 5-Cl | 4-methyl-3-F-phenyl | n-propyl | H |
| 5-Cl | 3,4-diF-phenyl | n-propyl | H |
| 5-Cl | 3-OCF₃-phenyl | n-pentyl | H |
| 5-Cl | 3-OCF₃-phenyl | n-propyl | H |

TABLE 1-continued

[Structure with R¹ on indole, R² on N, C(R⁴)₃ branch, R⁵ on benzamide-NH-CH₂CH₂-COOH]

| R¹ | R² | C(R⁴)₃ | R⁵ |
|---|---|---|---|
| 5-CF₃ | 3,4-difluorophenyl | n-propyl | H |
| 5-CF₃ | 3-(OCF₃)phenyl | n-propyl | H |
| 5-Cl | 4'-fluorobiphenyl-4-yl | n-propyl | H |
| 5-Cl | 4-methyl-3-(CF₃)phenyl | n-propyl | H |
| 5-Cl | 4-(OCF₃)-3-fluorophenyl | n-propyl | H |
| 5-Cl | 3-bromophenyl | n-propyl | H |
| 5-Cl | 4-cyclohexylphenyl | n-propyl | H |
| 5-Cl | 4-chloro-3-(CF₃)phenyl | n-propyl | H |
| 5-Cl | 3'-(CF₃)biphenyl-3-yl | n-propyl | H |
| 5-Cl | 4-(CF₃)phenyl | n-pentyl | H |
| 5-Cl | 4-(1-propenyl)phenyl | n-propyl | H |
| 5-Cl | 3-(cyclopenten-1-yl)phenyl | n-propyl | H |

TABLE 1-continued

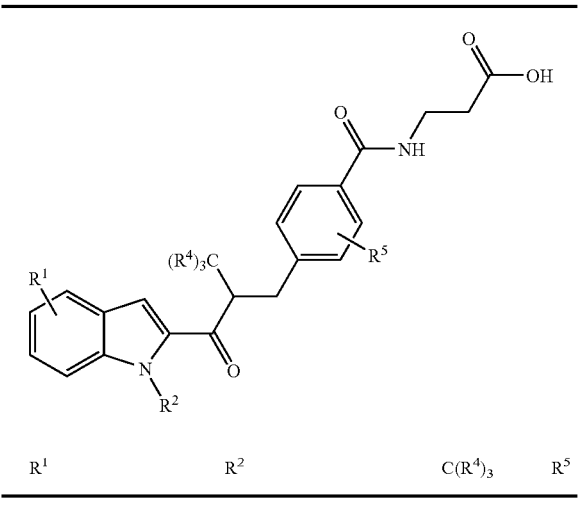

| R¹ | R² | C(R⁴)₃ | R⁵ |
|---|---|---|---|
| 5-Cl | 4-OMe, 3-CF₃ phenyl | n-propyl | H |
| 5-Cl | 4-n-Pr phenyl | n-propyl | H |
| 5-Cl | 4-OEt phenyl | n-propyl | H |
| 5-CF₃ | 3-CF₃ phenyl | n-pentyl | H |
| 5-Cl | 3-CF₃ phenyl | n-pentyl | 3-F |
| 5-Cl | 3-CF₃ phenyl | n-pentyl | 3-Br |

TABLE 1-continued

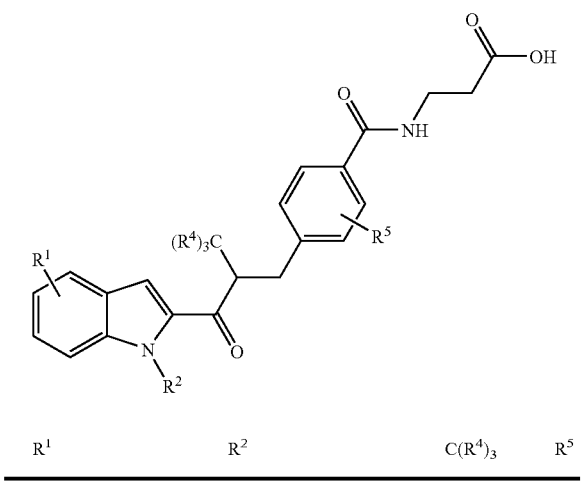

| R¹ | R² | C(R⁴)₃ | R⁵ |
|---|---|---|---|
| 5-Cl | 3-CF₃ phenyl | n-butyl | H |
| 5-F | 3-CF₃ phenyl | n-pentyl | H |
| 5-F | 3-CF₃ phenyl | n-propyl | H |
| 5-Cl | 4-Cl, 3-CF₃ phenyl | n-pentyl | H |
| 5-F | 4-Cl, 3-CF₃ phenyl | n-pentyl | H | or a pharmaceutically acceptable salt thereof, and

TABLE 3

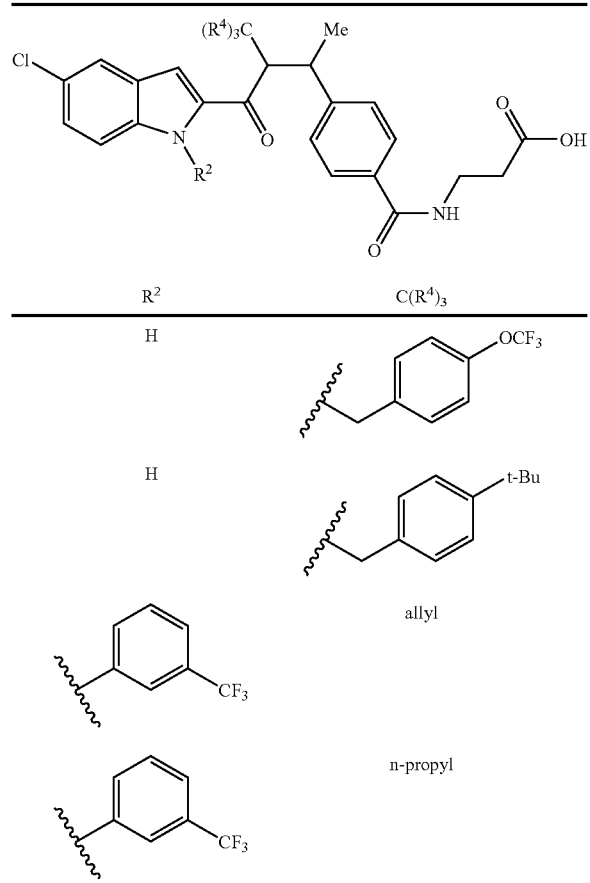

TABLE 3-continued

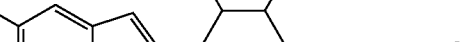

or a pharmaceutically acceptable salt thereof.

16. A pharmaceutical composition which is comprised of a compound in accordance with claim 1 in combination with a pharmaceutically acceptable carrier.

17. A method of treating type 2 diabetes mellitus in a mammalian patient in need of such treatment, comprising administering to said patient a compound in accordance with claim 1 in an amount that is effective to treat type 2 diabetes mellitus.

* * * * *